US008206940B2

(12) United States Patent
Feng et al.

(10) Patent No.: US 8,206,940 B2
(45) Date of Patent: Jun. 26, 2012

(54) **METHODS FOR DIAGNOSIS OF *CLOSTRIDIUM DIFFICILE* AND METHODS AND VECTORS FOR RECOMBINANT TOXIN EXPRESSION**

(75) Inventors: Hanping Feng, Framingham, MA (US); Saul Tzipori, Shrewsbury, MA (US); Guilin Yang, Shenzhen (CN)

(73) Assignee: Tufts University, Boston, MA (US)

( * ) Notice: Subject to any disclaimer, the term of this patent is extended or adjusted under 35 U.S.C. 154(b) by 0 days.

(21) Appl. No.: 12/992,330

(22) PCT Filed: May 15, 2009

(86) PCT No.: PCT/US2009/003055
§ 371 (c)(1),
(2), (4) Date: Nov. 12, 2010

(87) PCT Pub. No.: WO2009/139919
PCT Pub. Date: Nov. 19, 2009

(65) Prior Publication Data
US 2011/0065123 A1 Mar. 17, 2011

Related U.S. Application Data

(60) Provisional application No. 61/127,757, filed on May 15, 2008.

(51) Int. Cl.
*G01N 33/53* (2006.01)
(52) U.S. Cl. ........... 435/7.32; 435/7.2; 435/7.1; 435/29; 435/34; 435/39; 424/247.1; 424/167.1
(58) Field of Classification Search ................ None
See application file for complete search history.

(56) References Cited

U.S. PATENT DOCUMENTS

| | | | |
|---|---|---|---|
| 5,098,826 | A | 3/1992 | Wilkins et al. |
| 6,503,722 | B1 * | 1/2003 | Valkirs .................. 435/7.2 |
| 6,939,548 | B2 | 9/2005 | Wilkins et al. |
| 2003/0054493 | A1 * | 3/2003 | Williams et al. ......... 435/69.3 |
| 2006/0233797 | A1 * | 10/2006 | Gujrathi .................. 424/144.1 |

FOREIGN PATENT DOCUMENTS
WO WO98/45706 A1 10/1998

OTHER PUBLICATIONS

Novak-Weekley et al. "Comparison of the Premier Toxin A and B Assay and the TOX A/B II Assay for Diagnosis of *Clostridium difficile* Infection" Clin Vaccin Immunol, 2008, vol. 15, pp. 575-579.
Nusrat et al. "*Clostridium difficile* Toxins Disrupt Epithelial Barrier Function by Altering Membrane Microdomain Localization of Tight Junction Proteins" Infect Immun, 2001, pp. 1329-1336.
Obrien et al. "The Emerging Infectious Challenge of *Clostridium difficile*—Associated Disease in Massachusetts Hospitals:Clinical and Economic Consequences" Infect Control Hosp Epidemiol, 2007, vol. 28, pp. 1219-1227.
Owens et al. "Antimicrobial-Associated Risk Factors for *Clostridium difficile* Infection" Clin Infect Dis, 2008, vol. 46, pp. S19-S31.
Peterson et al. "Detection of Toxigenic *Clostridium difficile* in Stool Samples by Real-Time Polymerase Chain Reaction for the Diagnosis of *C. difficile*—Associated Diarrhea" Clin Infect Dis, 2007, vol. 45, pp. 1152-1160.
Pfeifer et al. "Cellular Uptake of *Clostridium difficile* Toxin B" J Biol Chem, 2003, J Biol Chem, vol. 278, pp. 44535-44541.
Planche et al. "Diagnosis of *Clostridium diffi cile* infection by toxin detection kits: a systematic review" Lancet, 2008, vol. 8, pp. 777-784.
Pothoulakis et al. "Microbes and Microbial Toxins: Paradigms for Microbial-Mucosal Interactions II. The integrated response of the intestine to *Clostridium difficile* toxins" Am J Physiol Gastrintest Liver Physiol, 2001, vol. 280, pp. G178-G183.
Qa'Dan et al. "pH-Induced Conformational Changes in *Clostridium difficile* Toxin B" Infect Immun, 2000, vol. 68, pp. 2470-2474.
Ravetch et al. "IgG Fc Receptors" Ann Rev Immunol, 2001, vol. 19, pp. 275-290.
Reineke et al. "Autocatalytic cleavage of *Clostridium difficile* toxin B" Nature, 2007, vol. 446, pp. 415-419.
Ribeiro et al. Role of resident mast cells and macrophages in the neutrophil migration induced by LTB4,fMLP and C5a des arg, Int Arch Allergy Immunol, 1997, vol. 112, pp. 27-35.
Rupnik et al. "Characterization of the cleavage site and function of resulting cleavage fragments after limited proteolysis of *Clostridium difficile* toxin B (TcdB) by host cells" Microbiol, 2005, vol. 151, pp. 199-208.
Russmann et al. "Evaluation of three rapid assays for detection of *Clostridium difficile* toxin A and toxin B in stool specimens" Eur J Clin Microbiol Infect Dis, 2007, vol. 26, pp. 115-119. Sakurai et al. "Liver Abscess Caused by *Clostridium difficile*" Scan J Infect Dis, 2001, vol. 33, pp. 69-70.
Sapinoro et al. "Fc receptor-mediated, antibody-dependent enhancement of bacteriophage lambda-mediated gene transfer in mammalian cells" Virol, 2008, vol. 373, pp. 274-286.
Savidge et al. "*Clostridium difficile* Toxin B is an inflammatory Enterotixin in Human intestine" Gastroenterol, 2003, vol. 125, pp. 413-420.
Schirmer et al. "Large clostridial cytotoxins: cellular biology of Rho/Ras-glucosylating toxins" Biochim Biophys Acta, 2004, vol. 1673, pp. 66-74.
Sehr et al. "Glucosylation and ADP Ribosylation of Rho Proteins: Effects on Nucleotide Binding, GTPase Activity, and Effector Coupling†" Biochem, 1998, vol. 37, pp. 5296-5304.

(Continued)

*Primary Examiner* — Jennifer Graser
(74) *Attorney, Agent, or Firm* — Lawson & Weitzen, LLP; Sonia K. Guterman; Teofilo Javier, Jr.

(57) ABSTRACT

Cell-based methods for rapid real time assay of a presence of *Clostridium difficile* toxin and/or cells are provided, using an assay having a toxin-enhancing antibody and a sensitive cell line carrying FcγR receptors, and kits for this assay. An ultrasensitive cell based immunocytotoxicity assay for detecting less then 1 pg/ml of *C. difficile* toxins in clinical samples. A TcdA-specific monoclonal antibody, AIH3, was found to significantly enhance the cytotoxicity of TcdA to macrophages and monocytes. The AIH3-dependent enhancement of glucosyltransferase activity, cytoskeleton disruption, and TNF-a production induced by TcdA was demonstrated also in RAW 264.7 cells. Methods for high level recombinant expression of *C. difficile* toxins in *Bacillus* cells, and vectors for expression, strains of *Bacillus* carrying the vectors are provided.

13 Claims, 23 Drawing Sheets

OTHER PUBLICATIONS

Shin et al. "Emerging toxin A-B+ variant strain of *Clostridium difficile* responsible for pseudomembranous colitis at a tertiary care hospital in Korea" Diagn Microbiol Infect Dis, 2008, vol. 60, pp. 333-337.
Siemann et al. "*Clostridium difficile*-associated diseases" Inten Care Med, 2000, vol. 26, pp. 416-421.
Sougioultzis et al. "*Clostridium difficile* Toxoid vaccine in recurrent *C. difficile*-associated diarrhea" Gastroenterol, 2005, vol. 128, pp. 764-770.
Staneck et al. "Multicenter Evaluation of Four Methods for *Clostridium difficile* Detection: ImmunoCard *C. difficile*, Cytotoxin Assay, Culture, and Latex Agglutination" J Clin Microbiol, 1996, vol. 34, pp. 2718-2721.
Takada et al. "Antibody-dependent enhancement of viral infection: molecular mechanisms and in vivo implications" Rev Med Virol, 2003, vol. 13, pp. 387-398.
Tang-Feldman et al. "One-step cloning and expression of *Clostridium difficile* toxin B gene (tcdB)" Mol Cellul Probe, 2002, vol. 16, pp. 179-183.
Vary et al. "*Bacilius megaterium*—from simple soil bacterium to industrial protein production host" Appl Microbiol Biotechnol, 2007, vol. 76, pp. 957-967.
Voth et al. "*Clostridium difficile* Toxins: Mechanisms of Action and Role in Disease" Clin Microbiol Rev, 2005, vol. 18, pp. 247-263.
Wilkins et al. "*Clostridium difficile* Testing: after 20 Years, Still Challenging" J Clin Microbiol, 2003, vol. 41, pp. 531-534.
Yang et al. "Expression of recombinant *Clostridium difficile* toxin A and B in *Bacilius megaterium*" BMC Microbiol, 2008, vol. 8, pp. 192 (1-13).
Zhang et al. "Production and Characterization of Monoclonal Antibodies against *Enterocytozoon bieneusi* Purified from Rhesus Macaques" Infect Immun, 2005, vol. 73, pp. 5166-5172.
Abassi et al. "Label-free, real-time monitoring of IgE-mediated mast cell activation on microelectronic cell sensor arrays" 2004, J Immunol Method, vol. 292, pp. 195-205.
Babock et al."Human Monoclonal Antibodies Directed against Toxins A and B Prevent *Clostridium difficile*-Induced Mortality in Hamsters" 2006, Infect Immun, vol. 74, pp. 6339-6347.
Bartlett et al. "Antibiotic-Associated Diarrhea" 2002, vol. 346, pp. 334-339.
Bartlett et al. "Narrative Review: The New Epidemic of *Clostridium difficile*-Associated Enteric Disease" Ann Intern Med, vol. 145, pp. 758-764, 2004.
Brito et al. "Mechanism of *Clostridium difficile* Toxin A-Induced Apoptosis in T84 Cells" J Infect Dis, 2002, vol. 186, pp. 1438-1447.
Burger et al. "Expression of recombinant *Clostridium difficile* toxin A using the *Bacillus megaterium* system"Biochem Biophys Res Commun, 2003, vol. 307, pp. 584-588.
Chang et al. "Cytotoxicity Assay in Antiobiotic-Associated Colitis" J Infect Dis, 1979, vol. 140, pp. 765-770.
Cho et al. "A new multivalent B cell activation model—anti-IgD bound to FcgRI: properties and comparison with CD40L-mediated activation" Int Immunol, 1997, vol. 9, pp. 239-248.
Cloud et al. "Update on *Clostridium difficile* associated disease" Curr Opin Gastroenterol, 2007, vol. 23, pp. 4-9.
Cunney et al. "*Clostridium difficile* colitis associated with chronic renal failure" Nephrol Dial Transplant, 1998, vol. 13, pp. 2842-2846.
Daeron "Fc Receptor Biology" Annu Rev Immunol, vol. 15, pp. 203-234, 2002.
Dobson et al. "*Clostridium difficile* colitis causing toxic megacolon, severe sepsis and multiple organ dysfunction syndrome" Inten Care Med, 2003, vol. 29, p. 1030.
Egerer et al. "Auto-catalytic Cleavage of *Clostridium difficile* Toxins A and B Depends on Cysteine Protease Activity" J Biol Chem, 2007, vol. 282, pp. 25314-25321.
Feng et al. "Stressed apoptotic tumor cells express heat shock proteins and elicit tumor-specific immunity" Blood, 2001, vol. 97, pp. 3505-3512.
Feng et al. "Listeria-Infected Myeloid Dendritic Cells Produce IFN-Beta, Priming T Cell Activation" J Immunol, 2005, vol. 175, pp. 421-432.
Genth et al. "Cellular stability of Rho-GTPases glucosylated by *Clostridium difficile* toxin B" FEBS Lett,2006, vol. 580, pp. 3565-3569.
Gerhard et al. "Comparison of wild type with recombinant *Clostridium difficile* toxin A" Microbial Pathogen, 2005, vol. 38, pp. 77-83.
Giesemann et al. "Cholesterol-dependent Pore Formation of *Clostridium difficile* Toxin A" J Biol Chem, 2006, vol. 281, pp. 10808-10815.
Hamm et al. "Identification of *Clostridium difficile* toxin B cardiotoxicity using a zebrafish embryo model of intoxication" Proc Natl Acad Sci, 2006, vol. 103, pp. 14176-14181.
He et al. "Antibody-Enhanced, Fc Gamma Receptor-Mediated Endocytosis of *Clostridium difficile* Toxin A" Infect Immun, 2009, vol. 77, pp. 2294-2303.
He et al. "An ultrasensitive rapid immunocytotoxicity assay for detecting *Clostridium difficile* toxins" J Microbol Method, 2009, vol. 78, pp. 97-100.
Huang et al. "Differential kinase requirements in human and mouse Fcgamma receptor phagocytosis and endocytosis" J Leukocyte Biol, vol. 80, pp. 1553-1562, 2003.
Jacob et al. "*Clostridium difficile* and acute respiratory distress syndrome" Heart Lung, 2004, vol. 33, pp. 265-268.
Jank et al. "Structure and mode of action of clostridial glucosylating toxins: the ABCD model" Trend Microbiol, 2008, vol. 16, pp. 222-229.
Jefferson et al. "Roles of Intracellular Calcium and NF-kB in the *Clostridium difficile* Toxin A-Induced Up-Regulation and Secretion IL-8 from Human Monocytes1" J Immunol, 1999, vol. 163, pp. 5183-5191.
Johnson et al. "Fatal Pseudomembranous Colitis Associated with a Variant *Clostridium difficile* Strain Not Detected by Toxin A Immunoassay" Ann Intern Med, 2001, vol. 135, pp. 434-438.
Just et al. "Large clostridial cyctotoxins" Rev Physiol Biochem Pharmacol, 2004, vol. 152, pp. 23-47.
Katchar et al. "Association between IgG2 and IgG3 subclass responses to Toxin A recurrent *Clostridium difficile*-associated disease" Clin Gastroenterol Hepatol, 2007, vol. 5, pp. 707-713.
Keel et al. "The Distribution and Density of *Clostridium difficile* Toxin Receptors on the Intestinal Mucosa of Neonatal Pigs" Vet Pathol, 2007, vol. 44, pp. 814-822.
Kelly et al. "*Clostridium difficile* infection" Annu Rev Med, 1998, vol. 49, pp. 375-390.
Kelly et al. "*Clostridium difficile*—More diffiult than ever" New Eng J Med, 2008, vol. 359, pp. 1932-1940.
Kikkawa et al. "Prevalence of toxin A-nonproducing/toxin-B-producing *Clostridium difficile* in the Tsukaba-Tsuchiura district, Japan" J Infect Chemother, 2007, vol. 13, pp. 35-38.
Kim et al. "*Clostridium difficile* Toxin A-Induced Colonocyte Apoptosis Involves p53-dependent p21 (WAF1/CIP1) induction via p38 mitogen-activated protein kinase" Gastroenterol, 2005, vol. 129, vol. 1875-1888.
Krakowka et al. "Establishment of Gastric *Campylobacter pylori* Infection in the Neonatal Gnotobiotic Piglet" Infect Immun, 1987, vol. 55, pp. 2789-2796.
Kuijper et al. "*Clostridium difficile*: changing epidemiology and new treatment options" Curr Opin Infect Dis, 2007, vol. 20, pp. 376-383.
Kurtz et al. "GT160-246, a Toxin Binding Polymer for Treatment of *Clostridium difficile* Colitis" Antimicrobial Agent Chemother 2001, vol. 45, pp. 2340-2347.
Kyne et al. "Asymptomatic Carriage of *Clostridium Difficile* and Serum Levelsof IgG Antibody Against Toxin A" New Engl J Med, 2000, vol. 342, pp. 390-397.
Kyne et al. "Association between antibody response to toxin A and protection against recurrent *Clostridium difficile* diarrhoea" LANCET, 2001, vol. 357, pp. 189-193.
Kyne et al. "Health Care Costs and Mortality Associated with Nosocomial Diarrhea Due to *Clostridium difficile*" Clin Infect Dis, 2002, vol. 34, pp. 346-353.

Leopold et al. "Neutralized Adenovirus-Immune Complexes Can Mediate Effective Gene Transfer via an Fc Receptor-Dependent Infection Pathway" J Viral, 2006, vol. 80, pp. 10237-10247.

Leung et al. "Treatment with intravenously administered gamma globulin of chronic relapsing colitis induced by *Clostridium difficile* toxin" J Pediatr, 1991, vol. 118, pp. 633-637.

Loo et al. "A Predominantly Clonal Multi-Institutional Outbreak of *Clostridium difficile*-Associated Diarrhea with High Morbidity and Mortality" New Eng J Med, 2005, vol. 353, pp. 2442-2449.

Makoff et al. "Expression of tetanus toxin fragnent C in *E. coli*: high level expression by removing rare codons" Nucl Acid Res, 1989, vol. 17, pp. 10191-10202.

Malten et al. "A *Bacillus megaterium* Plasmid System for the Production, Export, and One-Step Purification of Affinity-Tagged Heterologous Levansucrase from Growth Medium†" Appl Environment Microbiol, 2006, vol. 72, pp. 1677-1679.

Matarrese et al. "*Clostridium difficile* Toxin B Causes Apoptosis in Epithelial Cells by Thrilling Mitochondria" J Biol Chem, 2007, vol. 282, pp. 9029-9041.

McDonald et al. "An Epidemic, Toxin Gene-Variant Strain of *Clostridium difficile*" New Engl J Med, 2005, vol. 353, pp. 2433-2441.

McFarland et al. "Nosocomial acquisition *Clostridium difficile* infection" New Engl J Med, 1989, vol. 320, pp. 204-210.

Mukherjee et al. "Endocytosis" Physioi Rev, 1997, vol. 77, 759-803.

Na et al. "gp96 Is a Human Colonocyte Plasma Membrane Binding Protein for *Clostridium difficile* Toxin A" Infect Immun, 2008, vol. 76, pp. 2862-2871.

Norman et al. "Endocytosis of FcQRI is regulated by two distinct signalling pathways" FEBS Lett, 2000, vol. 484, pp. 179-183.

Asphahani et al. "Cellular impedance biosensors for drug screening and toxin detection" Analyst, 2007, vol. 132, pp. 835-841.
Mohamed et al. "Enhancement of Anthrax Lethal Toxin Cytotoxicity: a Subset of Monoclonal Antibodies against Protective Antigen Increases Lethal Toxin-Mediated Killing of Murine Macrophages" Infect Immun, 2004, vol. 72, pp. 3276-3283.

* cited by examiner

MEDIUM

TcdA 50ng/ml

TcdA 0.4ng/ml

A1H3 + TcdA 0.4ng/ml

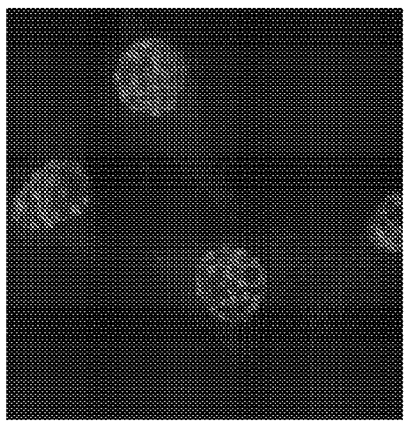
Fig. 8B — A1H3 ALONE 37°C
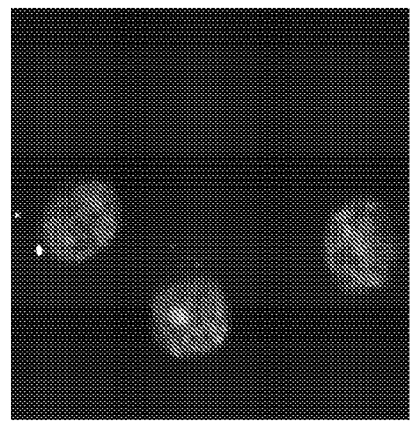
Fig. 8C — A1E6 + TcdA, 37°C
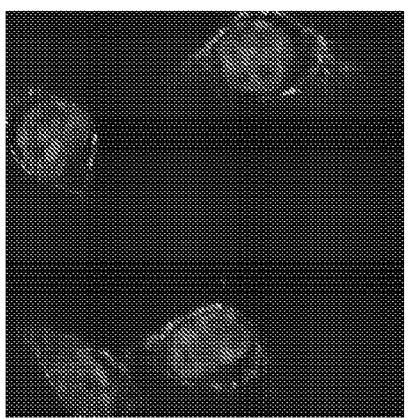
Fig. 8D — A1H3 + TcdA, 4°C
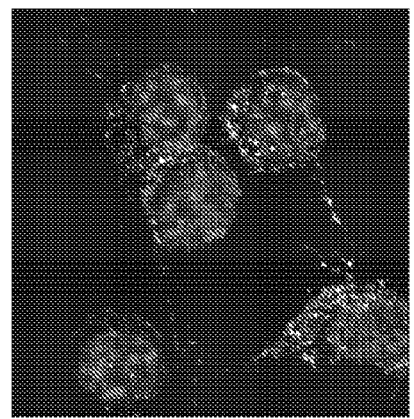
Fig. 8E — A1H3 + TcdA, 37°C TcdA (10 ng/ml)

TcdA (10 ng/ml) + A1H3

TcdA (10 ng/ml)

TcdA (10 ng/ml) + A1H3

MEDIUM

SUPERNATANT

SUPERNATANT

SUPERNATANT rTcdB (ng/ml)
1 nTcdB (ng/ml)
1 rTcdB (ng/ml)
10 nTcdB (ng/ml)
10 rTcdA (ng/ml)
20 nTcdA (ng/ml)
20 rTcdA (ng/ml)
200 nTcdA (ng/ml)
200 rTcdA (ng/ml)
200 + pAb nTcdA (ng/ml)
200 + pAb rTcdB 2 hr rTcdB 4 hr

METHODS FOR DIAGNOSIS OF *CLOSTRIDIUM DIFFICILE* AND METHODS AND VECTORS FOR RECOMBINANT TOXIN EXPRESSION

RELATED APPLICATIONS

The present application claims the benefit of U.S. provisional application Ser. No. 61/127,757, inventors Saul Tzipori, Hanping Feng and Guilin Yang filed May 15, 2008 in the U.S. Patent and Trademark Office, and International application serial number PCT/US2009/03055, filed May 15, 2009, each of which is incorporated herein by reference in its entirety.

GOVERNMENT SUPPORT

The present invention was supported in part by grants NIH N01 AI030050 and NIH K01 DK076549 from the National Institutes of Health. The government has certain rights in the invention.

TECHNICAL FIELD

Methods and kits for assay of presence of *Clostridium difficile* cells and toxins and methods and vectors for recombinant production of the toxins are provided.

BACKGROUND

*Clostridium difficile* is a Gram positive, spore forming anaerobic *bacillus*, and many strains of this species have acquired resistance to a majority of commonly used antibiotics. The reduction of commensal microflora as an effect of use of antibiotics allows *C. difficile* to grow and to produce harmful toxins in the intestine, without nutritional competition from normal bacterial flora. Transmitted primarily through contact with contaminated surfaces, *C. difficile* is a common cause of nosocomial antibiotics-associated diarrhea (CDAD) and pseudodomembranous colitis. (Cloud, J. et al. 2007 Cur Opin Gastroenterol 23:4-9). Infection caused by *C. difficile* accounts for millions of patient cases and billions of dollars yearly in treatment in hospitals, nursing homes and other care centers. (O'Brien, et al. November 2007 Infection Control and Hospital Epidemiology 28(11): 1219-1227). Highly virulent strains of *C. difficile* result in increased incidence of illness and more severe effects in patients. (McDonald, et al. 2005 N Engl J Med. 353:2466-2441).

The diagnosis of *C. difficile* infection remains a challenge (Wilkins T D et al. 2003 J Clin Microbiol 41:531-4). The current diagnostic modalities mainly consist of the detection of the *C. difficile* organisms and of their toxins in fecal samples. Isolation of *C. difficile* from stool culture is seldom carried out clinically because it is labor-intensive and time-consuming (Bartlett J G. 2006 Ann Intern Med 145:758-64). One method commonly used is the detection of the enzyme glutamate dehydrogenase (GDH) of *C. difficile*, but this approach cannot distinguish the toxigenic strains from non-toxigenic ones. Other methods, such as real-time PCR for detecting bacterial genes, are under evaluation for the diagnosis of *C. difficile*-associated disease (Peterson L R et al. 2007 Clin Infect Dis 45:1152-60), but require sophisticated equipment and training. These assays, which detect the organism, are associated with an inherent problem in that 10% to 30% of hospitalized patients are colonized with toxigenic or non-toxigenic *C. difficile* without disease (McFarland L V et al. 1989 N Engl J Med 320:204-10). It is therefore more desirable to detect toxins which are thought to be the cause of *C. difficile*-associated diarrhea (CDAD) (Kelly C P et al. 2008 N Engl J Med 359:1932-40). The widely used enzyme immunoassays (EIAs) are based on monoclonal antibodies (MAbs) that recognize TcdA and/or TcdB. EIAs are rapid and easy, but suffer from low to moderate sensitivity (Planche T et al. 2008 Lancet Infect Dis (12):777-84). The cytotoxin B assay is the "gold standard" for the laboratory diagnosis of *C. difficile* infection due to its high sensitivity and specificity (Chang T W et al. 1979 J Infect Dis 140:765-70). The assay mainly detects the presence of TcdB, which is far more potent than TcdA in causing cytopathic changes in cultured cells. The drawbacks of cytotoxin B assay are technical complexity, slow turnaround time (24-72 h) and the requirement for a cell culture facility (Chang T W et al. 1979 J Infect Dis 140:765-70). Given the dramatic increase of cases and severity of CDAD in recent years, a rapid and easy to perform assay with high sensitivity and specificity for the diagnosis of *C. difficile* infection is an urgent need.

*C. difficile* produces two major protein toxins, toxin A (TcdA) and toxin B (TcdB), which are 308 kD and 269 kD respectively in size. (U.S. Pat. No. 5,098,826, Wilkins et al., issued Mar. 24, 1992). The two toxins belong to the large clostridial cytotoxin (LCT) family and share 49% amino acid identity. (Just, I. et al. 2004 Reviews of physiology, biochemistry and pharmacology 152:23-47). The toxins have similar structures and share putative receptor binding, transmembrane, and enzymatic domains. (Schirmer, J. et al. 2004 Biochimica et Biophysica acta 1673:66-74). After receptor-mediated internalization and intracellular cleavage, the toxins glucosylate members of the Rho-Rac family of small GTPases at a specific threonine residue in host intestinal epithelial cells, leading to alterations in the actin cytoskeleton, massive fluid secretion, acute inflammation, and necrosis of the colonic mucosa. TcdA is an enterotoxin and has minimal cytotoxic activity, whereas TcdB is a potent cytotoxin with limited enterotoxic activity in animals. The extensive damage to the intestinal mucosa was thought to be primarily attributable to the action of TcdA. However, TcdA and TcdB were found to act synergistically in the intestine. (U.S. Pat. No. 6,939,548, Wilkins et al., issued Sep. 6, 2005).

Currently, *C. difficile* toxins have heretofore been purified mainly from culture supernatants of toxigenic bacteria; the process presents a number of problems including cumbersome purification methods and the presence of contaminants in the resulting proteins. Production of recombinant *C. difficile* toxins in *Escherichia coli* have been attempted without success. Assays for detection of *C. difficile* are currently commercially available, including antigenic detection of a common bacterial enzyme, glutamate dehydrogenase (GDH), a method that does not differentiate between toxigenic and non-toxigenic strains. Enzyme Immunoassays (EIAs) for detecting TcdA and/or TcdB in stool samples are widely used. However, many immunoassay kits have limited sensitivity or are capable of detecting only one of the toxins. (Novak-Weekly, S. M. et al. 2008 Clin Vaccine Immunol; Russman, H. et al. 2007 Eur J Clin Microbiol Infect Dis 26(2): p. 115-9; Staneck, J. L. et al. 1996 J. Clin Microbiol. 34(11): p. 2718-21; Whittier, S. et al. J. Clin Microbiol. 31(11): p. 2861-5; Barbut, F., et al. J Clin Microbiol. 31(4): p. 963-7). Disadvantages of the cytotoxin B assay (CBA) that detects TcdB include technical complexity and slow turnaround time, restrict routine clinical use of the assay for diagnosis. Further, sensitivity of CBA for TcdA is very low.

The growing incidence and severity of *C. difficile* indicate a need for better understanding of pathogenesis in patients, and development of new assay and treatment tools and methods to obtain relatively pure and biologically active TcdA and TcdB for research. It is desirable to obtain relatively pure and biologically active TcdA and TcdB for studying the pathogenesis of CDAD and host immune response to the infection and for generating immunological tools for research and clinical diagnosis. The native toxins are usually purified from toxigenic *C. difficile* culture supernatant, which involves multiple steps and the purity is often unsatisfactory (Krivan H C et al. 1987 Infect Immun 55(8):1873-1877; Sullivan N M et al. 1982 Infect Immun 35(3):1032-1040; Keel M K et al. 2007 Veterinary pathology 44(6):814-822). Attempts have been made to clone and express *C. difficile* toxins in *Escherichia coli* (Phelps C J et al. 1991 Infection and immunity 59(1): 150-153; Tang-Feldman Y J et al. 2002 Molecular and cellular probes 16(3):179-183; Wren B W et al. 1987 FEBS letters 225(1-2):82-86), but it is unclear whether or not purified toxins were obtained from the bacterial lysate in these studies. The Gram-positive *Bacillus megaterium* expression system may offer an alternative for the expression of *C. difficile* toxins due to several advantages over the *E. coli* system, including the lack of alkaline proteases activity and endotoxin liposaccharides (LPS), and the ability to secrete expressed heterologous protein into the medium (Malten M et al. 2006 Applied and environmental microbiology 72(2):1677-1679; Vary P S et al. 2007 Applied microbiology and biotechnology 76(5):957-967). Burger et al. expressed purified recombinant TcdA in *B. megaterium* however obtained only low levels of expression (Burger S et al. 2003 Biochem Biophys Res Commun 307(3):584-588)). In examples herein full-length proteins of both TcdA and TcdB in *B. megaterium* were expressed, and an average of 5-10 mg of highly purified recombinant proteins from one liter of total bacterial culture was obtained. Both recombinant TcdA and TcdB were biologically active similar to their native purified toxins.

SUMMARY

An aspect of the invention herein provides a method for detecting a presence of *Clostridium difficile* toxin and/or toxigenic *C. difficile* in a biological sample, the method including: contacting a first set of test cells with an aliquot of the sample and an amount of a toxin-enhancing antibody; and measuring cell death in the first set of test cells in comparison with a second set of the test cells not so contacted and otherwise identical as a negative control, such that an extent of test cell death in the first set in comparison to the second set indicates the presence of *Clostridium difficile* toxin and/or toxigenic *C. difficile* in the sample.

In related embodiments, the method further involves contacting at least a third set of test cells with at least one known amount of *C. difficile* toxin as a positive control. The method according to related embodiments further involves contacting at least a fourth set of test cells with a different known amount of *C. difficile* toxin such that a plurality of positive controls includes a standard curve for toxin killing in the presence of the toxin-enhancing antibody.

In various embodiments of the methods herein, measuring the cell death includes measuring at least one selected from the group of: decrease in respiration by a tetrazolium dye, increase in cell rounding, increase in glucosylation of Rac1, increase in cytoskeleton disruption, increase in necrosis, increase in endocytosis of antibody-toxin, increase in apoptosis, and decrease in cell attachment to a surface by electronic sensing of resistance or impedance.

In general, the test cells are white blood cells or colonic epithelial cells. In various embodiments of the methods above, the white blood cells are macrophages, for example mouse RAW264.7 cells. Alternatively, the cells are produced by Chinese Hamster Ovary (CHO) cell lines, human acute monocytic leukemia cell line (THP1), or Meis homeobox 2 (MRG1) gene. In various embodiments of the methods herein, the test cells include an IgG Fc gamma receptor (FcγR).

In various embodiments of the methods herein, the toxin-enhancing antibody is specific for an epitope of *C. difficile* toxin protein selected from the group of TcdA and TcdB. In related embodiments the toxin-enhancing antibody has an IgG2a isotype. In general the toxin-enhancing antibody is A1H3 or PCG4.1.

In various embodiments of the methods herein, the method further involves detecting, in a milliliter of the sample, toxin that is less than about fifty picograms, less than about 10 picograms, less than about 5 picograms, or less than about one picogram.

In general, measuring cell attachment by resistance or impedance is measuring real-time cell electronic sensing (RT-CES) in a multi-cell culture dish or E-plate.

In related embodiments of the methods herein, the test cells are at least one selected from the group consisting of: frozen cells defrosted cells that are contacted absent culturing, frozen cells that are defrosted and are cultured prior to use, and primary or cultured cells that are fresh.

In general, the method further involves analyzing cell death data from the first and second sets of cells and optionally from the standard curve, such that the steps of contacting, measuring, and analyzing are accomplished in less than about 24 hours, less than about eight hours, less than about six hours, or less than about three hours.

Various embodiments of the methods herein further involve identifying the presence of the toxin with a neutralizing antibody or an anti-toxin that binds at least one *C. difficile* toxin, such that prior to contacting, the method involves pre-mixing the sample and neutralizing antibody and that the neutralizing antibody reduces extent of cell death of test cells further indicates a presence of a *C. difficile* toxin infection.

Another aspect of the invention herein provides a method of producing a clostridial toxin in a *Bacillus* host, the method involving: contacting a cell of a *Bacillus* species with a nucleic acid vector carrying: a gene encoding a *Clostridium* toxin protein, the gene operably linked to a regulatory signal for controlling expression of the gene in the cell, such that the gene is further engineered as a recombinant nucleic acid fusion encoding a *Bacillus* signal sequence linked in the same reading frame as the toxin, the vector further carrying a selectable marker, to selectively obtain resulting transformants for carrying the vector; screening a plurality of selected transformants for expression of toxin to obtain a transformant *Bacillus* host strain secreting the recombinant toxin; and expressing and secreting the recombinant toxin in a culture the *Bacillus* strain, thereby producing the toxin.

In general, the *Bacillus* is *B. megaterium* and the *Clostridium* is *C. difficile*. In various embodiments of the method, the *Bacillus* signal sequence is a 28-amino acid peptide of *B. megaterium* extracellular esterase LipA. In related embodiments of the method, the gene is obtained by polymerase chain reaction.

In various embodiments of the methods herein, the vector further comprises an affinity marker as a fusion to the toxin. In related embodiments of the method, the affinity marker is selected from a poly-histidine and an amino acid sequence that binds to biotin or Streptactin, for example an avidin, an streptavidin, or a streptag. Alternatively, the method involves using any of the affinity tags or affinity markers that are presently known in the art.

In related embodiments of methods herein, screening the plurality of transformants further involves contacting mammalian test cells with a supernatant or a cell extract from each transformant and assaying contacted cells for cell rounding in comparison to tests cells not so contacted.

In general, expressing and secreting the recombinant toxin genes produces an amount of toxin at least an order of magnitude greater than that found in wild type clostridia, or at least two orders or three orders magnitude greater. In various embodiments of the method, the vector is a shuttle vector that replicates in a *Bacillus* and in another prokaryotic species or genus. In a related embodiments of the methods herein, the vector replicates in *Escherichia coli* as well as in *B. megatarium*.

Another aspect of the invention herein provides a vector including a BsrG1 cloning site for the amino terminus of the coding region of the gene. In related embodiments, the vector expressing a *C. difficile* toxin in a *Bacillus* cell, such that a gene encoding the toxin is recombinantly ligated at a BrsG1 restriction site in the vector, wherein the amino terminus of the toxin protein is located at the site. Another embodiment of the invention is a cell carrying any of the vectors, herein.

Another aspect of the invention herein provides a kit for assaying presence of a *C. difficile* toxin or cell including: a toxin-enhancing antibody, a toxin positive control, and a container. In related embodiments, the kit further includes instructions for use. In related embodiments, the kit further includes a toxin-neutralizing antibody that specifically binds at least one of *C. difficile* TcdA and TcdB, as a positive identifying control.

BRIEF DESCRIPTION OF THE DRAWINGS

FIG. 1 panel A shows data using mRG1-1 test cells seeded on 16-well E-plates at the 0 h time point. After an overnight culture, the test cells were exposed to the indicated amount of toxin in the absence or presence of A1H3 (H3). The control groups included the test cells with PBS, rabbit antiserum, or A1H3 alone. Serum blocking was determined using rabbit-anti-TcdA serum (pAb) which was mixed with the toxin and A1H3 and then added to the cells.

FIG. 1 panel B shows data using freshly thawed mRG1-1 test cells seeded on 16-well E-plates simultaneously with a mixture of an indicated amount of TcdA or TcdB in the absence or presence of A1H3 (H3). Serum blocking was determined using goat anti-TcdB serum (polyAb) which was mixed with the toxin and A1H3 and then added to the cells. The dynamic changes in cell index (CI) were recorded by RT-CES at 15-min intervals. The data shown are from the representative experiments.

FIG. 2 panel A shows test cells that were mixed with diluted (100 or 1000 times) fecal samples taken from *C. difficile* pre-(F-N) or post-(F-P) inoculated gnotobiotic piglets (n=12), tested in the presence or absence of A1H3.

FIG. 2 panels B and C show data from serum or pleural effusion from severely infected piglets (n=5) that were diluted with PBS (final dilution 30 times) and then mixed with the freshly thawed mRG1-1 test cells with or without A1H3 (H3). Serum sample from piglet #7 is shown in FIG. 2 panel B. Serum and pleural effusion (PE) samples from piglet #11 are shown in FIG. 2 panel C. In the serum blocking tests, goat antiserum against both TcdA and TcdB (polyAb) was mixed with the samples and mRG1-1 test cells, and then added into E-plate. The dynamic changes of CI were recorded by RT-CES. The data shown here are from the representative specimens.

FIG. 3 panel A RAW 264.7 test cells were cultured with various doses of TcdA (▲), or with TcdA complexed with anti-TcdA MAb A1E6 (Δ), A1H3 (■), or a control unrelated JF1 antibody (□).

FIG. 3 panel B THP1 test cells were cultured with TcdA (■), or with TcdA complexed with A1H3 (▲). After two days of incubation, cytotoxicity was measured with a MTT assay. Cell survival was expressed as percentage of the control group (100%).

FIG. 4 panel A shows data from RAW 264.7 test cells that were treated with TcdA (0.4 ng/ml) in the presence of the indicated doses of A1H3 for 4 h.

FIG. 4 panel B shows data from RAW 264.7 test cells that were incubated with TcdA (0.4 ng/ml) with or without the indicated MAbs for the time shown.

FIG. 4 panel C shows data from THP1 test cells that were incubated with various doses of TcdA with or without A1H3 for 4 h.

FIG. 4 panel D shows data from mouse peritoneal exudate macrophages that were exposed to the indicated amount of TcdA with or without A1H3 for 5 h.

FIG. 7 panel F shows data from CHO cells treated with TcdA (A upper line) or TcdA/A1H3 complex (□ upper line), or mGR1-1 cells incubated with TcdA (A bottom line) or TcdA/A1H3 complex with (◇) or without (□ bottom line) rabbit anti-TcdA polyclonal antibodies (pAb) for 2 days. Cytotoxic effects were then measured by MTT assay. Cell survival was expressed as percentage of the control group (100%).

FIG. 8 panel A shows data from RAW 264.7 cells that were incubated on ice for 30 min with A1H3, TcdA (10 ng/ml)/A1H3 or TcdA/A1E6. The binding of anti-TcdA MAbs was determined by PE-conjugated anti-mouse-Ig antibody staining and FACS analysis. Subconfluent RAW 264.7 test cells on coverslips were incubated for 30 min with A1H3 (FIG. 8 panel B), TcdA (1 ng/ml)/A1E6 (FIG. 8 panel C) at 37° C., TcdA/A1H3 at 4° C. (FIG. 8 panel D) or TcdA/A1H3 at 37° C. (FIG. 8 panel E). Cells were fixed and stained with Alexa-488-conjugated anti-mouse-Ig antibodies and DAPI. The binding and internalization of A1H3 was examined by confocal microscopy.

FIG. 10 panel A shows RAW 264.7 cells that were pre-incubated with chlorpromazine (CPZ), ammonium chloride ($NH_4Cl$), or chloroquine (CQ) at the indicated amounts for 30 min before the addition of TcdA (0.4 ng/ml) with or without A1H3. Rac1 glucosylation was determined by Western blotting.

FIG. 10 panel B shows RAW264.7 cells that were pre-incubated with CPZ (5 μg/ml) or CQ (0.1 mM) for 30 min before the addition of TcdA (0.4 ng/ml)/A1H3 immune complex.

FIG. 10 panel C shows RAW264.7 cells that were pre-incubated $NH_4Cl$ (20 mM) for 30 mM before addition of TcdA (0.4 ng/ml)/A1H3 immune complex or LPS (1 μg/ml). Cells treated with medium alone, TcdA (0.4 ng/ml) alone, or TcdA complexed with A1H3 served as controls. TNF-α production was determined by intracellular cytokine staining. The R3 region shows TNF-α negative cells and R2 represents the percentage of TNF-α positive cells.

FIG. 11 panel A shows data from His-tag affinity purification of total lysate from B. megaterium. Lane 1: total bacterial lysate; Lane 2: flow-through; Lane 3: wash; lane 4-6: elution fraction 1-3.

FIG. 11 panel B shows data from anion-exchange column fractionation after Ni-affinity chromatography. nTcdB: purified native TcdB from C. difficile culture supernatant. Lane 1: Elution fraction 2 from FIG. 11 panel A; Lane 2-8: fractions from a gradient salt elution. Fraction 5 and 6 contain purified rTcdB.

FIG. 11 panel C shows Western blot results of purified native TcdB and rTcdB of combined fractions 5 and 6 from FIG. 11 panel B.

FIG. 11 panel D shows Coomassie staining of SDS-PAGE from each of a total sonicate lysates of a pHis-TcdB transformed clone (lane 1), concentrated supernatant from a pHis-SP-TcdB transformed clone (Lane 2) and purified native TcdB (Lane 3).

FIG. 12. panel A shows Coomassie staining of SDS-PAGE from crude bacterial extracts: lane 1 is a control with no xylose induction; lanes 2 to 4 show results from three different clones with xylose induction; lane 5 shows purified rTcdA after Ni-affinity and thyroglobulin chromatograph. M shows molecular weight marker and the top band indicates 250 kDa.

FIG. 12. panel B shows Western blot results for purified native TcdA (Lane 1, left) and rTcdA (Lane 2, right).

FIG. 15 panel C shows data from CT26 cells that were pretreated with ammonium chloride for 30 min before exposure to the indicated amount of recombinant toxins for 5 h. Cells were harvested and Western blot was performed as described in examples herein. Monoclonal antibody clone 102 recognizes unglucosylated Rac1 and has reduced affinity to glucosylated Rac1.

DETAILED DESCRIPTION

Figure 1A:
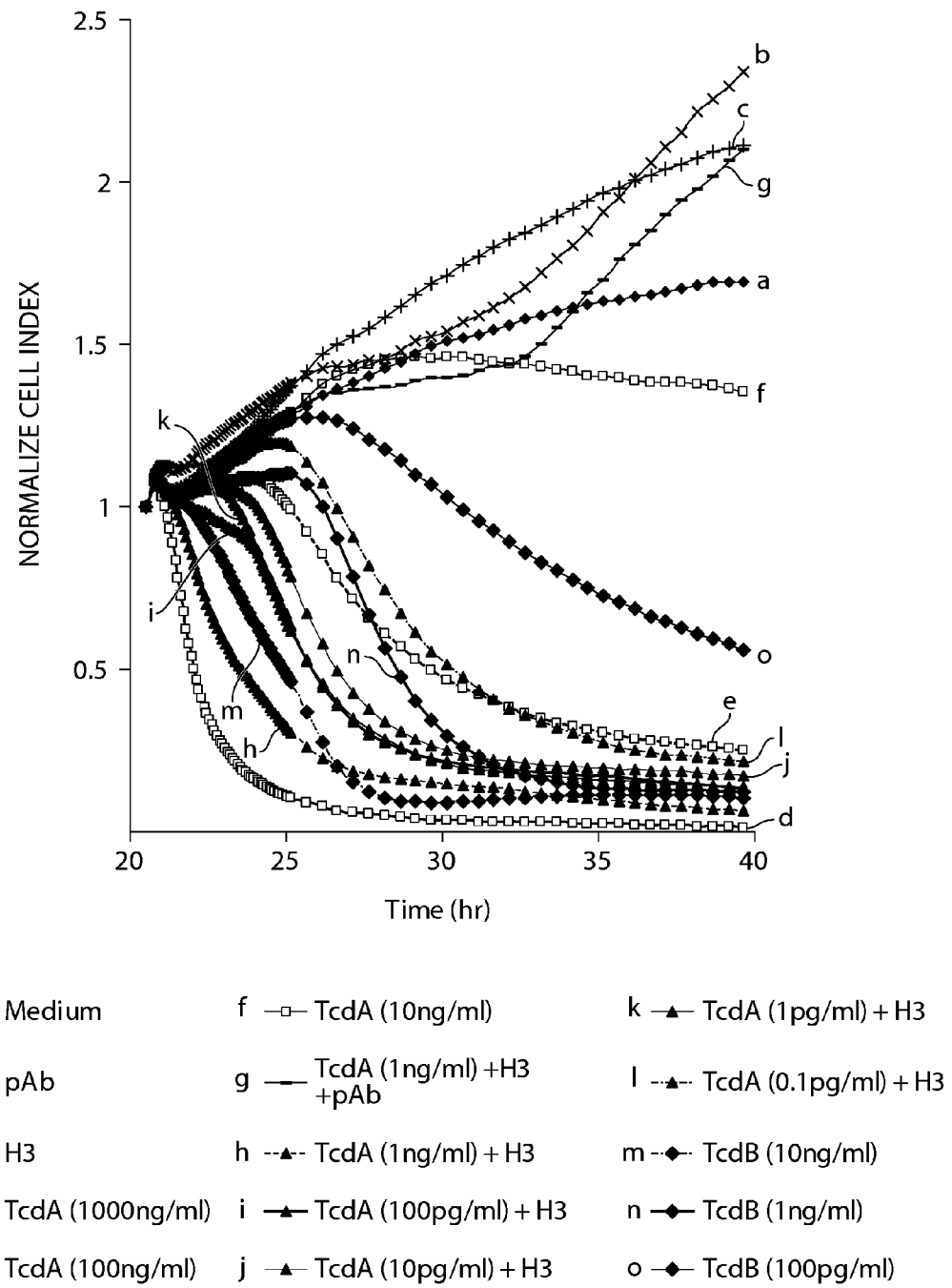
FIG. 1 is a set of line graphs showing real-time monitoring of cytotoxic effects of *C. difficile* toxins on mRG1-1 using RT-CES system.

*C. difficile* is a gram-positive, spore forming, anaerobic bacterium. It is the leading cause of antibiotic-associated diarrhea, the severity which ranges from mild diarrhea to life threatening pseudomembranous colitis (Bartlett J G. 2002 N Engl J Med 346:334-9). Pathogenic *C. difficile* strains excrete exotoxins A (TcdA) and B (TcdB) that have been intimately linked to its pathogenicity. Both TcdA and TcdB are enterotoxic, capable of inducing intestinal epithelial damage and increasing mucosal permeability, and hence are thought to be responsible for the pathogenesis of *C. difficile*-associated colitis (Kelly C P et al. 1998 Annu Rev Med 49:375-90). *C. difficile* has emerged as a leading cause of hospital-acquired enteric infections with rapidly escalating annual health care costs in the United States (Kyne L et al. 2002 Clin Infect Dis 34:346-353). The severity of *C. difficile*-associated infections ranges from mild diarrhea to life threatening pseudomembranous colitis (Bartlett J G et al. 2002 N Engl J Med 346:334-339; Borriello S P 1998 Antimicrob Chemother 41 Suppl C:13-19). Several hospital outbreaks of *C. difficile*-associated diarrhea (CDAD), with high morbidity and mortality in the past few years in North America, have been attributed to the widespread use of broad-spectrum antibiotics. The emergence of more virulent *C. difficile* strains is also contributing to the increased incidence and severity of the disease (Loo V G et al. 2005 N Engl J Med 353:2442-2449; McDonald L C et al. 2005 N Engl J Med 353:2433-2441). Antibiotic usage results in a reduction of commensal microflora in the gut, which permits *C. difficile* to proliferate more extensively, leading to the production of toxins (Owens J R et al. 2008 Clinical Infectious Diseases 46(s1):S19-S31). *C. difficile* associated diarrhea (CDAD) includes a range of symptoms varying from mild diarrhea to severe fulminate lethal disease (Kuijper E J et al. 2007 Curr Opin Infect Dis 20(4):376-383). Recent outbreaks of highly virulent *C. difficile* strains (McDonald L C et al. 2005 N Engl J Med 353(23):2433-2441; Loo V G et al. 2005 N Engl J Med 353(23):2442-2449) have increased the urgency to devote greater resources towards the understanding of the molecular, genetic, and biochemical basis for the pathogenesis, with a view to use such information to develop novel preventive and treatment modalities.

A cell-based immunocytotoxicity assay for detecting *C. difficile* toxins is described herein, that uses an anti-*C. difficile* toxin A (TcdA) monoclonal antibody, named A1H3, which substantially enhanced the activity of TcdA on Fc gamma receptor I (FcγRI)-expressing cells (He X, Sun X, Wang J, et al. Antibody-enhanced, Fc{gamma}R-mediated endocytosis of *C. difficile* toxin A. Infect Immun 2009). A1H3 enhancing antibody, in combination with an electronic sensing system was used to develop a real-time and ultrasensitive assay for the detection of biological activity of *C. difficile* toxins. The assay was easy-to-perform and particularly sensitive for TcdA, detecting this toxin, at a level of 0.1 pg/ml to 1 pg/ml, and required a short turnaround time of about 3 h.

Toxin A (TcdA) and toxin B (TcdB) are the two major virulence factors contributing to pathogenic *C. difficile* strains. They are enterotoxic, inducing intestinal epithelial cell damage, disrupting epithelium tight junctions leading to increased mucosal permeability (Pothoulakis C et al. 2001 Am J Physiol Gastrointest Liver Physiol 280:G178-183; Riegler M et al. 1995 J Clin Invest 95:2004-2011; Savidge T C et al. 2003 Gastroenterology 125:413-420). Moreover, these toxins induce production of immune mediators, leading to subsequent neutrophil infiltration and severe colitis (Kelly C P et al. 1994 J Clin Invest 93:1257-1265; Kelly C P et al. 1998 Annu Rev Med 49:375-390). TcdA and TcdB are structurally homologous, and contain a putative N-terminal glucosyltransferase and a cysteine proteinase domain, a transmembrane domain, and a C-terminal receptor binding domain (von Eichel-Streiber C et al. 1996 Trends Microbiol 4:375-382) (Jank T et al. 2008 Trends in microbiology 16:222-229; Voth D E et al. 2005 Clin Microbiol Rev 18:247-263). Interaction between the toxin C-terminus and the host cell receptors is believed to initiate a receptor-mediated endocytosis (Florin I et al. 1983 Biochim Biophys Acta 763:383-392; Karlsson K A 1995 Curr Opin Struct Biol 5:622-635; Tucker K D et al. 1991 Infect Immun 59:73-78). Although the intracellular mode of action remains unclear, it has been proposed that the toxins undergo conformational change at low pH in the endosomal compartment, leading to membrane insertion and channel formation (Florin I et al. 1986 Microb Pathog 1:373-385; Giesemann T et al. 2006 J Biol Chem 281:10808-10815; Henriques B et al. 1987 Microb Pathog 2:455-463; Qa'Dan M et al. 2000 Infect Immun 68:2470-2474). A host cofactor is then required to trigger a second structural change which is accompanied by an immediate autocatalytic cleavage and release of the glucosyltransferase domain into cytosol (Pfeifer G et al. 2003 J Biol Chem 278:44535-44541; Reineke J et al. 2007 Nature 446:415-419; Rupnik M et al. 2005 Microbiology 151:199-208). Once the glucosyltransferase domain reaches the cytosol, it inactivates proteins of the Rho/Rac family, leading to alterations of cytoskeleton and ultimately cell death (Just I et al. 1995 Nature 375:500-503; Sehr P et al. 1998 Biochemistry 37:5296-5304).

The clinical manifestation of CDAD is highly variable, from asymptomatic carriage, to mild self-limiting diarrhea, to the more severe pseudomembranous colitis. The prevalence of systemic complication and death in CDAD has become increasingly common (Siemann M et al. 2000 Intensive care medicine 26:416-421). In life-threatening cases of CDAD, systemic complications are observed, including cardiopulmonary arrest (Johnson S et al. 2001 Annals of internal medicine 135:434-438), acute respiratory distress syndrome (Jacob S S et al. 2004 Heart Lung 33:265-268), multiple organ failure (Dobson G et al. 2003 Intensive care medicine 29:1030), renal failure (Cunney R J et al. 1998 Nephrol Dial Transplant 13:2842-2846), and liver damage (Sakurai T et al. 2001 J Infect Dis 33:69-70). The exact reason for these complications is unclear, but entry of the toxin into the circulation and systemic dissemination have been suggested as possible causes (Hamm E E et al. 2006 Proc Natl Acad Sci USA 103:14176-14181).

Protection against *C. difficile* appears to be conferred by anti-toxin antibodies, which are present in the general population among individuals over 2 years of age, and at higher levels in individuals who have suffered less severe cases with less frequent relapse (Kelly C P 1996 Eur J Gastroenterol Hepatol 8:1048-1053; Kelly C P et al. 1996 Antimicrob Agents Chemother 40:373-379; Kyne L et al. 2000 N Engl J Med 342:390-397; Torres J F et al. 1995 Infect Immun 63:4619-4627; Viscidi R et al. 1983 J Infect Dis 148:93-100). Disease progression and recurrence seem to be associated with different subsets of antibodies in the circulation (Katchar K 2007 Clin Gastroenterol Hepatol 5:707-713), but the reason for this observation is unknown. In animal studies, neutralizing antibodies directed against TcdA inhibit fluid secretion in mouse intestinal loops and protect mice against systemic infection (Corthier G et al. 1991 Infect Immun 59:1192-1195). Co-administration of both anti-TcdA and anti-TcdB antibodies significantly reduces mortality in a primary hamster disease model as well as in a less stringent relapse model (Babcock G J et al. 2006 Infect Immun 74:6339-6347).

The mechanism of antibody-mediated protection is unclear, but it is likely that the cellular Fc receptors (FcR) are playing some roles. Fc receptors for IgG, known as FcγRs, are widely distributed on effector cells of the immune system (including macrophages, monocytes, neutrophils, and natural killer cells), and are essential in recognition and elimination of IgG-opsonized pathogens and immune complex. The FcγR family members include at least one high affinity receptor (FcγRI or CD64) and two low affinity receptors (FcγRIIA or CD32, and FcγRIII or CD16). Binding of these surface receptors to the Fc portion of IgG activates cell signaling pathways and triggers various cellular responses, such as production of reactive oxygen species (ROS), antibody-dependent cellular cytotoxicity, and release of inflammatory cytokines (Daeron, M 1997 Fc receptor biology Annu Rev Immunol 15:203-234; Ravetch J V et al. 2001 Annual review of immunology 19:275-290).

A feature of the present invention is a method for detecting a presence of toxigenic *Clostridium difficile* and/or *C. difficile* toxin in a biological sample, the method including steps of: contacting a first set of test cells with an aliquot of the sample and an amount of a toxin-enhancing antibody and measuring an amount of loss of cell viability for the first set of cells in comparison with an amount in a second set of the test cells not so contacted and otherwise identical, such that an amount of loss of cell viability in the first set in comparison to the second set is an indication of the presence of *C. difficile* or toxin in the sample. The method in related embodiments further includes contacting at least a third set of cells with at least one known amount of the *C. difficile* toxin as a positive control. The method in related embodiments further includes contacting at least a fourth set of cells with a different known amount of *C. difficile* toxin wherein a plurality of positive controls comprises a standard curve for toxin killing in the presence of the toxin-enhancing antibody. The method in related embodiments further includes adding to a duplicate of the first set of cells with the aliquot of sample and the toxin-enhancing antibody, an amount of an agent as a positive control, such that the agent can be an antibody or an anti-toxin known to neutralize at least one *C. difficile* toxin, such that the agent identifies the presence of the toxin, in which the presence of either TcdA or TcdB or both, is an indication of *C. difficile* infection. An anti-toxin is one or a group of antibodies known to respond to and/or neutralize a specific or group of toxins.

In general in the method above, measuring the loss of cell viability involves measuring at least one selected from the group of: decrease in respiration measured by tetrazolium dye, increase in cell rounding, appearance of glucosylation of Rac1, appearance of cytoskeleton disruption, appearance of necrosis, appearance of endocytosis of antibody-toxin, appearance of apoptosis, and decrease in cell attachment to a surface by electronic sensing of resistance or impedance.

Exemplary cells to use in the assays are white blood cells. For example, the white blood cells are macrophages, for example, the macrophages are mouse RAW 264.7 cells. Additionally, the cells display a receptor for IgG, for example, a recombinantly expressed Fc gamma receptor (FcγR). In certain embodiments, the cells are colonic epithelial cells.

The toxin-enhancing antibody is specific for an epitope of *C. difficile* toxin protein, which is selected from the group of TcdA and TcdB. In certain embodiments, the antibody has an IgG2a isotype. For example, the antibody is A1H3 or PCG4.1. An exemplary toxin is TcdA or TcdB. In general, the amount of toxin detected in the sample is less than about fifty picograms, less than about ten picograms, less than about five picograms, or less than about one picogram per milliliter of the sample.

The impedance or resistance of the cell is a measure of extent of cell attachment to a surface (multi-well culture well or "E-Plate device"); impedance or resistance is conveniently measurable by the real-time cell electronic sensing (RT-CES) instrument.

In general in the method prior to contacting the cells, frozen cells are defrosted and are used absent culturing. Thus the assay is fast and convenient. Thus in the method prior to contacting the cells, frozen cells are defrosted and are cultured prior to use. Alternatively prior to contacting the cells, fresh primary or cultured cells are harvested and used in the method. The method further involves analyzing viability data, which are available and are analyzed in less than a day, less than eight hours, less than six hours or even less than about three hours. Cells for the assay do not necessarily need to be cultured, providing a method that produces data much faster than those methods currently available. Alternatively, cultured cells are used in the assay. Alternatively, primary cells are used in the assay.

Another feature of the invention provided herein is a method of producing *Clostridium* toxins in a *Bacillus* host, the method involving the steps of: contacting a cell of a *Bacillus* species with a nucleic acid vector, the vector carrying: a gene encoding a *Clostridium* toxin protein, the gene operably linked to regulatory signals for controlling expression of the gene in the cell, such that the gene is further engineered as a nucleic acid fusion encoding a *Bacillus* signal sequence linked in the same reading frame as the toxin, the vector further carrying a selectable marker, to obtained transformants carrying the selectable marker; screening a plurality of the transformants for expression of toxin to obtain a transformant secreting the toxin as a full length protein; and expressing the recombinant toxin in the *Bacillus* cells as a secreted product. An exemplary *Bacillus* is *B. megaterium*, and an exemplary *Clostridium* is *C. difficile*. Methods for contacting a cell with a nucleic acid are well known, for example, using protoplasts of the cell made by treating the cells with lysozyme. Alternative methods of contacting cells with vectors in order to transform the cell, for example, gene gun methods, are within the scope of the invention.

According to a related embodiment, the signal sequence is a 28-amino acid peptide of *B. megaterium* extracellar esterase LipA. Further, the gene is obtained by polymerase chain reaction. In a related embodiment, the vector further encodes an affinity marker, and the gene encodes a fusion of the toxin protein with an amino acid sequence encoding the affinity marker. For example, the affinity marker is a poly-histidine that binds to biotin or Streptactin. For example the affinity marker is one from the group consisting of: avidin, streptavidin, and streptag. Streptag is an eight residue minimal peptide sequence that exhibits affinity for streptavidin and can be used as a fusion for purification of proteins. Having a fusion protein with either or both poly-his or streptag enables single step or two step purification to essentially homogeneity, with minimal addition to the native toxin protein.

In various embodiments, screening the plurality of transformants further involves contacting mammalian cells with a supernatant or a whole cell extract from a transformant and assaying contacted cells for cell rounding in the presence of the supernatant or extract in comparison to cells not so contacted. In general with the above methods, the amount of toxin obtained is at least an order of magnitude greater than that found in wild type *Clostridium*.

Also provided herein is a vector for recombinant high level expression of a *C. difficile* toxin. In various embodiments the vector is a shuttle vector. In general the shuttle vector replicates in *Bacillus* and in another prokaryotic cell. For example, the vector replicates in *Escherichia coli*. In general, the vector includes a BsrG1 cloning site for the amino terminus of the coding region of the gene. The vector for expressing the *C. difficile* toxin in a *Bacillus* cell includes a gene encoding the toxin by recombinantly ligating at a BsrG1 restriction site such that the amino terminus of the toxin protein is located at that site.

Further provided herein is a cell that carries the vector expressing the *C. difficile* toxin in a *Bacillus* cell.

The invention herein also features a kit for assay for the presence of *C. difficile* such that the kit includes a toxin-enhancing antibody, a toxin control, and a container. The kit in certain embodiments includes instructions for use. In other embodiments the kit includes at least one toxin neutralizing antibody. In general, the kit includes instructions for use.

In the course of characterizing herein a panel of anti-TcdA antibodies, a monoclonal antibody (Mab) named A1H3 was observed that greatly enhanced killing of murine macrophages and human monocytes by TcdA. It was further observed that TcdA/A1H3 immune complex was more potent than TcdA alone in inactivating Rho-GTPase, disrupting the cytoskeleton, and inducing TNF-α production.

The invention herein provides in one embodiment an assay for the presence of *C. difficile* cells and toxins. The inventors have discovered that certain antibodies enhance the effects of *C. difficile* toxins on certain mammalian cells. The toxin-enhancing antibody is generally of the IgG2a class, and the toxin sensitive mammalian test cells bear FcγR proteins. Exemplary types of antibodies are identified as A1H3 and PCG4.1 as described herein.

An anti-TcdA MAb, A1H3, as shown herein enhances TcdA-mediated cellular effects in murine macrophages and human monocytes. The observed effects included: 1) inducing cell rounding and death; 2) inactivating small Rho-GTPase via glucosylation; and 3) eliciting TNF-α production in macrophages. The antibody-dependent enhanced cytotoxic activity of TcdA was not observed in other cell types, including the human intestinal epithelial HCT8 or HT29 cells, or murine colonic CT26 cells.

Examples herein showed an important role of FcγRI in A1H3-dependent enhancement of TcdA toxicity. While blocking the FcγRII/III with anti-mouse-CD16/32 antibodies did not affect the glucosylation of Rac1 in RAW 264.7, pre-saturation of FcγRI on THP1 with anti-human-CD64 antibodies significantly reduced the level of Rac1 glucosylation. Anti-human-CD64 blocking antibodies failed to completely abolish the enhancement of TcdA activity on THP1 cells by mouse A1H3 antibody. Without being limited by any particular theory or mechanism, this result may be due to the inefficient interaction between mouse-derived A1H3 and human FcγRs in THP1. Additionally, pre-incubation of the TcdA/A1H3 with a recombinant mouse CD64 was observed to completely block the A1H3-mediated enhancement of the glucosyltransferase activity by TcdA in RAW 264.7 cells. Finally, the expression of FcγRI strikingly enhanced the sensitivity of mRG1-1 cells to TcdA when complexed with A1H3. Similarly, the presence of A1H3 greatly enhanced the glucosyltransferase activity of TcdA in mRG1-1 cells. Neither cytotoxicity nor glucosyltransferase activity was enhanced by A1H3 in CHO cells, the parental line of mRG1-1.

Members of FcγR family consist of at least three members, FcγRI, II and III (Ravetch J V et al. 2001 Annual review of immunology 19:275-290). Murine FcγRI has higher affinity to IgG2a than other IgG subisotypes (Gessner J E et al. 1998 Annals of hematology 76:231-248). Although FcγRI is a high-affinity receptor capable of binding IgG monomer, a noticeable surface binding of A1H3 to RAW 264.7 only occurred when it was complexed with TcdA. This may be due to the relative low expression of FcγRI on these cells. In fact, the monomeric A1H3 binding was detected on mRG1-1 cells, which were engineered to express high level of FcγRI (Cho S et al. 1997 Int Immunol 9:239-248). However, the binding of TcdA with FcγRI was significantly enhanced after its association with antigen A1H3, in comparison with those treated with TcdA alone, indicating that the presence of A1H3 facilitated recruitment of TcdA to cell surface which might consequently contribute to the antibody-dependent enhancement of toxin activity. Without being limited by any particular underlying mechanism data herein showed that A1E6, an IgG1 monoclonal antibody against TcdA, neither enhanced toxin binding to macrophages nor augmented toxin activity when complexed with TcdA. Similar to A1E6, another anti-TcdA IgG1 Mab, A1B1, had no enhancing effects.

Upon binding to FcγRs, the immune complexes are internalized via either phagocytosis or endocytosis. The mode of internalization is intimately linked to the size of the bound complexes (Daeron, M 1997 Fc receptor biology Annu Rev Immunol 15:203-234; Mukherjee S et al. 1997 Physiol Rev 77:759-803). Large opsonized particles are internalized by phagocytosis, while internalization of small soluble complexes most likely occurs via endocytosis. Mechanistically, the molecular process underlying the FcγR-mediated phagocytosis and endocytosis differs dramatically. Endocytosis specifically requires the assembly of clathrin at the site of receptor clustering (Mukherjee S et al. 1997 Physiol Rev 77:759-803). FcγRI-mediated phagocytosis, however, requires a signal-transducing γ chain that harbors tyrosine activation motifs (ITAMs) (Davis W et al. 1995 Embo J 14:432-441; Huang Z Y et al. 2006 J Leukoc Biol 80:1553-1562). Cells expressing FcγRI extracellular domain (in the absence of γ subunit) are unable to phagocytose large particles, while their endocytic functions remain intact (Davis W et al. 1995 Embo J 14:432-441). In examples herein, enhancement of TcdA activity mediated by A1H3 did not require the presence of γ chain, since expression of FcγRI α chain alone on mRG1-1 was observed to render the cells more susceptible to A1H3-dependent enhancement of toxicity of TcdA, suggesting that the TcdA/A1H3 was taken up via FcγRI-mediated endocytosis. The involvement of an endocytic pathway in the uptake of TcdA/A1H3 by RAW 264.7 was further supported by the observation that TcdA/A1H3-mediated Rac1 glucosylation and TNF-α production were inhibited by chlorpromazine and ammonium chloride/chloroquine, chemicals that are known to target the endocytic pathway.

Examples herein are relevant to the relationship of antibody response in host protection and pathogenesis of *C. difficile* associated diseases. Toxins TcdA and TcdB are key virulence factors, and antibodies against the two toxins are highly protective (Corthier G et al. 1991 Infect Immun 59:1192-1195; Kyne L et al. 2001 Lancet 357:189-193). Intravenous administration of immunoglobulin against TcdA and TcdB to patients with recurrent or severe CDAD resulted in symptom resolution (Leung D Y et al. 1991 J Pediatr 118:633-637). A higher level of anti-TcdA antibodies following colonization or primary disease has been correlated with protection from CDAD or relapse (Kyne L et al. 2001 Lancet 357:189-193; Kyne L et al. 2000 N Engl J Med 342:390-397). Finally, vaccination of long-term relapsing humans with toxoid A and B has successfully prevented additional relapses (Sougioultzis S et al. 2005 Gastroenterology 128:764-770). However, different subsets of antibodies may have different roles in host protection and disease progression (Katchar K 2007 Clin Gastroenterol Hepatol 5:707-713). While patients with recurrent CDAD do not show evidence in overall humoral immune deficiency, they do have a selectively reduced IgG2 and IgG3 response against TcdA, compared to those with single CDAD (Katchar K 2007 Clin Gastroenterol Hepatol 5:707-713). Data herein showed that the IgG2a subisotype of anti-TcdA actually enhanced the toxicity of TcdA on macrophages/monocytes in vitro. Whether these findings apply for in vivo pathogenesis of *C. difficile* infection remains to be determined. Antibody-dependent enhancement of viral infection has been widely described in mammalian viruses as well as in bacteriophages (Leopold P L et al. 2006 Journal of virology 80:10237-10247; Sapinoro R et al. 2008 Virology 373:274-286; Schlesinger J J et al. 1999 Virology 260:84-886). Instead of neutralizing or reducing viral infectivity, the presence of virus-specific antibodies paradoxically potentiates the infection of susceptible host cells, a process that is most often mediated by receptors for complement components or the Fc portion of immunoglobulins (Homsy J et al. 1989 Science 244:1357-1360; Leopold P L et al. 2006 Journal of virology 80:10237-10247; Sapinoro R et al. 2008 Virology 373:274-286; Takada A et al. 2003 Rev Med Virol 13:387-398). Given the results from examples herein, it is likely that some toxin-specific antibodies have detrimental effects on the host mediated by enhanced toxin activity. Such effects, however, yet to be illustrated in humans, or in animal models, are being investigated in our laboratory.

Additionally, the present invention provides methods and vectors for expression of *C. difficile* toxins. As clostridia are anaerobic pathogens, the expression systems provided herein use strains of bacilli that are aerobic and are more conveniently cultured, e.g. *Bacillus megaterium*.

A portion of this work appeared in two published papers: "Expression of recombinant *Clostridium difficile* toxin A and B in *Bacillus megaterium*" by Guilin Yang, Boping Zhou, Jufang Wang, Xiangyun He, Xingmin Sun, Weijia Nie, Saul Tzipori, and Hanping Feng which appeared in BMC Microbiology 8:192, published Nov. 6, 2008; and, "An ultrasensitive rapid immunocytotoxicity assay for detecting *Clostridium difficile* toxins" by Xiangyun He, Jufang Wang, Jennifer Steele, Xingmin Sun, Weijia Nie, Saul Tzipori, and Hanping Feng which appeared in J Microbiol Methods 2009 published electronically Apr. 7, 2009. A portion of this work has been accepted for publication in a manuscript entitled, "Antibody-enhanced, FcγR-mediated endocytosis of *Clostridium difficile* toxin A" by Xiangyun He, Xingmin Sun, Jufang Wang, Xiaoning Wang, Quanshun Zhang, Saul Tzipori, and Hanping Feng, the abstract of which was published Mar. 23, 2009 in the journal Infection and Immunology. All of these papers are hereby incorporated by reference herein in their entireties.

The toxin genes tcdA and tcdB were herein amplified by PCR using chromosomal DNA from a toxigenic strain as a template, and cloned into a shuttle vector pHis1522. The sequences of both tcdA and tcdB genes in the vector were verified by DNA sequencing. The constructs were transformed into *B. megaterium* protoplasts and protein expression was controlled by a xylose promoter. The recombinant toxins (rTcdA and rTcdB) were purified from bacterial crude extracts. Approximately 5-10 mg of highly purified recombinant toxins were obtained from one liter of bacterial culture. The resulting rTcdA and rTcdB had similar molecular masses to the native toxins, and their biological activities were found to be similar to respective native counterparts by a series of assays of function and structure.

Two exotoxins produced by toxigenic *C. difficile*, toxin A (TcdA) and toxin B (TcdB), are most extensively studied and thought to be major virulent factors of CDAD (Kelly C P et al. 1994 N Engl J Med 330(4):257-262; Voth D E et al. 2005 Clin Microbiol Rev 18(2):247-263). TcdA (308 kDa) and TcdB (269 kDa) belong to the large clostridial cytotoxin (LCT) family and share 49% amino acid identity (Just I et al. 2004 Reviews of physiology, biochemistry and pharmacology 152: 23-47). The two toxins have a similar structure containing a putative receptor binding domain (RBD), a transmembrane domain (TMD), and a glucosyltransferase domain (Just I et al. 2004 Reviews of physiology, biochemistry and pharmacology 152:23-47; Schirmer J et al. 2004 Biochimica et biophysica acta 1673(1-2):66-74). After receptor-mediated internalization and intracellular cleavage, the toxins glucosylate members of the Rho-Rac family of small GTPases at a specific threonine residue in host intestinal epithelial cells, leading to alterations in the actin cytoskeleton, massive fluid secretion, acute inflammation, and necrosis of the colonic mucosa (Voth D E et al. 2005 Clin Microbiol Rev 18(2):247-263). Purified TcdA possesses potent enterotoxic and proinflammatory activity, as determined in ligated intestinal loop studies in animals (Kurtz C B et al. 2001 Antimicrobial agents and chemotherapy 45(8):2340-2347; Lyerly D M et al. 1982 Infect Immun 35(3):1147-1150). TcdA is also cytotoxic to cultured cells in a picomolar to nanomolar range. TcdB, more cytotoxic to cultured cells than TcdA, was previously reported to exhibit no enterotoxic activity in animals (Lyerly D M et al. 1982 Infect Immun 35(3):1147-1150; Lyerly D M et al. 1985 Infect Immun 47(2):349-352), but recent studies have found enterotoxic and proinflammatory activities in human intestinal xenografts in severe combined immunodeficient (SCID) mice (Savidge T C et al. 2003 Gastroenterology 125(2):413-420). Furthermore, the TcdA⁻B⁺ *C. difficile* strains are responsible for pseudomembranous colitis in some patients (Shin B M et al. 2007 Diagn Microbiol Infect Dis 60(4):333-337; Kikkawa H et al. 2007 J Infect Chemother 13(1):35-38).

A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. Therefore, it is contemplated to cover the present embodiments of the invention and any and all modifications, variations, or equivalents that fall within the true spirit and scope of the basic underlying principles disclosed and claimed herein.

EXAMPLES

Example 1

Cell Lines Toxins, Antibodies, Animals and Samples

The mRG1-1, an engineered CHO cell line expressing murine FcγRI-α-chain is described in Cho S. et al. 1997 Immunol 9:239-48. The highly purified recombinant holotoxins TcdA and TcdB used in this example have equivalent biological activities to native toxins (Yang G et al. 2008 BMC Microbiology 8:192 hereby incorporated herein by reference in its entirety). A1H3 is a mouse anti-TcdA MAb of IgG2a isotype generated in our laboratory.

Gnotobiotic piglets were maintained within sterile isolators as previously described (Krakowka S et al. 1987 Infect Immun 55:2789-96). Piglets were inoculated orally with $1 \times 10^6$ to $10^8$ of *C. difficile* (NAP1/027 strain) spores (n=12) at the age of 2 to 5 days. The fecal samples were collected at day 0 before inoculation and daily post-inoculation thereafter. The specimens were stored in aliquots at $-20°$ C. until further use. For sample processing, stool aliquots were thawed on ice and diluted in PBS (1:10, wt/vol). The supernatant was then harvested by centrifugation and passed through a 0.45 μm filter.

Example 2

Real-Time Cell Viability Monitoring

The real-time cell electronic sensing (RT-CES, or xCELLigence) system (Roche Applied Science, Indianapolis, Ind.) was employed to monitor the dynamic response of mRG1-1 to *C. difficile* toxin stimulation via measurement of cell index (Abassi Y A et al. 2004 J Immunol Methods 292:195-205). CI is a parameter to describe electronic impedance, which corresponds to the number of cells attaching to the bottom of microelectrode-embedded microplate (E-plate) wells as an index of viability. In addition, the CI value was found to be positively affected by the extent of cells spreading on the bottom (Abassi Y A et al. 2004 J Immunol Methods 292:195-205). *C. difficile* toxins disrupt cell attachment and cause cell rounding (i.e. reduce cell spreading), thus lowering the CI values.

A 16-well E-plate was seeded with mRG1-1 test cells ($2 \times 10^4$/well) before being placed on the RT-CES device station. Cells were either grown overnight before the addition of toxins or biological samples in the absence or presence of a saturating dose of A1H3, or mixed with these reagents directly before being added into the E-plates. To block toxin activity to confirm identity of the toxic material, rabbit antiserum against TcdA (generated for samples herein) or goat antiserum against both TcdA and TcdB (commercially available from TechLab Inc., Blacksburg, Va.) was applied. The dynamic change in impedance as a result of cell attachment was recorded using a parameter of viability which is defined herein as the cell index (CI). Loss of CI is a measure of cell death.

Example 3

Sensitivity of Assay Enhanced by Antibody A1H3

Figure 1B:
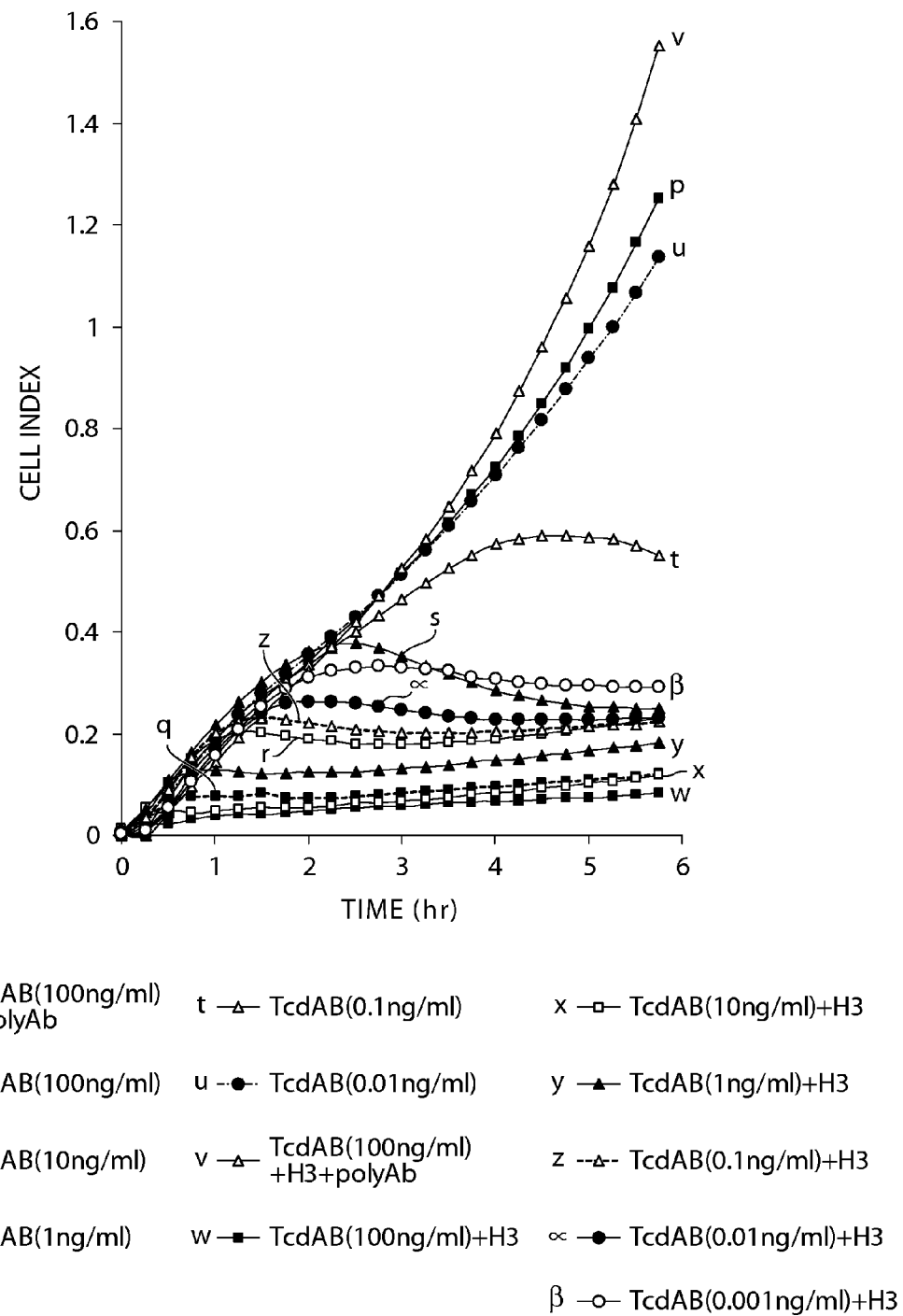

The RT-CES system was employed for a real-time detection of *C. difficile* toxin activity. As shown in FIG. 1 panel A, a dynamic response recorded by RT-CES revealed that A1H3 enhanced the sensitivity of mRG1-1 test cells to the cytotoxic effect of TcdA by a factor of at least 1000. A rapid decrease in CI within hours following the addition of toxins was observed in cells treated with 1000 ng/ml of TcdA, 10 ng/ml of TcdB, or TcdA at 1 ng/ml in the presence of A1H3 (FIG. 1 panel A). After 20 h of incubation, TcdA at a dose as low as 0.1 pg/ml was sufficient to render a complete loss of CI when A1H3 was present. This was in sharp contrast to the observation that TcdA alone at 10 ng/ml only resulted in a partial loss of CI as compared to the medium control (FIG. 1 panel A).

The cytotoxic effect on mRG1-1 cells by TcdA/A1H3 was completely blocked by rabbit-anti-TcdA sera, confirming that the loss of CI was TcdA-specific (FIG. 1 panel A). TcdB at doses of 10 or 1 ng/ml also sharply decreased electronic resistance, whereas a lower dose (100 pg/ml) resulted in a slow reduction of CI as a function of time (FIG. 1 panel A). Antibody A1H3 was found neither to cross-react with TcdB nor enhance its biological activity. Nevertheless, the cytotoxic effect of TcdB on mRG1-1 cells was significantly higher than that of TcdA in the absence of A1H3 (FIG. 1).

Example 4

Use of Frozen Test Cells

One of the disadvantages of a tissue-culture-based assay for detection of *C. difficile* toxins is the slow turnaround time (Chang T W et al. 1979 J Infect Dis 140:765-70). To overcome this, the freshly thawed mRG1-1 test cells from cryopreservation were added together with the toxins to E-plates. As shown in FIG. 1 panel B, an increase in CI value over time was observed in control cells (PBS vehicle treatment). In contrast, the CI remained low when cells were treated with a mixture of TcdA and TcdB at doses of 0.1 to 1 ng/ml or higher, indicating the intoxicated cells (viz., contacted with toxin) had a reduced ability attach to the bottom of E-plates. The presence of A1H3 substantially enhanced the sensitivity of the assay, detecting toxin activity at 1 pg/ml within 4 h (FIG. 1 panel B). That cell death was due to *C. difficile* toxin was shown using the goat antiserum against both TcdA and TcdB, as this antiserum blocked the cytotoxic activities of the toxins and allowed cells to attach to the bottom of wells, as indicated by an increase in CI (FIG. 1 panel B).

Example 5

Detecting Toxin in Biological Samples from Feces

To determine whether the immunocytotoxicity assay can be used to detect toxin activities in biological samples, mRG1-1 test cells on E-plates were treated with supernatants prepared from fecal samples from *C. difficile* challenged piglets.

Figure 2A:
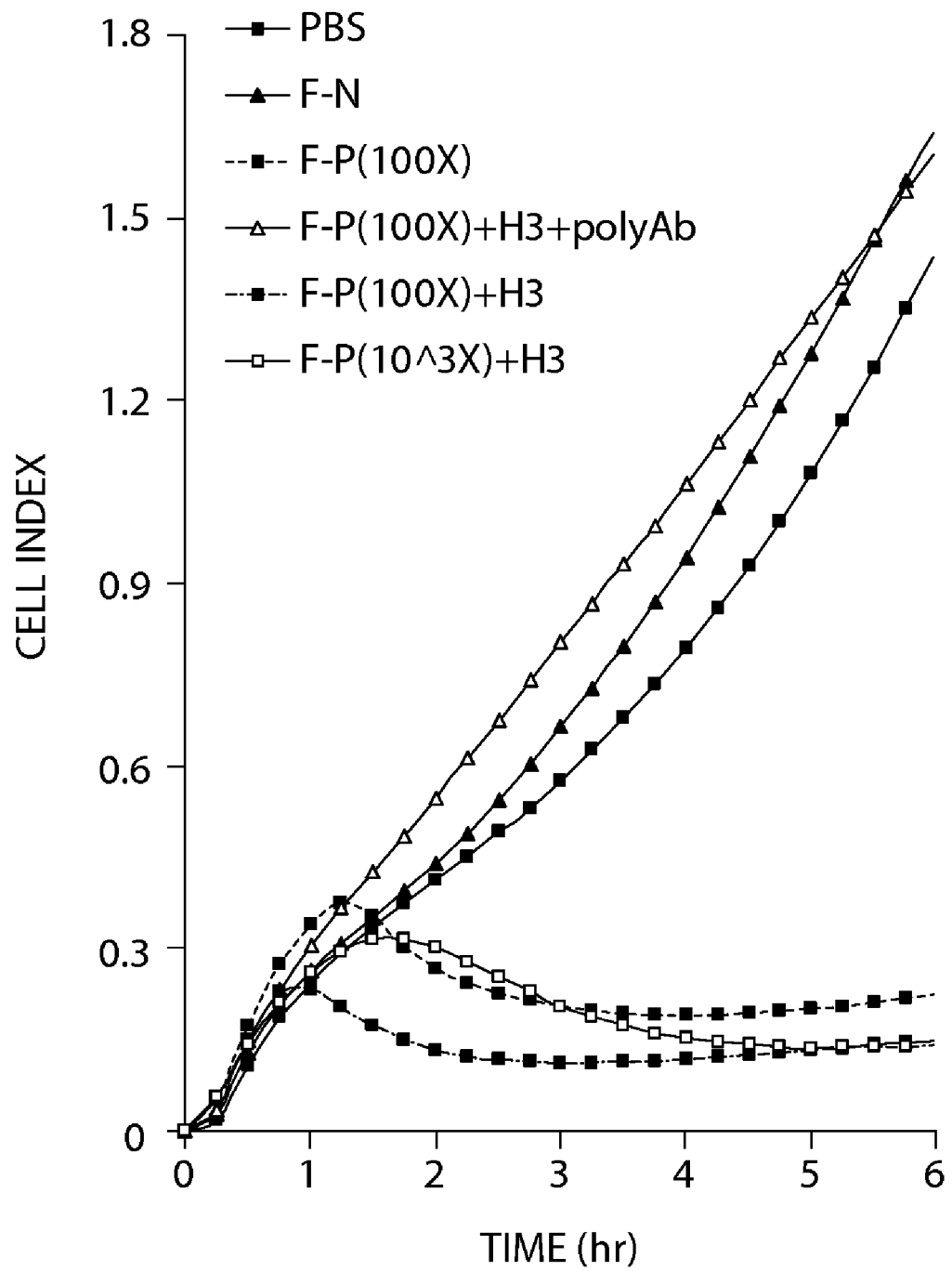
FIG. 2 is a set of line graphs showing detection of toxins in biological specimens.
Figure 2B:
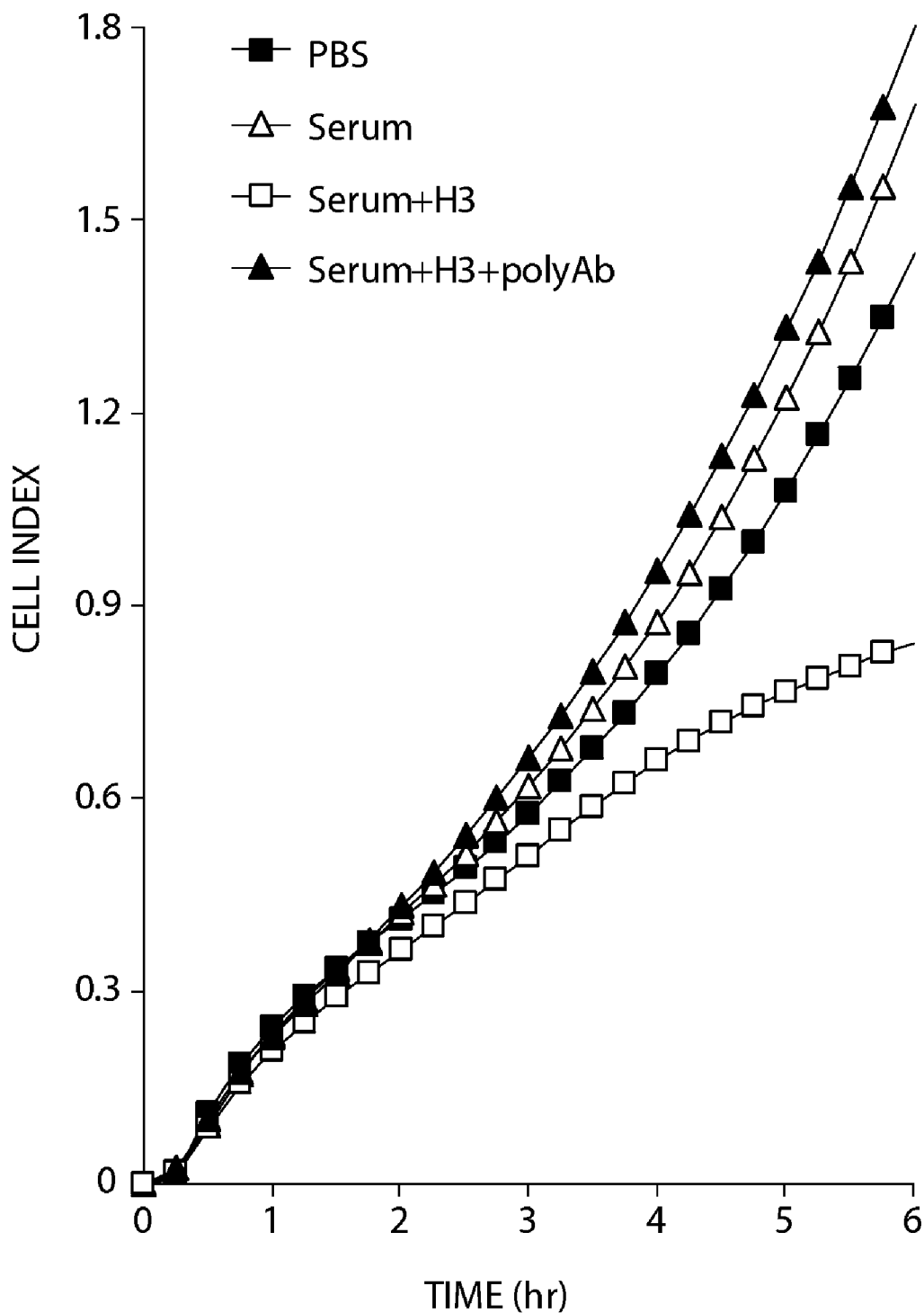
Figure 2C:
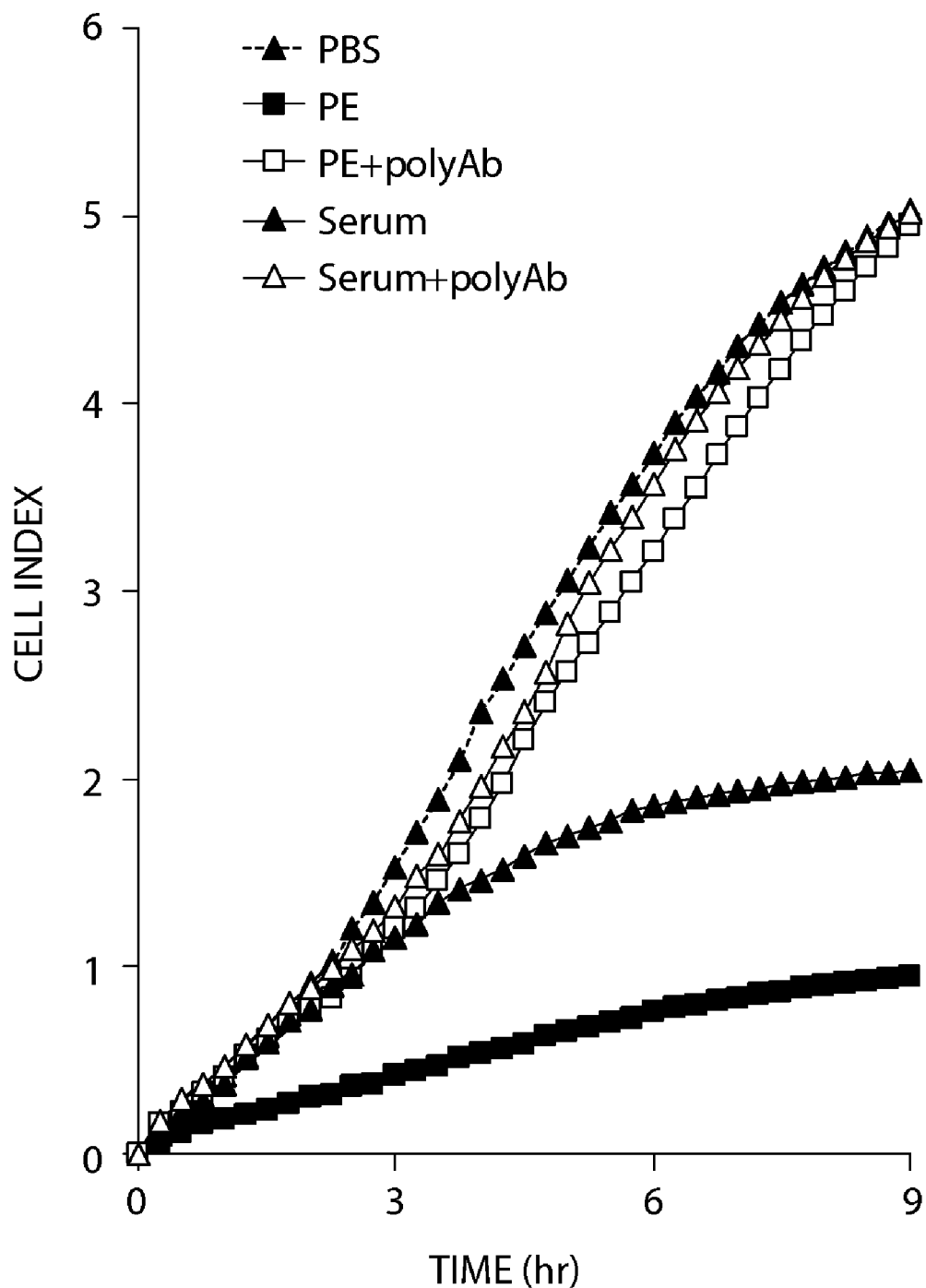

FIG. 2 panel A shows representative data from one piglet. A low CI was observed in test cells treated with 100-fold diluted fecal sample from an infected piglet three days post infection (FIG. 2 panel A, solid squares, F—P (100×). In contrast, a sample from the same piglet taken before bacterial inoculation at the same dilution did not block the increase of the CI (FIG. 2 panel A, solid triangles, F-N)

The presence of A1H3 allowed the detection of toxin activity in the 1000-fold diluted fecal sample within 2 to 3 h (FIG. 2 panel A). Anti-serum against TcdA and TcdB completely neutralized the toxin activities in fecal samples, confirming that the low CI values caused by fecal samples were due to *C. difficile* toxins (FIG. 2 panel A). These data demonstrated that the immunocytotoxicity assay was capable of rapidly detecting *C. difficile* toxins in highly diluted fecal samples from a *C. difficile* infected piglet.

Example 6

Detecting Toxin in Serum Samples and Pleural Effusion Samples

Life-threatening cases of CDAD are often accompanied by systemic complications (Siemann M et al. 2000 Intensive Care Med 26:416-21). It has been suggested that a possible cause might be the toxins entering into circulation and disseminating systemically (Hamm E E et al. 2006 Proc Natl Acad Sci USA 103:14176-81). We have observed that the severe cases of *C. difficile* infection in experimental piglets are associated with systemic complications. We therefore measured the toxin activities in serum from the severely infected piglets using the immunocytotoxicity assay. The serum alone failed to inhibit the increase of CI as compared to that in PBS group, suggesting that the amount of toxins in the serum, if any, was not high enough to block the cell attachment (FIG. 2 panel B).

However, in the presence of A1H3, the ascent of CI was partially inhibited by the serum sample (FIG. 2 panel B). The inhibitory effect was reverted by anti-sera against *C. difficile* toxins (FIG. 2 panel B), indicating that it was indeed a result of the toxins. Similarly, the serum and pleural effusion from another severely infected piglet reduced the ascent of CI, which was reverted by the anti-serum against *C. difficile* toxins (FIG. 2 panel C). Furthermore, these samples caused the rounding of mRG1-1 cells after an overnight culture only when A1H3 was present. The anti-serum against the toxins blocked such cytopathic effects of these samples.

These data demonstrated that a low level of toxins disseminated in the circulation of the severely affected piglets, which might explain the systemic complications seen in these piglets. Systemic complications are also observed in severe cases of *C. difficile* infected human patients, but whether these complications are associated with the toxins in circulation remains to be determined. Our ultrasensitive immunocytotoxicity assay may offer such a determination.

The cell-based immunocytotoxicity assay herein detected biological activities of *C. difficile* toxins, and in porcine clinical samples. Compared to the "gold standard" Cytotoxin B assay, this method is substantially more sensitive for detecting TcdA. The assay utilized A1H3, an anti-TcdA MAb, which substantially augments the cytotoxic activity of TcdA on FcγRI expressing cells. In addition, by utilizing freshly thawed cells and the A1H3 antibody, the turnaround time of the assay was reduced to 2-4 h. Since the cryopreserved cells were applied directly from the freezer, a cell culture facility and expertise in cell culture techniques were no longer required. A $CO_2$ incubator was not needed when a pH-buffered medium was used. Furthermore, the assay is easy to perform. After mixing samples with cells and reagents into E-plates, the results were obtained in a real-time and automatic fashion. The immunocytotoxicity assay in the examples herein is a rapid and easy-to-perform method with superior sensitivity and specificity for detecting the biological activity of *C. difficile* toxins, and therefore is capable of diagnosis of *C. difficile* infection.

Example 7

Additional Test Cells

The murine macrophage cell line RAW 264.7, the human monocyte cell line THP1, and the Chinese hamster ovarian cell line CHO were obtained from the American Type Culture Collection (ATCC, Manassas, Va.). Cells were maintained in Dulbecco's modified Eagle medium (Invitrogen, Carlsbad, Calif.) containing 10% fetal bovine serum (Invitrogen), 100 U/ml penicillin, 100 μg/ml streptomycin, 2 mM L-glutamine and 1 mM sodium pyruvate. Peritoneal exudate macrophages were isolated from C57BL/6 mice (Jackson Laboratory, Bar Harbor, Me.) by peritoneal lavage 3 days after intraperitoneal (i.p.) injection of 1 ml sterile 3% thioglycollate broth. Cells were collected by washing the peritoneal cavity with 3 ml of sterile PBS and red blood cells were lysed with RBC lysis buffer (Sigma, St Louis, Mo.). Cells were incubated for 2 h at 37° C. to allow adherence of macrophages. Non-adherent cells were removed subsequently by washing. The native TcdA (nTcdA) was purified from the culture supernatant of toxingenic *C. difficile* strain VPI 10463 (kindly provided by Dr. Abraham L. Sonenshein, Tufts University School of Medicine) as previously described (Kamiya S et al. 1989 J Med Microbiol 30:69-77; 32 Krivan H C et al. 1987 Infect Immun 55:1873-1877; Sullivan N M et al.1982 Infect Immun 35:1032-1040) with some modifications (Yang G et al. 2008 BMC Microbiology 8:192). The nTcdA was used to generate anti-TcdA MAbs. The full-length recombinant TcdA (rTcdA) was purified from total crude extract of *Bacillus megaterium* as described herein and in Yang et al., 2008 BMC Microbiology 8:192, hereby incorporated by reference herein in its entirety. The biological activity of rTcdA is shown herein to be essentially identical to nTcdA. The highly purified rTcdA that was observed as a single band on SDS-PAGE and was devoid of detectable Toll-like receptors TLR2 and TLR4 ligand activity as determined by bioassays. Purified rTcdA was used in these examples, unless otherwise specified.

Example 8

Expression of Recombinant TcdA Peptide Fragments

Sequences encoding the truncated TcdA fragments F3 (From 1185 to 1838 amino acid) and F4 (From 1839 amino acid to the carboxyl terminus) were amplified with primers F3 forward (5'-GGTTGCTGGATCCATAAGAGATTTATAC-CCAGGTAAATTTTACTGGAGATTCTATGC; SEQ ID NO: 1) and F3 reverse (5'-CCATGCTGAGCTCGCATTATT-TATATTGATTAATCCTTTAACTAATTTACTATCTTCAT-CATAG; SEQ ID NO: 2), and F4 forward (5'-GGTTGCTG-GATCCTCATTATTCTATTTTGATCCTATAGAATTT-AACTTAGTAACTGGATGG; SEQ ID NO: 3) and F4 reverse (5'-CCATGCTGAGCTCGCGCCATATATC-CCAGGGGCTTTTACTCCATCAAC; SEQ ID NO: 4), respectively. A BamHI site was engineered in each forward primer and a SacI site in each reverse primer, enabling directional cloning of the PCR products into a pET32a prokaryotic expression system (EMD Biosciences, Gibbstown, N.J.). The vector adds a $(His)_6$ tag to the N-terminus of the recombinant peptides, facilitating subsequent purification. Protein expression was induced by isopropyl-β-D-thiogalactopyranoside (IPTG) at a concentration of 0.6 mM. Recombinant peptide fragments were purified on a nickel column (NI; GE healthscience, Waukesha, Wis.).

Example 9

MAb Generation

Murine hybridomas secreting anti-TcdA antibodies were generated using nTcdA as an immunogen as described with modifications (hang Q et al. 2005 Infect Immun 73:5166-5172). The hybridoma supernatants were screened for their antigen binding capacity by enzyme-linked immunosorbent assay (ELISA) using microplates coated with 0.5 μg/ml of rTcdA. Positive hybridomas were selected and cloned. The isotype of MAbs was determined by ELISA. All antibodies were IgG isotypes, recognizing both native and recombinant TcdA and did not cross-react to TcdB. The reactivity of MAbs A1B1 (IgG1), A1E6 (IgG1) and A1H3 (IgG2a) was further mapped by Western blot and ELISA using truncated TcdA peptide fragments. Mouse monoclonal antibody JF1 (IgG2a, generated in our laboratory) against an irrelevant antigen was used as an isotype control.

Example 10

Immunofluorescence Staining

Subconfluent cells on coverslips were treated with TcdA alone or TcdA in the presence of MAbs (1 µg/ml) at 4° C. or 37° C. for 30 min. For F-actin staining, cells were incubated with toxins at 37° C. for 2 h. The cells were fixed with 2% paraformaldehyde, followed by permeabilization in a permeabilizing buffer (PBS, with 1% BSA and 0.1% Triton X-100). For F-actin staining, cells were incubated in 1 µg/ml Alexa 568-phalloidin (Invitrogen; Carlsbad, Calif.) for 30 min at room temperature. For immunocomplex or toxin staining, cells were incubated with fluorochrome-conjugated anti-mouse-IgG (BD bioscience, San Jose, Calif.), or polyclonal rabbit anti-TcdA serum (prepared herein by methods known to one of skill in the art of antibody production), followed by fluorochrome-conjugated anti-rabbit-IgG (BD Bioscience). Cells were counterstained with 4',6-diamidino-2-phenylindole (DAPI) and imaged using a confocal microscope (Leica LSM TSC SP2 AOBS, San Francisco, Calif.). Surface binding of A1H3 to RAW 264.7 cells was examined by flow cytometry. RAW 264.7 test cells were incubated with A1H3 alone, TcdA/A1H3, or TcdA/A1E6 immune complex on ice for 30 min, followed by phycoerythrin-conjugated anti-mouse-IgG staining (BD bioscience). Cells were subsequently analyzed by cell sorting using a FACS Calibur (BD bioscience) flow cytometer.

Example 11

TNF-α Production

RAW 264.7 cells were exposed to TcdA (50 ng/ml) or TcdA (0.4 ng/ml) with or without MAbs for 6 h. Brefeldin A (Sigma) at 20 µM was added to block cytokine secretion. Cells were collected and permeabilized (BD™ PhosFlow, BD bioscience). TNF-α production was then determined by intracellular staining using an Alexa-647-conjugated anti-mouse-TNF-α antibody (BD bioscience). Ten thousand cells were collected for flow cytometry analysis. Lipopolysaccharide (LPS; *E. coli* 026 strain, Sigma, St. Louis, Mo.) at 1 µg/mL was used as positive control. In some experiments, cells were pre-incubated with pharmacologic agents known to inhibit endosome formation (i.e. chlorpromazine) or endosomal acidification (i.e. ammonium chloride and chloroquine) before the addition of TcdA/A1H3 immune complex.

Example 12

Cytotoxicity Assay Using Tetrazolium Dye

Subconfluent cells were seeded in a 96-well culture plate in 100 µL of medium, and exposed to TcdA with or without MAbs. A saturating dose of MAbs was used to form TcdA/MAb immune complex before it was added to the cells. After 2 days of incubation, 10 µL of MTT (3-(4,5-dimethylthiazol-2-yl)-2,5-diphenyltetrazolium bromide; 5 mg/ml) was added to each well and the plate was further incubated at 37° C. for 2 h. The formazan was solubilized with acidic isopropanol (0.4 N HCl in absolute isopropanol), and absorbance at 570 nm was measured using a 96-well ELISA reader. The cell viability was expressed as percentage of cells survival as compared to untreated control wells. The cytopathic change (cell rounding) was assessed using a phase-contrast microscope after 2 h of toxin treatment. The assay was repeated three times, and triplicate wells were assessed for cytopathic changes in each example.

Example 13

Immunodetection of Rac1

Protein lysates of cells treated with TcdA in the presence or absence of MAbs for 4 h at 37° C. were separated on a 12% Tris-glycine precast gel (Invitrogen) and transferred onto a nitrocellulose membrane. The membrane was probed with anti-Rac1 (MAb 102) (BD Bioscience) or anti-beta-actin antibodies (Sigma), followed by incubation with HRP conjugated goat-anti-mouse-IgG (Southern Biotechnology Associates, Birmingham, Ala.). The protein bands were visualized using a chemiluminescent substrate (Pierce, Rockford, Ill.). In FcγR blocking studies, an anti-mouse-CD16/32 neutralizing antibody (clone 2.4G2, BD bioscience) or an anti-human-CD64 neutralizing antibody (clone 10.1, RnD systems, St Paul, Minn.) was incubated with cells for 30 min on ice before the addition of TcdA/A1H3 immune complex. Alternatively, recombinant mouse CD64 (RnD systems) was mixed with TcdA/A1H3 before it was added to cells. In other experiments, chlorpromazine, ammonium chloride, or chloroquine was pre-incubated with the cells for 30 min before toxin or immune complex exposure. The blocking antibodies and the pharmacologic agents remained in the culture throughout the experiments.

Example 14

Figure 3A:
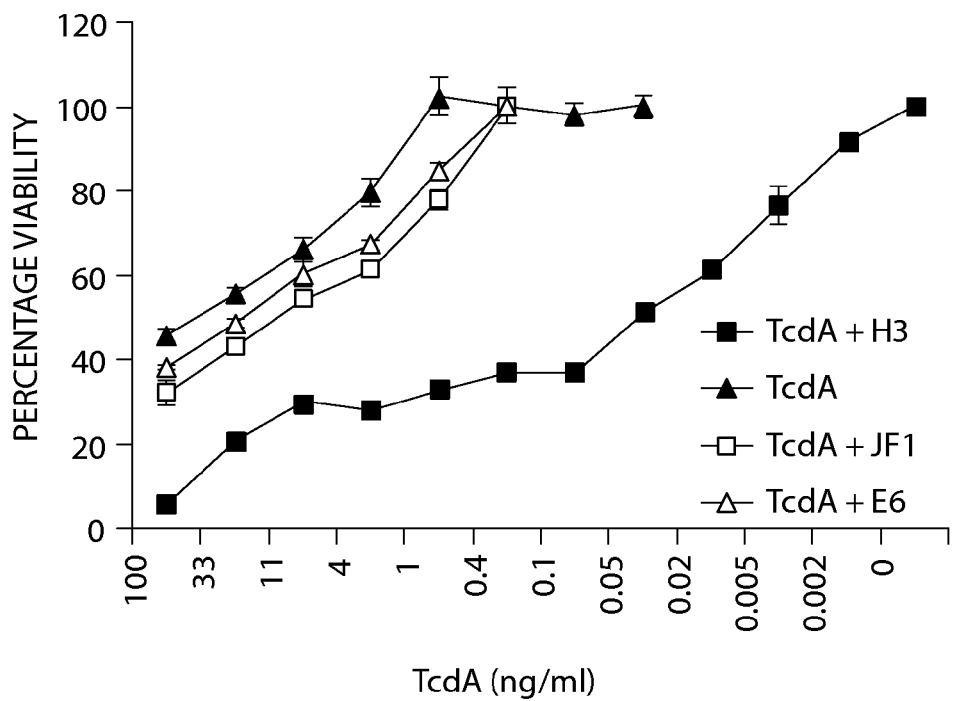
FIG. 3 is a set of line graphs showing antibody A1H3-dependent enhancement of cytotoxic effects of TcdA. Test cells were seeded in a 96-well plate.
Figure 3B:
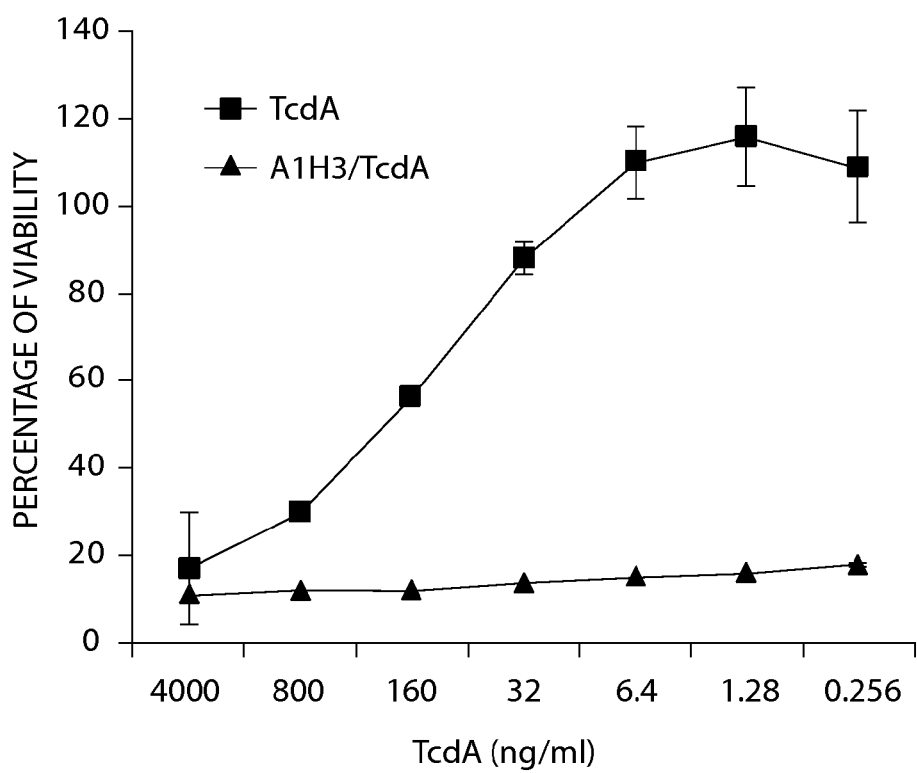
Figure 4A:
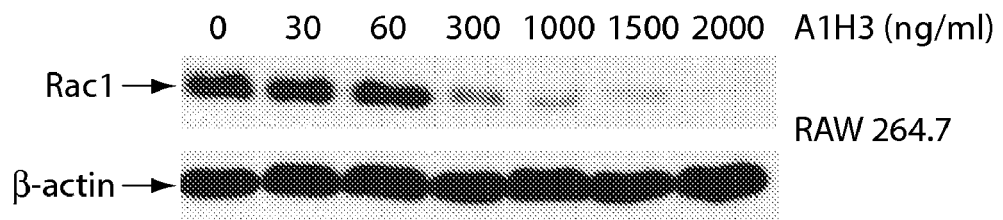
FIG. 4 is a set of photographs of Western blots of SDS-PAGE showing A1H3-dependent enhancement of the glucosyltransferase activity of TcdA. RAW 264.7 or THP1 test cells were treated with TcdA in the presence or absence of MAbs. Protein lysates were separated by SDS-PAGE, transferred to a nitrocellulose membrane, and probed with anti-beta-actin (control) or anti-Rac1 (MAb 102) antibody.
Figure 4B:
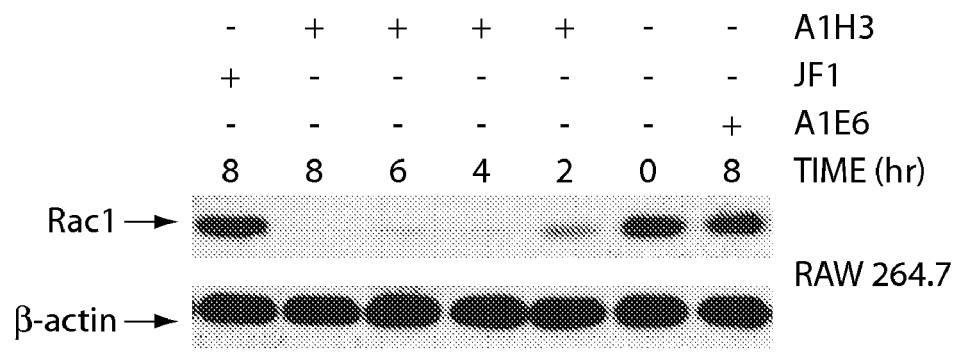
Figure 4C:
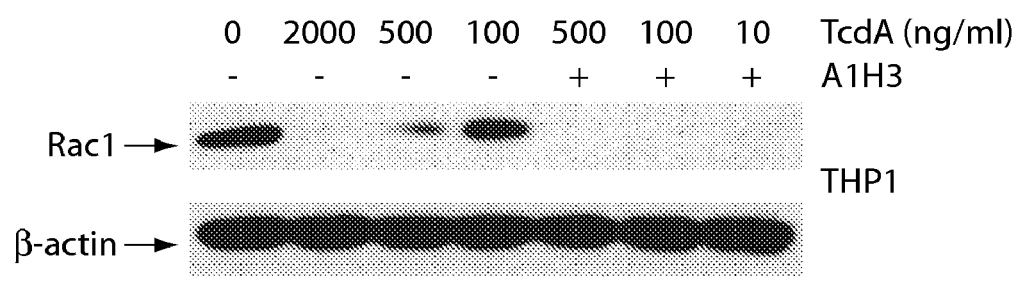
Figure 4D:
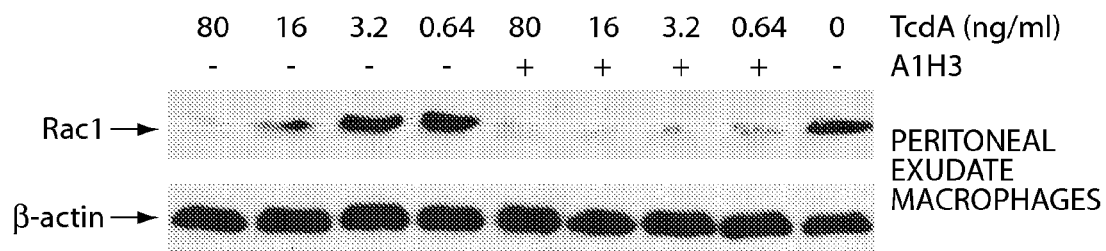
Figure 5A:
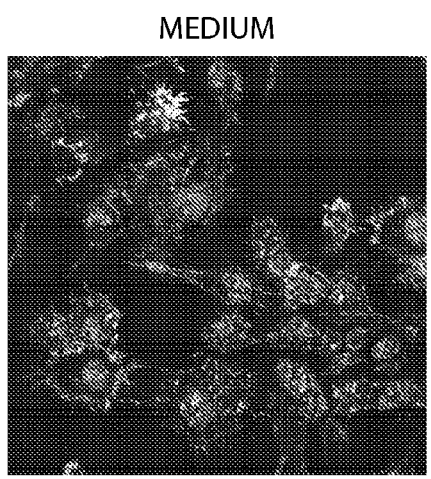
FIG. 5 is a set of photomicrographs showing effects of TcdA on actin organization with or without the presence of A1H3. RAW 264.7 test cell monolayers were incubated for 2 h with medium (FIG. 5 panel A), TcdA (50 ng/ml) (FIG. 5 panel B), TcdA (0.4 ng/ml) (FIG. 5 panel C), or TcdA (0.4 ng/ml)/A1H3 immune complex (FIG. 5 panel D). The cells were fixed and stained for F-actin with Alexa 568-phalloidin. The F-actin distribution was examined under a confocal microscope.
Figure 5B:
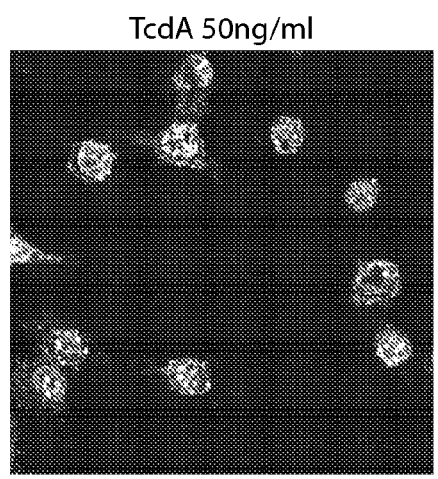
Figure 5C:
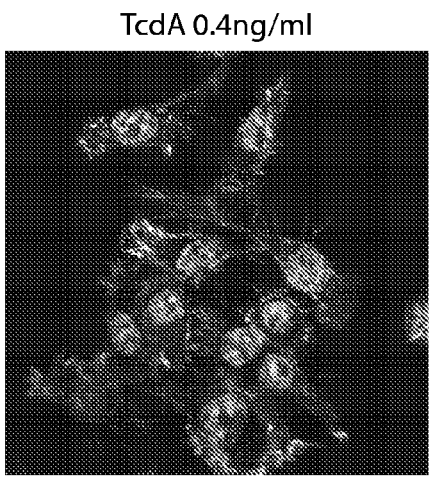
Figure 5D:
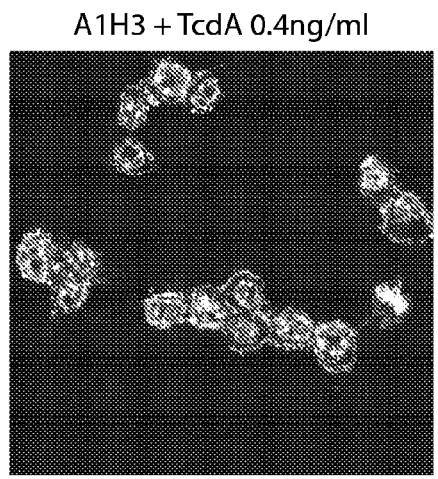

A1H3-Dependent Enhancement of Cytotoxicity by TcdA on Macrophages and Monocytes The anti-TcdA A1H3 recognized peptide fragment F4 (amino acid 1839 to the carboxyl terminus), whereas A1E6 recognized both F3 (amino acid 1185 to 1838) and F4 of TcdA. A1H3 was able to enhance the cytotoxic effect of TcdA on test cells that were murine macrophage RAW 264.7 test cells and human monocyte THP1 test cells. As shown in FIG. 3 panel A, the TcdA/A1H3 immune complex was about 1000 times more potent than TcdA alone in causing cell death in RAW 264.7 cells. While 100 ng/ml of TcdA was required to cause approximately 40% of cell death after 2 days of incubation, only 0.1 ng/ml of TcdA was needed to obtain the same effect in the presence of A1H3.

Other MAbs, such as A1E6 or JF1 (an unrelated control mouse MAb of IgG2a isotype), did not affect the cytotoxicity of TcdA in RAW 264.7 when present in the assay. A1H3 antibody (itself absent *C. difficile* toxin) did not affect cell viability. Similar data were obtained regarding the cytopathic effect (cell rounding) in RAW 264.7 cells, A1H3 also enhanced the cytotoxicity of TcdA using human monocyte THP1 as test cells (FIG. 3 panel B). The antibody-dependent-enhancement of cytotoxicity was not observed in intestinal epithelial cell lines, such as human HCT8 and HT29, or murine CT26.

Example 15

Enhanced Rac1 Glucosylation and Cytoskeleton Disruption by TcdA/A1H3 Immune Complex To examine whether A1H3 enhances the TcdA-induced glucosylation of Rho GTPase Rac1, RAW 264.7 or THP1 test cells were treated with low doses of TcdA with or without MAbs. Glucosylation of Rac1 was monitored by immunoblotting using anti-Rac1 (clone 102), which has a reduced affinity for the glucosylated target as compared to the unmodified protein (Genth H et al. 2006 FEBS letters 580: 3565-3569).

Loss of the Rac1 band was observed in cells incubated 4 h with TcdA/A1H3 immune complex at a dose of TcdA as low as 0.4 ng/ml for RAW 264.7 and 10 ng/ml for THP1 cells, while TcdA alone at 0.4 ng/ml or 100 ng/ml did not glucosylate Rac1 in RAW 264.7 or THP1 cells, respectively (FIG. 4 panels A and C). Moreover, glucosylation of Rac1 by TcdA in RAW 264.7 exhibited an A1H3 dose-dependent pattern. Complete loss of Rac1 band was observed when 2000 ng/ml of A1H3 was used to complex with TcdA (FIG. 4 panel A). In light of this result, A1H3 at 2000 ng/ml was considered a saturating dose and used in our subsequent experiments, unless specified otherwise.

The glucosylation of Rac1 occurred in a time-dependent manner, peaking between 4-8 h treatment (FIG. 4 panel B). Other monoclonal antibodies, JF1 or A1E6, did not enhance the TcdA-induced Rac1 glucosylation (FIG. 4 panel B). To further examine whether or not A1H3 can enhance the TcdA-induced glucosylation of Rho GTPase Rac1 from primary murine macrophages, peritoneal exudate macrophages were treated with TcdA in the presence or absence of A1H3. The glucosylation of Rac1 by TcdA in the primary macrophages exhibited a dose-dependent pattern (FIG. 4 panel D). The presence of A1H3 significantly enhanced the TcdA-mediated glucosylation of Rac1 in these cells. While TcdA alone at a dose of 0.64 ng/ml failed to glucosylate Rac1, such a dose in the presence of A1H3 resulted in a nearly complete loss of the Rac1 band (FIG. 4 panel D).

We next examined whether A1H3 could enhance the disruptive effects of TcdA on the actin cytoskeleton. Actin was labeled with Alexa-568 phalloidin and cells were imaged using a confocal microscope. The control RAW 264.7 monolayer exhibited an organized F-actin architecture (FIG. 5 panel A). While exposure to TcdA at 0.4 ng/ml (FIG. 5 panel C) did not alter the intracellular actin architecture, disruption of normal F-actin organization was clearly observed when TcdA (0.4 ng/ml) was complexed with A1H3 (FIG. 5 panel D). The effect was comparable to that observed with cells treated with TcdA alone at 50 ng/ml (FIG. 5 panel B).

Example 16

A1H3-Mediated Enhancement of TNF-α Production

An important step in triggering host immune response to *C. difficile* toxins is the release of inflammatory mediators such as TNF-α, IL-1β, and IL-6 from macrophages and monocytes (Flegel W A et al. 1991 Infect Immun 59:3659-3666; Ribeiro R A et al. 1997 Int Arch Allergy Immunol 112:27-35). Because TcdA-induced TNF-α production in macrophages was found to be dependent on the glucosyltransferase activity of the toxin, we examined whether the presence of A1H3 would enhance the production of TNF-α in macrophages.

Figure 6A:
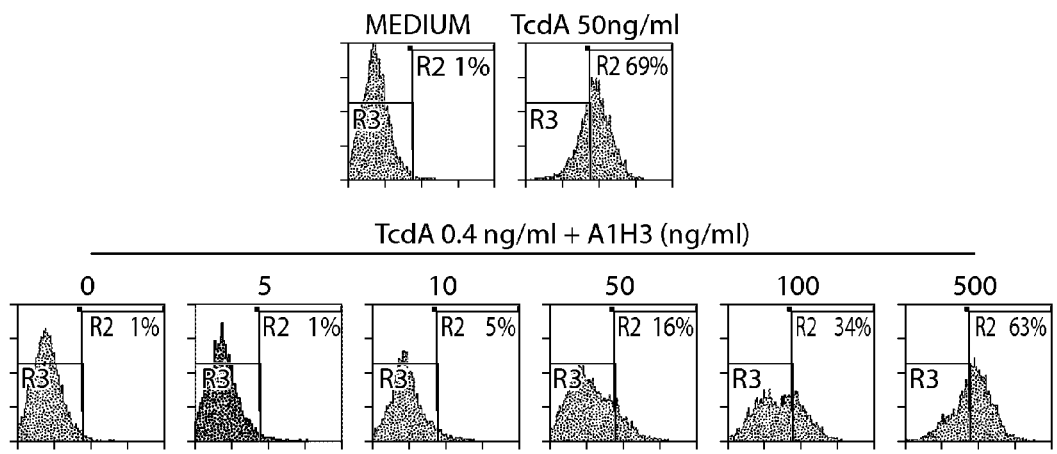
FIG. 6 is a set of cell sorting readout data showing the effects of MAbs on TcdA induced TNF-α production by macrophages. RAW264.7 test cells were treated for 6 h with TcdA (50 ng/ml), TcdA (0.4 ng/ml) complexed with A1H3 at the indicated doses (FIG. 6 panel A), or TcdA (0.4 ng/ml) complexed with MAbs (1 µg/ml) of each of A1H3, A1E6, PCG4.1 or JF1 (FIG. 6 panel B). TNF-α production was determined by intracellular staining followed by FACS analysis as described in examples herein. R3 region shows TNF-α negative cells and the percentage of TNF-α positive cells is indicated in R2 region.
Figure 6B:
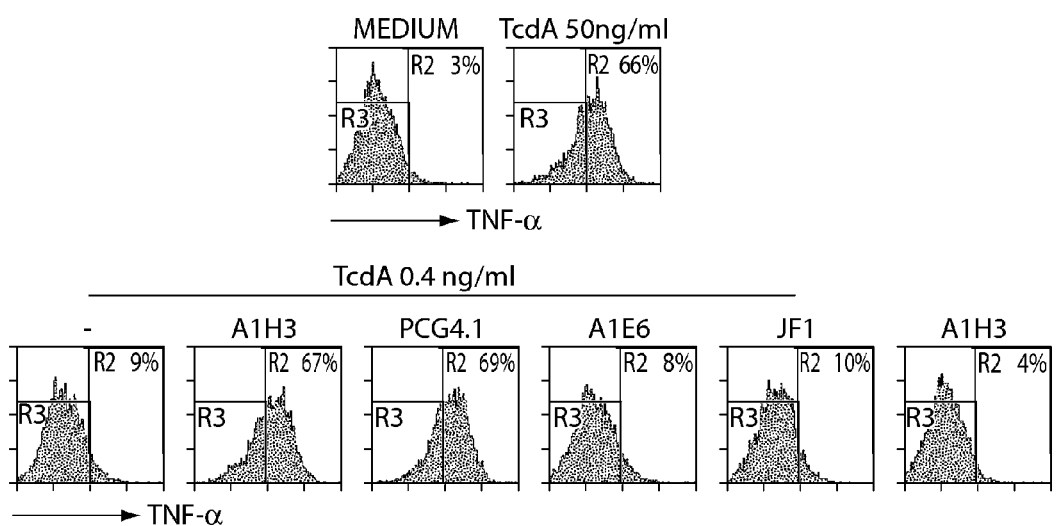
Figure 7A:
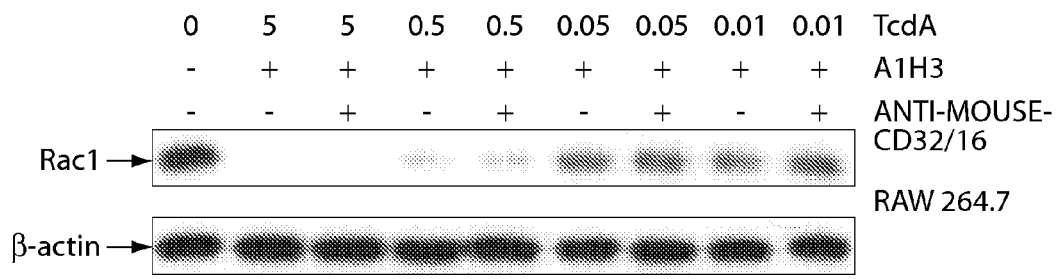
FIG. 7 is a set of photographs of Western blots showing the role of FcγRI receptors in A1H3-mediated enhancement of TcdA activity. A saturating dose of anti-mouse-CD16/32 or anti-human-CD64 was respectively incubated for 30 min on ice with RAW 264.7 (FIG. 7 panel A) or THP1 (FIG. 7 panel B), then TcdA/A1H3 immune complex was added. A mouse recombinant CD64 protein (5 µg/ml) was mixed with TcdA/A1H3 prior to addition to RAW 264.7 FIG. 7 panel C. RAW 264.7 (FIG. 7 panels A and C), THP1 (FIG. 7 panel B), CHO (FIG. 7 panel D) or mRG1-1 (FIG. 7 panel E) were treated with TcdA complexed with the indicated MAbs for 4 h. Immunodetection of Rac1 was performed as described in examples herein.
Figure 7B:
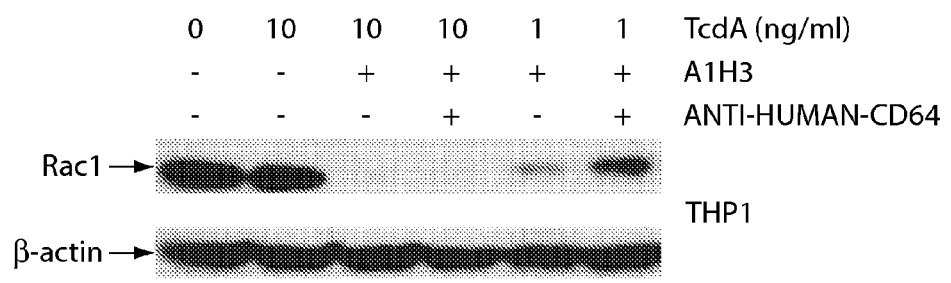
Figure 7C:
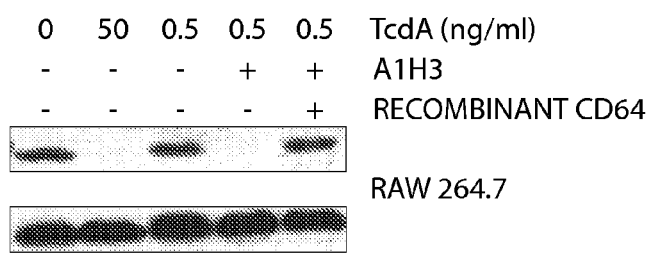
Figure 7D:
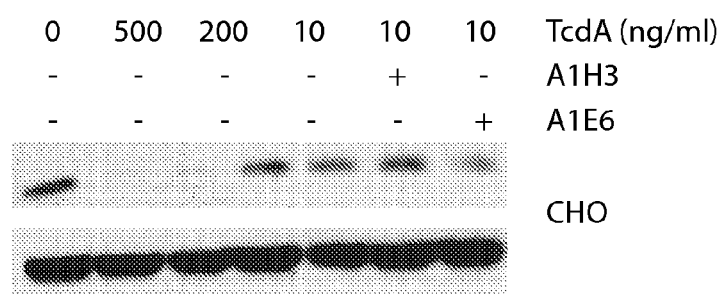
Figure 7E:
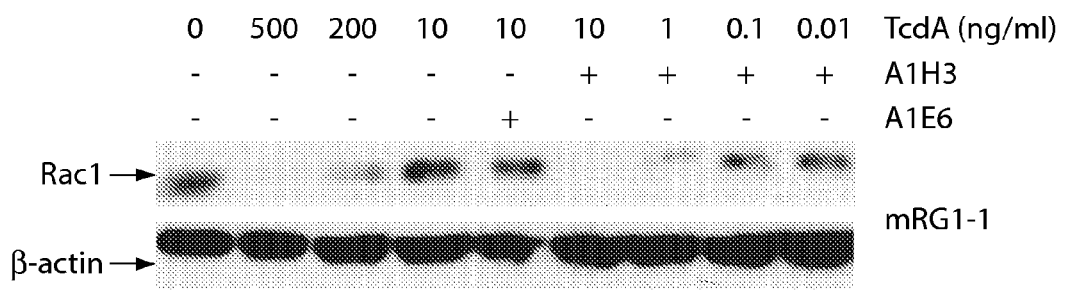
Figure 7F:
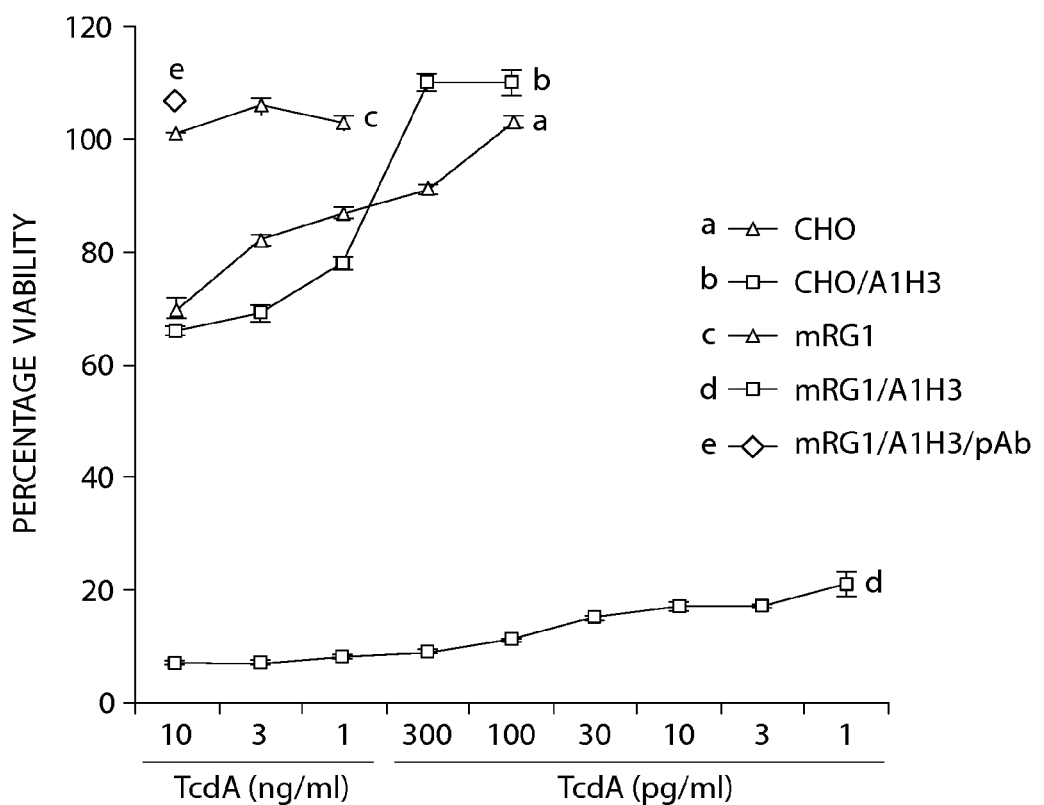

A1H3 was found to enhance TcdA-mediated TNF-α production in a dose-dependent manner in RAW 264.7 cells (FIG. 6 panel A). No enhancement was detected when TcdA was complexed with MAbs A1E6 or JF1 (FIG. 6 panel B). A1H3 alone did not induce detectable TNF-α production (FIG. 6 panel B). Since A1H3 was the only anti-TcdA MAb of IgG2a isotype, we examined another anti-TcdA IgG2a MAb, commercially available PCG4.1. This antibody complexed with TcdA, was observed to significantly enhance the TcdA-induced production of TNF-α in RAW 264.7 cells (FIG. 6 panel B).

Example 17

Role of FcγRI in Antibody-Dependent Enhancement of Toxin Effects

The FcγR receptors that specifically recognize the Fc portion of IgG include at least FcγRI (CD64), FcγRII (CD32) and FcγRIII (CD16). To test whether the interaction between the FcγR and A1H3 is involved in the antibody-dependent enhancement of toxin activity in macrophages, the Fc-binding sites on FcγRII/III and those on FcγRI were pre-saturated with specific anti-CD16/32 or anti-CD64 antibodies, respectively. Because antibody capable of blocking/neutralizing mouse CD64 is not available, we used anti-human CD64 antibody on THP1 cells and examined the Rac1 glucosylation following the addition of TcdA/A1H3 immune complex. Pre-saturation of FcγRII/III with anti-CD16/32 antibodies did not affect the glucosylation of Rac1 in RAW 264.7 (FIG. 7 panel A). In contrast, a reduced level of Rac1 glucosylation was observed in THP1 cells treated with FcγRI-specific antibodies (anti-CD64) followed by incubation with TcdA/A1H3 immune complex, when compared with the non-treated cultures (FIG. 7 panel B). Moreover, pre-incubation of TcdA/A1H3 complex with a recombinant mouse CD64 completely abrogated the glucosyltransferase activity mediated by TcdA/A1H3 (FIG. 7 panel C).

To further examine whether the FcγRI is involved in the A1H3-dependent enhancement of toxicity of TcdA, a murine FcγRI expressing CHO cell line, mRG1-1, was used as a source of test cells. CHO cells normally do not express FcγR and are relatively resistant to the TcdA-mediated Rac1 glucosylation and cytotoxicity. The data showed that, while CHO and mRG1-1 responded similarly to high dose of TcdA (500 ng/ml) with respect to Rac1 glucosylation, loss of the Rac1 band induced by TcdA at lower than 10 ng/ml was demonstrated in only mRG1-1 treated with TcdA/A1H3 immune complex, but not CHO cells (FIG. 7 panels D and E). No difference in Rac1 glucosylation in CHO cells compared to mRG1-1 cells was observed when A1E6 was used to complex with TcdA (FIG. 7 panels D and E). Furthermore, A1H3 greatly augmented the cytotoxic activity of TcdA in mRG1-1. As shown in FIG. 7 panel F, the presence of A1H3 did not affect the killing of wild type CHO cells by TcdA. In contrast, the expression of FcγRI-α chain alone strikingly enhanced the sensitivity of mRG1-1 to the cytotoxic effect of TcdA when complexed with A1H3, as compared to those treated with TcdA alone. mRG1-1 cells were more resistant to TcdA than CHO cells, since TcdA at 10 ng/ml did not noticeably induce cell death of mRG1-1 cells (FIG. 7 panel F). A rabbit anti-TcdA neutralized serum completely blocked cytotoxicity in mRG1-1 cells induced by TcdA/A1H3 complex (FIG. 7 panel F), indicating that cell death was mediated by TcdA.

Example 18

Enhanced Surface Binding of TcdA Mediated by A1H3

TcdA is thought to bind to specific cellular receptor(s), which mediate its cellular uptake through endocytosis (Krivan, H C et al. 1986 Infect Immun 53:573-58142; Na X et al. 2008 Infect Immun 76:2862-2871; Pothoulakis C et al. 1996 J Clin Invest 98:641-649). Surface binding of TcdA/A1H3 to RAW 264.7 cells was examined using fluorochrome-conjugated anti-mouse-IgG secondary antibodies.

Figure 8A:
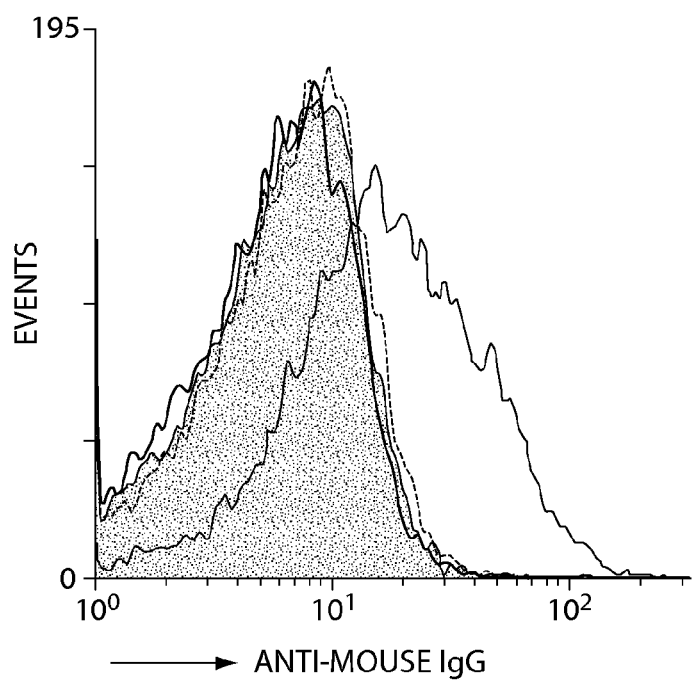
FIG. 8 is a set of cell sorting readouts and photomicrographs showing binding and internalization of A1H3 to RAW 264.7 test cells.
Figure 9A:
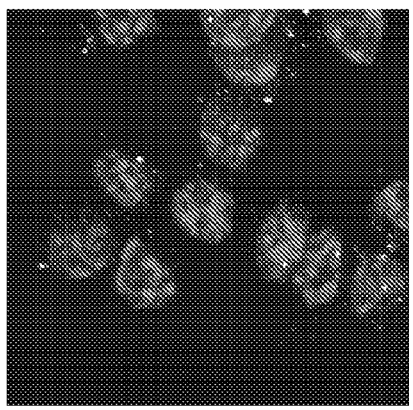
FIG. 9 is a set of photomicrographs showing binding and internalization of TcdA in RAW 264.7 or mRG1-1 test cells. RAW 264.7 (FIG. 9 panels A and B) or mRG1-1 (FIG. 9 panels C and D) grown on coverslips were incubated at 37° C. for 30 min with 10 ng/ml of TcdA (FIG. 9 panels A and C) or TcdA/A1H3 (FIG. 9 panels B and D). Cells were fixed and stained with polyclonal rabbit-anti-TcdA antibodies followed by Alexa-568-conjugated anti-rabbit-Ig antibody. TcdA binding and internalization was examined by confocal microscopy.
Figure 9B:
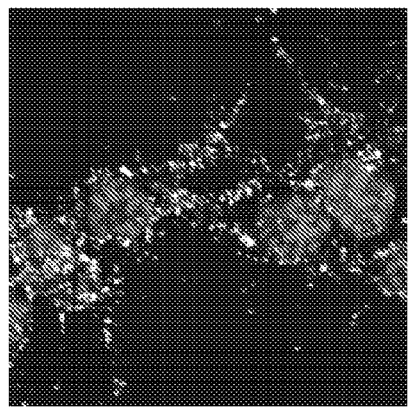
Figure 9C:
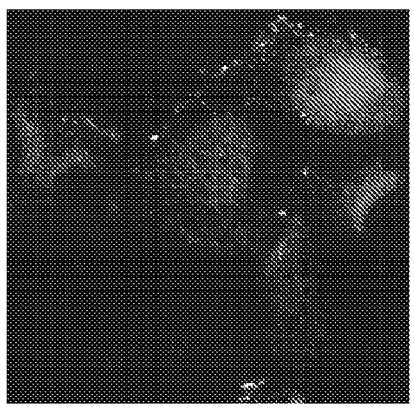
Figure 9D:
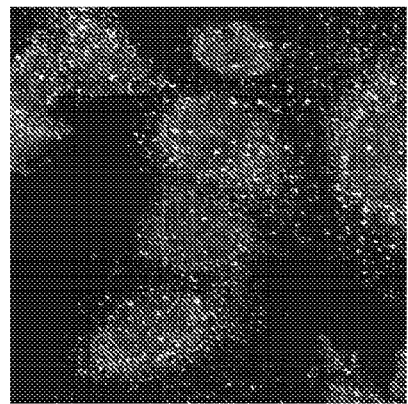

Data showed that significant shift in mean fluorescence intensity was observed only in cells treated with TcdA/A1H3 immune complex. In contrast, incubation with either A1H3 alone or TcdA/A1E6 did not cause a noticeable increase in fluorescence when compared to control cells (FIG. 8 panel A). The high affinity binding of TcdA/A1H3 immune complex to RAW 264.7 cells was further observed by confocal microscopy imaging. Strong signals were observed in these cells incubated with TcdA/A1H3 both at 4° C. (FIG. 8 panel D) and 37° C. (FIG. 8 panel E), temperatures that allow surface binding and subsequent internalization, respectively. No fluorescence was detected in RAW 264.7 cells incubated with A1H3 alone (FIG. 8 panel B) or with TcdA/A1E6 (FIG. 8 panel C).

Without being limited by any particular mechanism or theory, A1H3 might act as a bridge, facilitating the recruitment of TcdA to the cell surface via FcγRI. We therefore incubated RAW 264.7 cells and mRG1-1 cells with TcdA in the presence or absence of A1H3. Cells were stained with rabbit-anti-TcdA polyclonal antibodies followed by an Alexa-488-conjugated anti-rabbit-IgG antibody, and visualized under a confocal microscope. A much brighter signal was observed in RAW264.7 cells treated with TcdA in the presence of A1H3 (FIG. 9 panel B), but not in those incubated with TcdA alone (FIG. 9 panel A). Similar results were observed in FcγRI expressing mRG1-1 cells (FIG. 9 panels C and D). Our data suggested that the presence of A1H3 led to an enhanced surface binding and internalization of TcdA, contributing to the A1H3-mediated enhancement of toxin activity.

Example 19

Endocytosis of TcdA/A1H3 Immune Complex

Figure 10A:
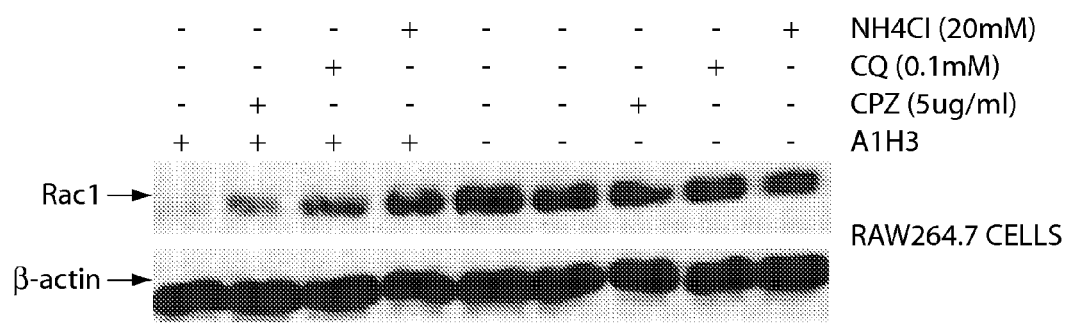
FIG. 10 is a set of photographs of Western blots and cell sorting readout data showing endocytosis-dependent Rac1 glucosylation and TNF-α production.
Figure 10B:
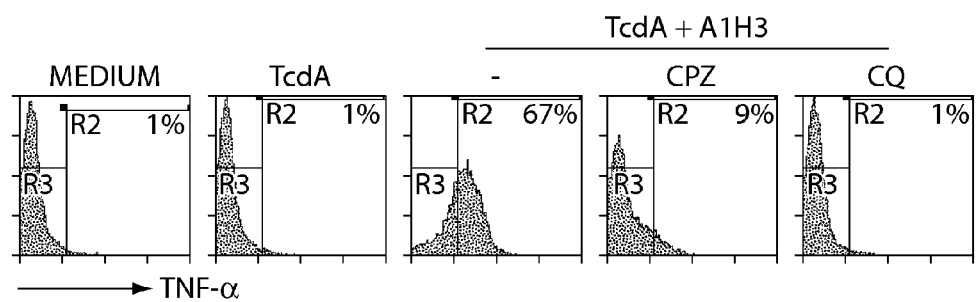
Figure 10C:
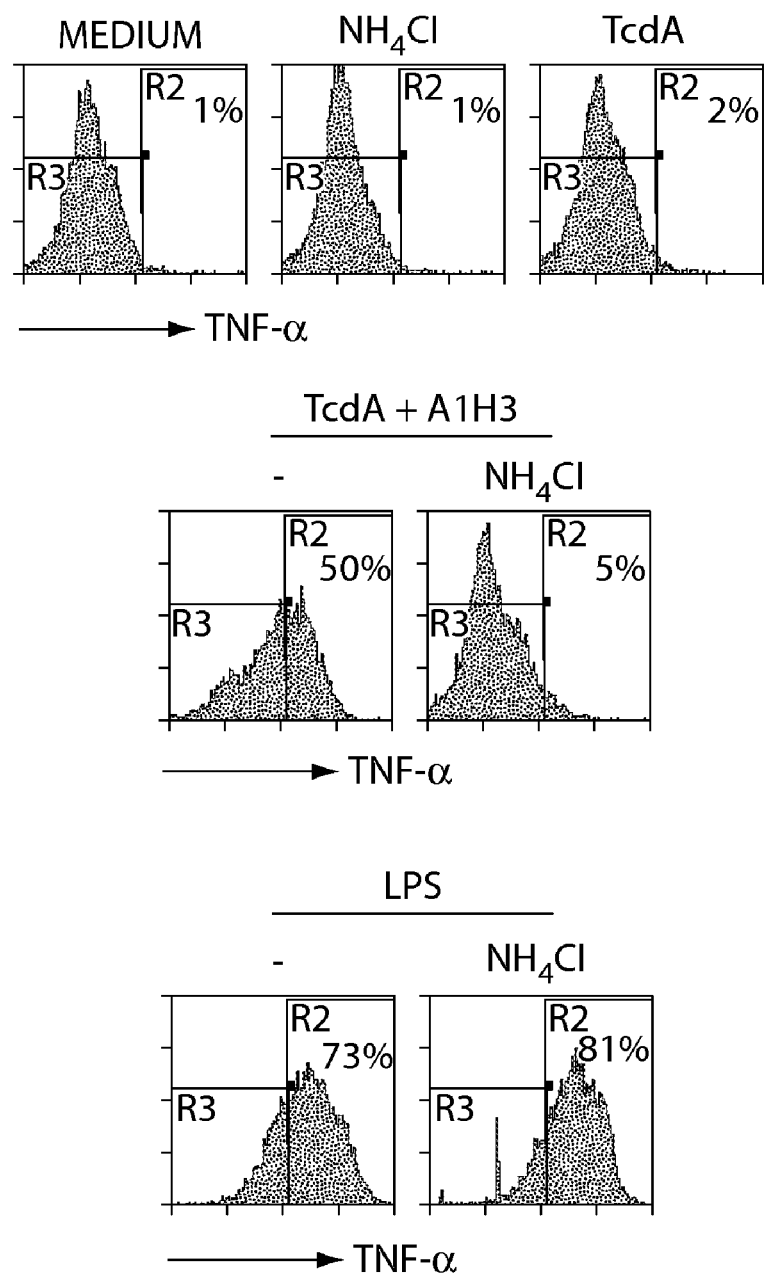
Figure 11A:
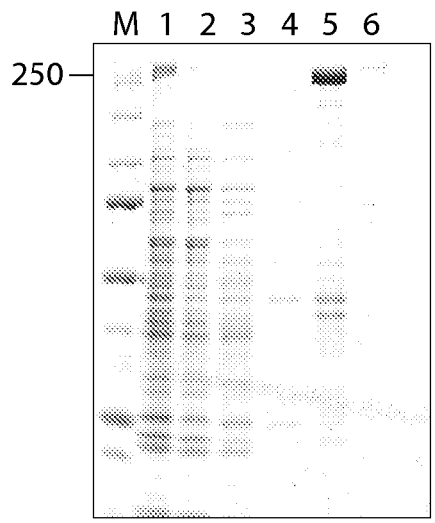
FIG. 11 is a set of photographs of SDS-PAGE showing expression and purification of recombinant TcdB. pHis-TcdB plasmid was transformed into B. megaterium protoplasts. Several transformed colonies were picked and screened to test expression of rTcdB induced by xylose in cultures of each transformant. M indicates molecular weight markers and 250 kDa is shown.
Figure 11B:
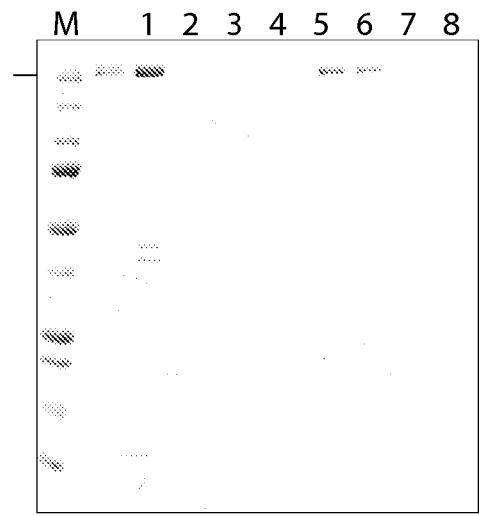
Figure 11C:
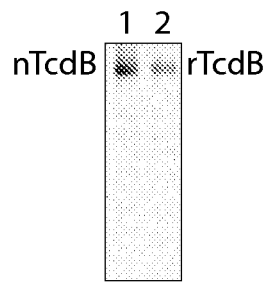
Figure 11D:
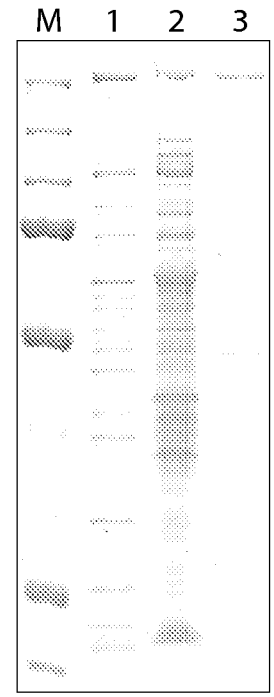

Macrophages internalize immune complexes by either endocytosis or phagocytosis. Soluble antigen-antibody immune complexes are most likely internalized via receptor-mediated endocytosis (Norman J C et al. 2000 FEBS letters 484:179-183). To dissect the molecular mechanisms underlying the FcγRI-mediated, A1H3-dependent enhancement of TcdA toxicity, we applied a panel of reagents that target various stages of the endocytic pathway. Chlorpromazine specifically inhibits the clathrin-coated pit formation at the plasma membrane. Pre-incubation of RAW 264.7 with chlorpromazine reduced the level of Rac1 glucosylation by TcdA/A1H3 immune complex (FIG. 10 panel A). Ammonium chloride and chloroquine, which prevent endosomal acidification, decreased the glucosyltransferase activity of TcdA/A1H3 (FIG. 10 panel A), supporting that the internalization of TcdA/A1H3 immune complex was mediated via receptor-mediated endocytosis.

One of the TcdA-mediated effects on macrophages is the production of TNF-α. As expected, chlorpromazine and chloroquine completely abolished TNF-α synthesis by TcdA/A1H3 immune complex in RAW 264.7 cells (FIG. 10 panel B). While ammonium chloride did not induce TNF-α production nor affected the cytokine response elicited by LPS, the presence of ammonium chloride at 20 mM completely blocked TcdA/A1H3 complex induced cytokine secretion (FIG. 10 panel C). The inhibitory effects of chlorpromazine and chloroquine but not by LPS on TNF-α production by TcdA/A1H3 further support the view that TcdA/A1H3 enters cells via receptor-mediated endocytosis.

Example 20

Cell Lines for Toxin Biochemistry

Human intestinal epithelial cell lines HCT-8 and mouse colonic epithelial cell CT26 were purchased from ATCC (Manassas, Va.), and cells were cultured in DMEM medium (Invitrogen, Carlsbad, Calif.) containing 2 mM L-glutamine, 100 U/ml penicillin G, 50 μg/ml streptomycin sulfate, and 10% fetal bovine serum.

Example 21

Purification of Native Toxins

Native TcdA and TcdB were purified from *C. difficile* strain VPI 10463 (kindly provided by Abraham L. Sonenshein, Tufts University School of Medicine) as described previously (Gerhard R et al. 2005 Microb Pathog 2005, 38(2-3):77-83). Briefly, a dialysis bag (100 kDa cutoff, Millpore, Billerica, Mass.) containing 100 ml of 0.9% NaCl immersed in a total volume of 1 liter of brain heart infusion (Difco, Lawrence, Kans.) was inoculated with 5 ml of an overnight culture of *C. difficile*, and the culture was grown at 37° C. for 72 h in an anaerobic chamber (Bactron BACLITE-1, Sheldon Manufacturing Inc., Cornelius, Oreg.). The supernatant collected from the dialysis bag was concentrated by ultrafiltration through an Amicon XM-100 membrane (Millipore). The concentrated supernatants were dialyzed against Tris-HCl (50 mM, pH 7.5) buffer overnight and loaded onto a HiTrap DEAE column (Amersham Biosciences, Piscataway, N.J.). The fractions containing toxins were collected and were passed through a thyroglobulin column, and the flow-through was further passed through a Mono Q column (Amersham Biosciences). The elutions from thyroglobulin and mono Q yielded TcdA and TcdB respectively.

Example 22

Constructs and Cloning

The tcdB gene was amplified from *C. difficile* (VPI 10463) chromosomal DNA using forward primer 5'-GCGCTGTA-CAATGAGTTTAGTTAATAGAAAAC-3' (SEQ ID NO: 5) and reverse primer 5'-ATATATGGTACCCTTCACTAAT-CACTAATTGAGC-3' (SEQ ID NO: 6). The PCR product was digested by BsrGI and KpnI enzymes, and then ligated to pHis1522 vector (MoBiTec, Goettingen, Germany). The full-length of tcdA gene was amplified using the primers 5'-GCGCTGTACAATGTCTTTAATATCTAAA-GAAGAGTTAA-3' (SEQ ID NO: 7) and 5'-ATATGCATGC-CCATATATCCCAGGGGCTTTTA-3' (SEQ ID NO: 8). The PCR product was digested by BsrGI and SphI, and then inserted into pHis1522 vector. Both sequences of tcdA and tcdB genes in pHis 1522 vector have been confirmed by DNA sequence using a panel of primers (Table 1). The gene encoding a 28-amino-acid signal peptide of *B. megaterium* extracellular esterase LipA (Malten M et al. 2006 Applied and environmental microbiology 72(2):1677-1679) that directs protein secretion in the secretory pathway of *B. megaterium* was synthesized by GeneArt (Regensburg, Germany) and inserted at the site of BsrGI of the tcdB construct. All restriction endonucleases were purchased from New England Biolabs (Cambridge, Mass.). All DNA cloning and plasmid construction were performed at Tufts University and approved by the Institutional Biosafety Committees and conformed with NIH Recombinant DNA technology guidelines.

TABLE 1

The sequences of DNA sequencing primers.

| | | | SEQ ID NO |
|---|---|---|---|
| tcdA Sequencing Primers | | | |
| TcdA-Seq1 | Forward | CTGCAGCATCTGACATAG | 9 |
| TcdA-Seq2 | Forward | AAGTTATGAAGCAACATGC | 10 |
| TcdA-Seq3 | Forward | TCATCTCCATCTATAAGTTCTC | 11 |
| TcdA-Seq4 | Forward | GTTTCTGGAAATTGTTTGG | 12 |
| TcdA-Seq5 | Forward | GTTACTGGATGGCAAACC | 13 |
| TcdA-Seq6 | Reverse | TAGTCCAATAGAGCTAGGTC | 14 |
| TcdA-Seq7 | Reverse | CCATGTCCAATAAAGGTTAC | 15 |
| TcdA-Seq8 | Reverse | ACTGCTCCAGTTTCCCAC | 16 |
| TcdA-Seq9 | Reverse | ACATTCTACCATTTCCG | 17 |
| TcdA-Seq10 | Reverse | ATAACCAGTTGAGGCTATG | 18 |
| tcdB Sequencing Primers | | | |
| TcdB-Seq1 | Forward | GAACAAGAGTTGGTAGAAAG | 19 |
| TcdB-Seq2 | Forward | TCTTGGTGAAGATGATAATC | 20 |
| TcdB-Seq3 | Reverse | CCTGGTAACATATCAACATC | 21 |
| TcdB-Seq4 | Reverse | CTCTCTCTGAACTTCTTGC | 22 |
| TcdB-Seq5 | Forward | CCTACATTATCTGAAGGATTAC | 23 |
| TcdB-Seq6 | Forward | GATGTTGATAATGTTGTGAGAG | 24 |
| TcdB-Seq7 | Forward | ATAGTAAGCCTTCATTTGG | 25 |
| TcdB-Seq8 | Reverse | GCTGCACCTAAACTTACAC | 26 |
| TcdB-Seq9 | Reverse | ATTACTTCCATTTACCTCAC | 27 |
| TcdB-Seq10 | Forward | TTATAGAGGAGCTGTAGAATG | 28 |
| TcdB-Seq11 | Reverse | GCTTTACCTGTTTCTGGG | 29 |
| Sequencing Prim in pHis-1522 vector | | | |
| phis-seq-F | Forward | TTTGTTTATCCACCGAACTAAG | 30 |
| phis-seq-R | Reverse | TGATTGGCTCCAATTCTTG | 31 |

Example 23

Expression of Recombinant Toxins

Transformation of *B. megaterium* protoplasts was performed according to the manufacturer's instruction (MoBiTec). The transformed *B. megaterium* colonies were each picked and transferred to LB medium cultures supplemented with 10 μg/ml tetracycline, and grown overnight in and diluted 1:30 in LB medium containing tetracycline and grown to an optical density ($OD_{600}$) around 0.3. Xylose (0.5% w/v) was added to induce protein expression. Bacteria were harvested by centrifugation 12 to 16 h after induction. In case of the secretory rTcdB, the culture supernatant was also collected.

Example 24

Purification of Recombinant Toxins

Purification of recombinant His-tagged rTcdB from bacterial lysate was performed by Ni-affinity chromatography following ion-exchange fractionation. Briefly, *B. megaterium* cells were centrifuged and the culture pellet from 100 ml of culture was resuspended in 5 ml lysis buffer (300 mM NaCl, 20 mM imidazole, 20 mM $NaH_2PO_4$, 500 μM EDTA, protease inhibitor cocktail (Cat #P8849, Sigma), adjusted to pH 8.0). Cells were disrupted by sonication and the lysate was centrifuged at 14,000 g for 20 mM. The supernatant was passed through a nickel-charged HiTrap chelating HP column (Amersham Biosciences, Piscataway, N.J.) and bound His-tagged rTcdB was eluted with an elution buffer containing 250 mM imidazole, 300 mM NaCl, and 20 mM Na $H_2PO_4$, pH 8.0. The eluent was desalted and applied to HiTrap Q column (Amersham Biosciences) and rTcdB was eluted by a gradient concentration of NaCl solution. Fractions containing rTcdB were combined and stored at −80° C. until use. To purify the rTcdB from supernatant, the bacterial supernatant was passed through a 0.45 μm filter, and was concentrated by ultrafiltration with a 100 kDa cutoff membrane (Millipore). Concentrated supernatant was purified by Ni-affinity chromatography following an ion-exchange fractionation as described herein. Recombinant rTcdA was purified by thyroglobulin affinity column and Ni-affinity chromatography (Krivan H C et al. 1987 Infect Immun 55(8):1873-1877).

Example 25

SDS-PAGE and Western Blot

CT26 cells were contacted with toxins for 5 h and were harvested. In other treatments, cells were pre-incubated with ammonium chloride for 30 min, and cells were then treated with toxins. The methods for SDS-PAGE and western blot have been described previously (Feng H et al. 2001 Blood 97(11):3505-3512; Feng H et al. 2005 J Immunol 175(1):421-432). Briefly, samples were boiled for 5 min in 1× NuPage SDS sample buffer (Invitrogen) and were loaded on a gradient (4-20%) sodium dodecyl sulfate-polyacrylamide gel (SDS-PAGE; BioRad, Hercules, Calif.). After electrophoresis, the gels were stained with GelCode Blue (Pierce, Rockford, Ill.) according to the manufacturer's instructions. For performing western blots, TcdB-specific monoclonal antibody (clone 5A8-E11, Meridian Life Science, Inc., Memphis, Tenn.), and/or TcdA-specific monoclonal antibodies (clone PCG4.1, Meridian Life Science, Inc.; or clone A1E6 generated in our laboratory), and HRP-conjugated anti-mouse IgG (Amersham Biochiences) were used as the primary and secondary antibodies, respectively. Protein bands were visualized by an enhanced chemiluminescence assay (ECL, Amersham Biochiences). To determine Rac1 glucosylation, an antibody (clone 102, BD Biosciences, San Diego, Calif.) specific for non-glucosylated form of Rac1 was used. Anti-actin antibody (clone AC-40, Sigma, St. Louis, Mo.) was used as an internal control to monitor an equal loading of samples.

Example 26

Cytotoxicity Assay

Subconfluent CT26 cells seeded in 96-well plates ($2 \times 10^4$/well) were incubated with toxins, bacterial culture supernatants, or with crude extracts. For blocking assays, 1 µl/well of rabbit anti-serum specific for TcdA was added simultaneously with toxins. Cells were cultured overnight and the morphological changes of CT26 cells were observed by light microscopy with a CCD camera. For the MTT assay, after 3 days of incubation, 10 µL of MTT (5 mg/ml) were added to each well and the plate was further incubated at 37° C. for 2 h. The formazan was solubilized with acidic isopropanol (0.4 N HCl in absolute isopropanol), and absorbance was measured at 570 nm using a 96-well ELISA reader. Cell viability was expressed as the percentage of survival of the control wells.

Example 27

Disruption of Tight Junctions by Recombinant Toxins

HCT-8 cells were seeded into a 24-well plate with 3-µm pore transwells (Corning Inc., Wilkes Barre, Pa.) and cultured for 10 to 14 days. Transepithelial resistance (TER) was monitored daily until TER reached 1000 $\Omega/cm^2$. Either rTcdA (300 ng/ml) or rTcdB (300 ng/ml) was added into the upper chamber of transwells for the indicated time. The cells were fixed and stained with anti-occludin (clone OC-3F10, Invitrogen) and fluorochrome-conjugate secondary antibodies. The slides were examined under confocal microscope (Leica LSM TSC SP2 AOBS).

Example 28

Cloning and Expression of the Recombinant Toxins

After enzyme (BsrGI/KpnI) digestion of pHis1522 vector and PCR products, a ligation reaction was performed and the mixture was incubated at 4° C. for 2 days. Transformation yielded more than 90 bacterial colonies that were further analyzed as follows. Plasmids (named pHis-TcdB) from these colonies were screened by digestion with a variety of enzymes. pHis-TcdB from each of multiple clones was used to transform B. megaterium protoplasts, and tetracycline-resistant clones were incubated with growth medium and induced with xylose. Crude extracts from approximately 30 different transformed clones were screened for activity causing rounding of cultured test cells. Clones with high activities were selected and were found to express a protein of about 270 kDa by a Coomassie-staining gel following xylose induction (FIG. 11 panel A Lane 1). This protein was purified by Ni-affinity column from a total crude extract, and displayed a major band of molecular weight about 270 kDa and some weak contaminant bands of lower molecular weights (FIG. 11 panel A). A further step of ion-exchange purification yielded a highly pure 270 kDa-protein without visible contaminant bands on Coomassie-stained gels (FIG. 11 panel B). Western blot analysis using specific antibodies against His-tags and toxin B (FIG. 11 panel C) identified the 270 kDa protein from B. megaterium lysate as the recombinant His-tagged toxin B (rTcdB). From one liter of bacterial culture, a yield of approximately 10 mg of rTcdB was obtained. The pHis-TcdB used to transform the B. megaterium was subjected to DNA sequencing for the verification of tcdB gene, and no mutation was found.

B. megaterium has a secretory pathway (Malten M et al. 2006 Applied and environmental microbiology 72(2):1677-1679; Vary P S et al. 2007 Applied microbiology and biotechnology 76(5):957-967), which transports expressed heterologous proteins into the medium. Because the native toxins are secreted into medium by toxigenic C. difficile, we attempted to express rTcdB in a secretory form. The DNA sequence encoding a 28-amino-acid signal peptide derived from B. megaterium extracellular esterase LipA (Malten M et al. 2006 Applied and environmental microbiology 72(2):1677-1679) was synthesized and inserted at the 5' of tcdB. The resulting pHis-SP-TcdB was transformed into B. megaterium. FIG. 11 panel D shows the presence of a 270 kDa band from the concentrated bacterial culture supernatant on a Coomassie stained SDS-PAGE gel (lane 2). Western blot and cytotoxicity assays confirmed the expression of the secretory form of rTcdB. The expression level of this secretory form was, however, very low and sufficient amounts of purified rTcdB could not be obtained from the supernatant.

Figure 12A:
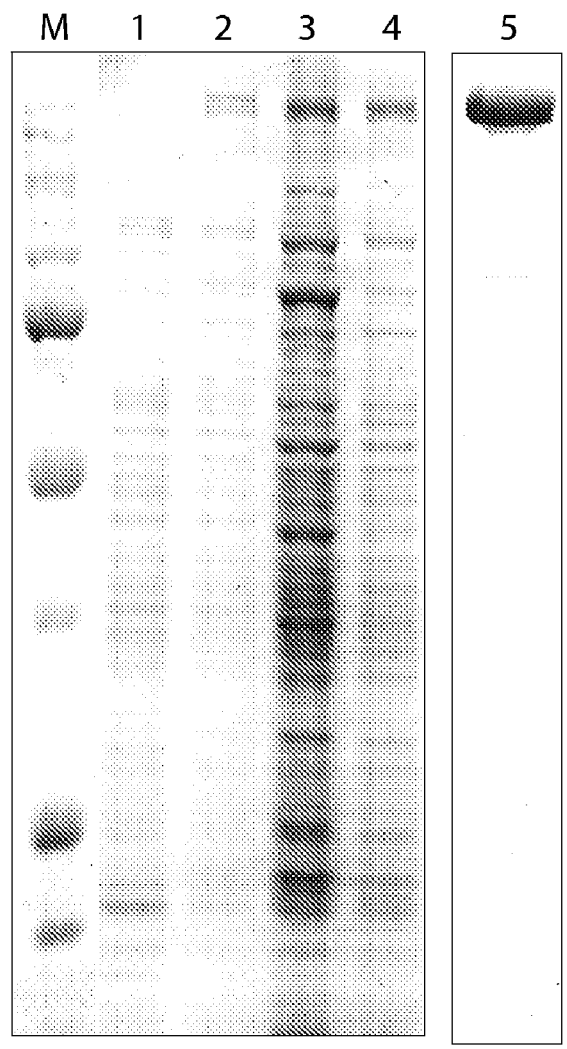
FIG. 12. is a set of photographs of SDS-PAGE showing expression and purification of recombinant TcdA. pHis-TcdA plasmid was transformed into B. megaterium protoplasts. More than 20 transformant colonies were picked and cultured and, expression of rTcdA was induced by xylose.
Figure 12B:
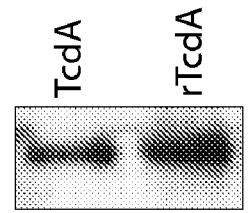
Figure 13A:
FIG. 13 is a set of photomicrographs showing cytopathic effect of recombinant toxins. Mouse colonic epithelial CT26 test cells in a 96-well plate were untreated (FIG. 13. panel A) or treated as follows: 100 culture supernatant from pHis-TcdB-transformed B. megaterium without induction by xylose (FIG. 13. panel B) or with xylose induction (FIG. 13. panel C); 10 μl culture supernatant from pHis-SP-TcdB-transformed B. megaterium with xylose induction (FIG. 13. panel D); rTcdB (1 ng/ml) (FIG. 13. panel E); native TcdB (1 ng/ml) (FIG. 13. panel F); rTcdB (10 ng/ml) (FIG. 13 panel G); native TcdB (10 ng/ml) (FIG. 13 panel H); rTcdA (20 ng/ml) (FIG. 13, panel I); native TcdA (20 ng/ml) (FIG. 13 panel J); rTcdA (200 ng/ml) (FIG. 13 panel K); native TcdA (200 ng/ml) (FIG. 13, panel L); rTcdA (200 ng/ml) with addition of 1 μl/well of rabbit anti-TcdA serum (FIG. 13 panel M); or native TcdA (200 ng/ml) with addition of 1 μl/well of rabbit anti-TcdA serum (FIG. 13 panel N). Cells were incubated overnight and the morphological changes were observed under a phase-contrast microscope.
Figure 13B:
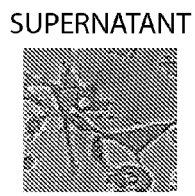
Figure 13C:
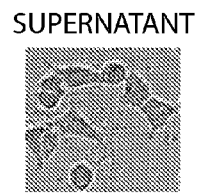
Figure 13D:
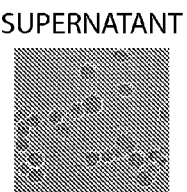
Figure 13E:
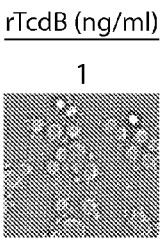
Figure 13F:
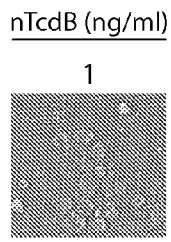
Figure 13G:
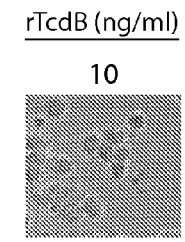
Figure 13H:
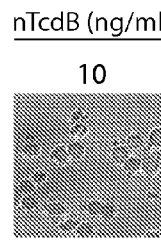
Figure 13I:
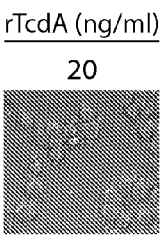
Figure 13J:
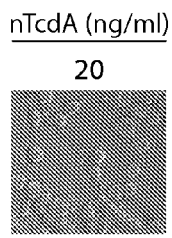
Figure 13K:
Figure 13L:
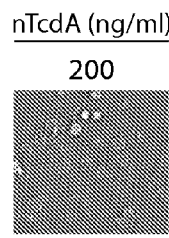
Figure 13M:
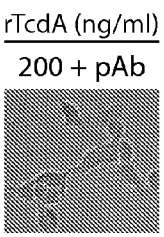
Figure 13N:
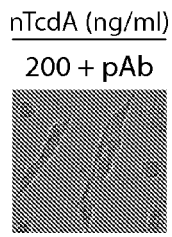

A similar strategy was utilized to clone and express recombinant TcdA. A clear protein band of 308 kDa was observed only after induction by xylose in a lysate of pHis-TcdA-transformed B. megaterium by SDS-PAGE Comassie stain (FIG. 12 panel A). His-tag combined with thyroglobulin affinity purifications resulted in a single strong band (FIG. 12 panel A Lane 5), which was confirmed as TcdA by western blot analysis (FIG. 12 panel B). DNA sequencing the pHis-TcdA used to transform the B. megaterium verified that the tcdA was free of mutations.

Example 29

Cytopathic Effect of Recombinant Toxins

Cytopathic effects of recombinant and native toxins were compared using cultured human epithelial HT-29 and mouse intestinal epithelial CT26 cells (FIG. 13). Purified rTcdA (FIG. 13 panels I and K) at 20 ng/ml or 200 ng/ml caused CT26 cell rounding similar to the results observed for native TcdA (FIG. 13 panels J and L). Both rTcdB and native TcdB were more potent, capable of causing cell rounding at a much lower concentration than those of rTcdA or native TcdA (FIG. 13 panels E, F, G, and H). After xylose induction, both supernatant (FIG. 13 panel D) and total cell lysate from pHis-SP-TcdB transformed B. megaterium caused cell rounding, whereas the bacterial culture supernatants from pHis-TcdB transformed B. megaterium with (FIG. 13 panel C) or without (FIG. 13 panel B) xylose induction did not cause cell rounding. The same concentration of xylose used to induced cells grown in BHI medium did not result in observation of cell rounding, indicating that the observed effects were specifically caused by the secreted toxin. Furthermore, the cytopathic effects of both rTcdA and native TcdA were blocked completely by a rabbit polyclonal antibody that is specific for TcdA (FIG. 13 panels M and N).

Example 30

Cytotoxic Effect of Recombinant Toxins

Figure 14A:
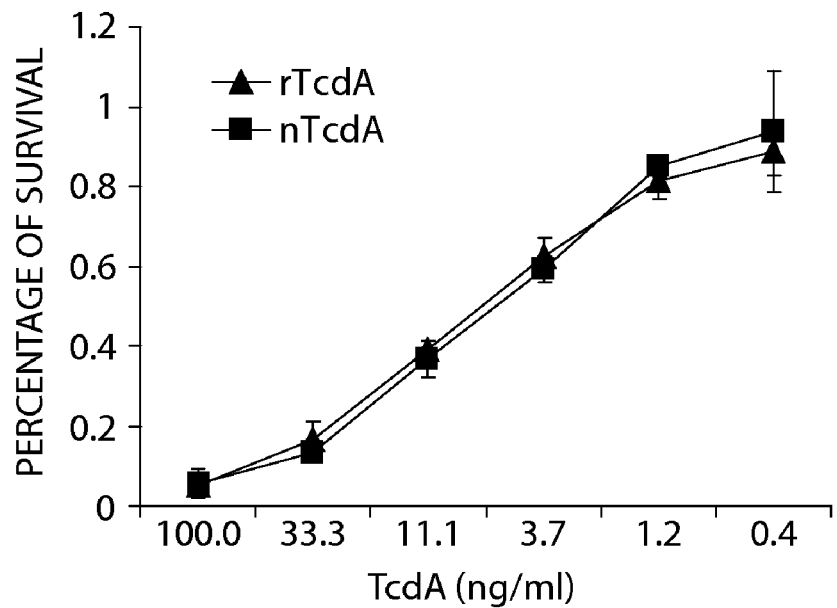
FIG. 14 is a set of line graphs showing cytotoxic effect of recombinant toxins. Mouse colonic epithelial CT26 test cells in a 96-well plate were exposed to native (□) or recombinant (Δ) TcdA (FIG. 14 panel A) or exposed to native (□) or recombinant (Δ) TcdB (FIG. 14 panel B) for 72 h. The MTT assay was performed and cell viability was expressed as a percentage of survival of control cells not exposed to toxin.
Figure 14B:
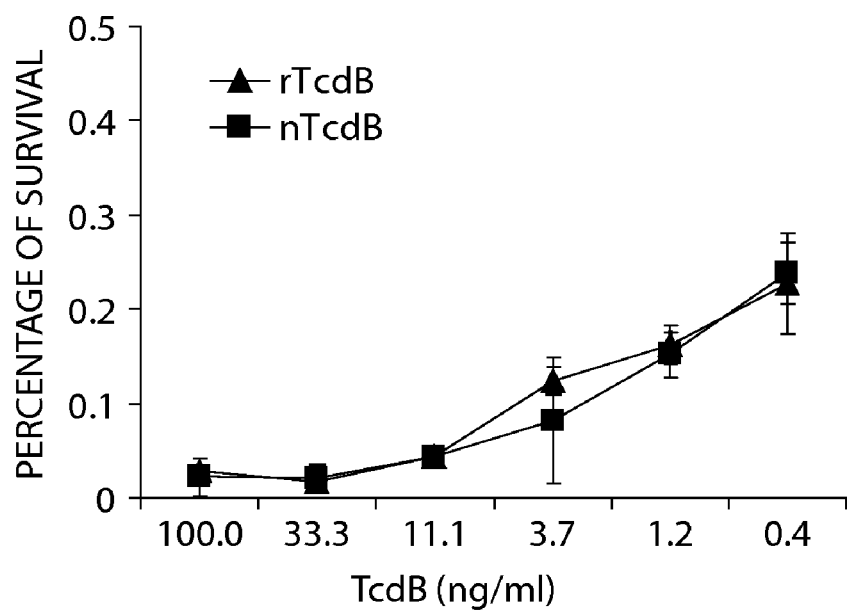

It has been demonstrated that both TcdA and TcdB induce intestinal epithelial cells to undergo apoptosis (Brito G A et al. 2002 J Infect Dis 186(10):1438-1447; Matarrese P et al. 2007 J Biol Chem 282(12):9029-41; Kim H et al. 2005 Gastroenterology 129(6):1875-1888). Therefore the cytotoxicity of recombinant toxins cultured to epithelial cells was compared to their native counterparts. As shown in FIG. 14 panel A, both native and recombinant TcdA induced a comparable and dose-dependent cell death of CT26 cells. Similarly, the exposure of CT26 cells to rTcdB induced a cell death that was comparable to nTcdB as determined by MTT assay (FIG. 14 panel B). These data indicate that the recombinant TcdA and TcdB have cytotoxic activity similar to that of their native counterparts in CT26 cells.

Example 31

Glucosylation of Rac1 by Recombinant Toxins

*C. difficile* TcdA and TcdB toxins function to target host cell Rho GTPase by glucosylating these proteins at the specific amino acid residues Thr37 (Rho A) or Thr35 (CDC42 and Rac1) (Just I et al. 1995 Nature 375(6531):500-503; Just I et al. 1995 J Biol Chem 270(23):13932-13936). To determine whether recombinant toxins can glucosylate Rac1 protein of host cells, mouse intestinal epithelial CT26 cells were treated with recombinant or native TcdA and TcdB for 5 h. Data obtained from Western blot (FIG. 15 panel A) showed that each of rTcdA and nTcdA treatment induced a dose-dependent, reduced recognition of Rac1 by monoclonal antibody (anti-Rac1 clone 102) that recognizes non-glucosylated Rac1 (Genth H et al. 2006 FEBS letters 580(14):3565-3569). The reduced recognition of Rac1 did not result from protein degradation, because amount of total Rac1 protein remained unchanged as determined by Western blot with an antibody (clone 23A8) recognizing both glucosylated and unmodified Rac1. Each of rTcdA and nTcdA at 40 ng/ml resulted in a complete glucosylation of Rac1 whereas 8 ng/ml or 1.6 ng/ml of TcdA led to a partial glucosylation. Exposure to rTcdB or nTcdB resulted in a complete glucosylation of Rac1 at a dose range from 0.4 ng/ml-2 ng/ml (FIG. 15 panel B), indicating that the glucosyltransferase activity of TcdB was more potent than TcdA. These results were consistent with the activity of native *C. difficile* toxins in which TcdB is more toxic to cultured cells than TcdA. The treatment of rTcdA and rTcdB also led to the glucosylation of Rac1 in RAW 264.7 cells and CHO cells.

Figure 15A:
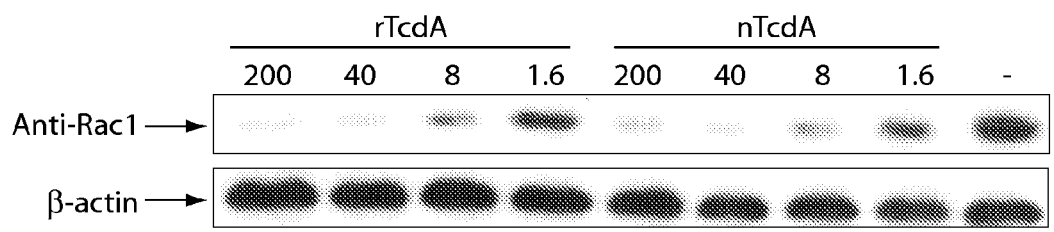
FIG. 15 is a set of photographs of Western blots showing glucosylation of Rac1 by recombinant toxins. CT26 test cells were either untreated or were treated with the indicated amount of native or recombinant TcdA (FIG. 15 panel A) and TcdB (FIG. 15 panel B) for 5 h.
Figure 15B:
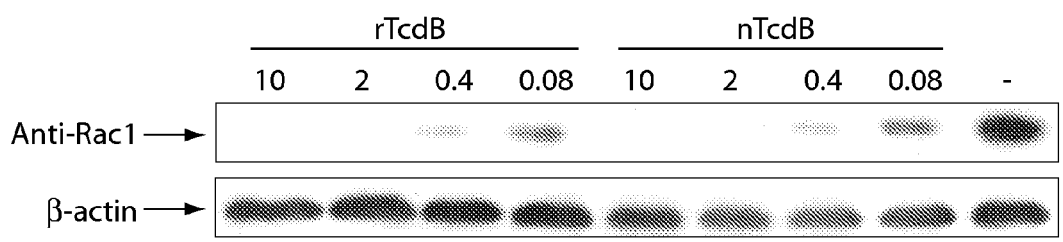
Figure 15C:
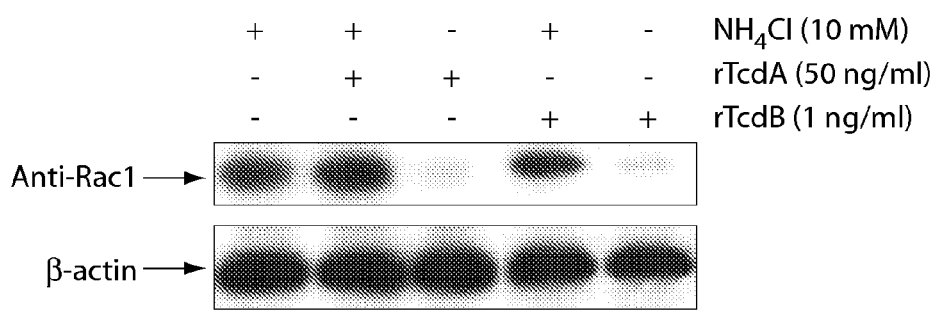
Figure 16A:
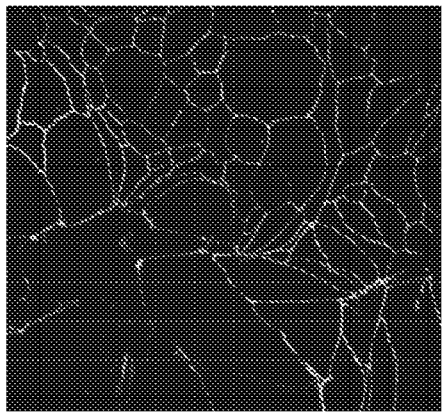
FIG. 16 is a set of photomicrographs showing disruption of tight junctions by recombinant toxins. HCT-8 cells on transwells were cultured until tight junctions formed. The polarized monolayers were untreated (FIG. 16 panel A) or treated with 300 ng/ml of rTcdA for 2 h (FIG. 16 panel B), 4 h (FIG. 16 panel C), and 6 h (FIG. 16 panel D); or with rTcdB 300 ng/ml for 2 h (FIG. 16 panel E), and 4 h (FIG. 16 panel F). Cells on the transwell membrane were fixed and stained with anti-occludin and fluorochrome-conjugated secondary antibodies, and were visualized under a confocal microscope.
Figure 16B:
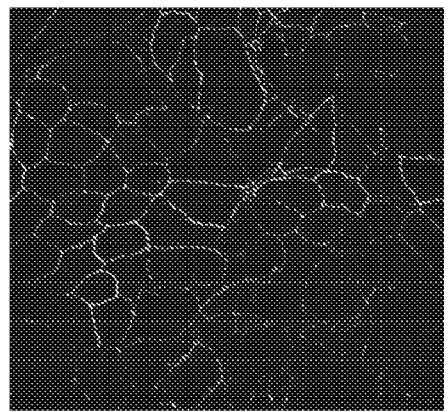
Figure 16C:
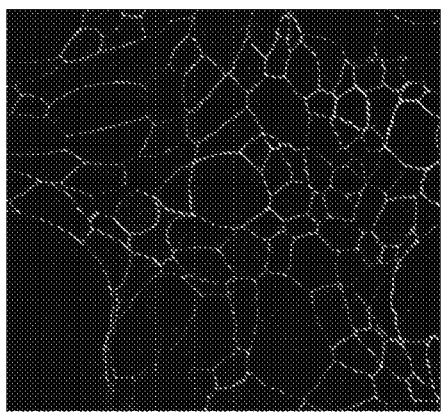
Figure 16D:
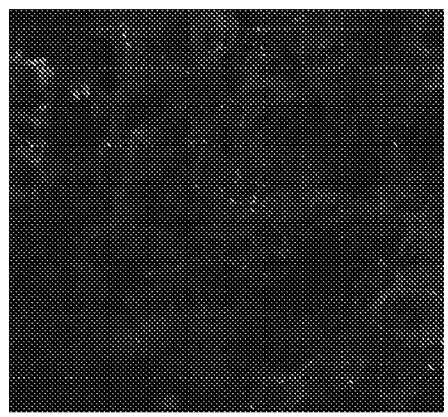
Figure 16E:
Figure 16F:
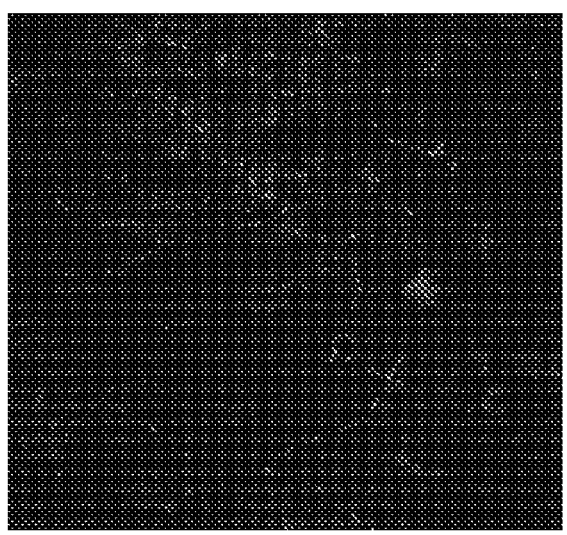

Both TcdA and TcdB are thought to bind to specific cellular receptor(s), which mediate their cellular uptake through endocytosis (Na X et al. 2008 Infect Immun 76(7):2862-2871; Pothoulakis C et al. 1996 J Clin Invest 98(3):641-649; Krivan H C et al. 1986 Infect Immun 53(3):573-581). Lysosomotropic agents such as chloroquine and $NH_4Cl$ can inhibit toxin-mediated cytotoxicity, suggesting that endosomal acidification is involved in toxin intracellular trafficking (Henriques B et al. 1987 Microbial pathogenesis 2(6):455-463; Jefferson K K et al. 1999 J Immunol 163(10):5183-5191). To determine whether or not the cellular activity of the recombinant toxins also requires endosomal acidification, CT26 cells were pre-incubated with $NH_4Cl$ for 30 min before the toxin exposure. While the exposure of CT26 cells to rTcdA or rTcdB induced the glucosylation of Rac1, pretreatment of cells with ammonium chloride was observed to have completely blocked such an activity (FIG. 15 panel C).

Example 32

Disruption of Tight Junctions of Intestinal Epithelial Cells by Recombinant Toxins TcdA and TcdB alter the structure of intestinal epithelia by disrupting tight junctions (Nusrat A et al. 2001 Infect Immun 69(3):1329-1336). Therefore whether or not the recombinant toxins herein have similar activities was investigated. Human intestinal epithelial HCT-8 cells were cultured in a transwell for 10 to 14 days until transepithelial resistance (TER) reached 1000 $\Omega$*$cm^2$ and tight junctions were formed (FIG. 16 panel A). Purified rTcdA was observed not to alter cell-cell connections of HCT-8 cells within 4 h of treatment (FIG. 16 panels B and C) but to disrupt tight junctions after 6 h of treatment (FIG. 16 panel D). Purified rTcdB, at the same concentration with rTcdA, was observed to completely disrupt the tight junctions of HCT-8 within 2 h of treatment (FIG. 16 panels E and F).

CDAD is largely attributed to the bacterial exotoxins TcdA and TcdB, although other virulence factors probably also play some roles (Voth D E et al. 2005 Clin Microbiol Rev 18(2):247-263). Both toxins glycosylate Rho GTPase family proteins, leading to their inactivation (Cloud J et al. 2007 Curr Opin Gastroenterol 23(1):4-9; Voth D E et al. 2005 Clin Microbiol Rev 18(2):247-263). To study the pathogenesis of CDAD and host immune response to the toxins, and to use the toxins as a research tool for signal transduction involving Rho GTPases, it is necessary to obtain large quantities of highly purified active TcdA and TcdB. Native toxins can be purified from toxigenic *C. difficile* culture supernatant. The purification process prior to the present methods however has involved multiple steps such as ultrafiltration, ammonium sulfate precipitation, and ion-exchange chromatography (Sullivan N M et al. 1982 Infect Immun 35(3):1032-1040; Keel M K et al. 2007 Veterinary pathology 44(6):814-822). In the case of TcdA, affinity purification through thyroglobulin is available and relatively pure TcdA can be obtained (Krivan H C et al. 1987 Infect Immun 55(8):1873-1877 and unpublished data). TcdB however is often contaminated with unknown substances even after extensive purification steps (Keel M K et al. 2007 Veterinary pathology 44(6):814-822). The *E. coli* system is popular and is widely used for the expression of recombinant proteins. Several studies have reported to have cloned and expressed active *C. difficile* toxins in *E. coli*, but failed to demonstrate that the purified toxins were obtained from bacterial extracts (Phelps C J et al. 1991 Infection and immunity 59(1):150-153; Tang-Feldman Y J et al. 2002 Molecular and cellular probes 16(3):179-183; Wren B W et al. 1987 FEBS letters 225(1-2):82-86). Recombinant TcdB, however, has not previously been stably expressed in *B. megaterium*, while only low levels of expressed TcdA have previously been observed (Burger S et al. 2003 Biochem Biophys Res Commun 307(3):584-588). In examples herein a full-length recombinant TcdB in *B. megaterium* was expressed at high levels, and greatly enhanced levels of recombinant TcdA were also produced.

Because *E. coli* expression system is widely used and easy-to-handle, various *E. coli* expression vector systems were first chosen to clone and express both toxins. However, data showed that both recombinant TcdA and TcdB were expressed in *E. coli* purified toxins could not be obtained from the bacterial lysate. The large size of the heterologous proteins may possibly be prone to protease digestion, and intrinsic protease activities of these toxins may also contribute to the instability (Reineke J et al. 2007 Nature 446(7134):415-419; Egerer M et al. 2007 The Journal of biological chemistry 282(35):25314-25321). Another possible reason for the inability to obtain purified recombinant toxins from *E. coli* is that the expression level was too low. In fact, large proteins are difficult to express at high levels in *E. coli*. Furthermore, an unusually high content of AT (~70%) in these clostridial gene sequences and a different codon usage make them particularly difficult to express at a high level in *E. coli* (Makoff A J et al. 1989 Nucleic acids research 17(24):10191-10202; Makoff A J et al. 1989 Biotechnology 7:1043-1046).

Several advantages are associated with *B. megaterium* expression system including lack of alkaline phosphatase and endotoxin LPS. Initially, the reported cloning strategy was attempted but was unsuccessful (Burger S et al. 2003 Biochem Biophys Res Commun 307(3):584-588). This might be due to the extremely low ligation when putting several fragments together during the cloning efficiency (Burger S et al. 2003 Biochem Biophys Res Commun 307(3):584-588). The strategy herein was changed to using a direct PCR amplification of whole toxin genes. However, this strategy was associated with a potential risk that PCR might introduce mutations due to the large size of the genes (7101 bp and 8133 bp for tcdB and tcdA respectively). Because of the large size of both genes, obtaining a sequence of all constructs in order to identify the correct clones was not practicable. Therefore, a functional approach, screening for recombinant protein expression and cytotoxicity, was taken. As many colonies as possible (more than 90) were screened after ligation and then the resulting constructed shuttle vectors were transformed into B. megaterium protoplasts. Selected colonies were subjected to screening again by examining the cytotoxic activity in bacterial crude extracts. The specific expression of recombinant toxins from the positive colonies (with cytotoxic activity) was then determined by Western blot. The plasmids encoding tcdA or tcdB respectively were finally subjected to DNA sequencing and no single mutation was found in either of the toxin genes.

The average yields of recombinant TcdA and TcdB were about 5 mg/ml-10 mg/ml of bacterial culture, which is much greater than that of native toxins from *C. difficile* culture, and up to 20-fold higher than the amount of rTcdA reported (Burger S et al. 2003 Biochem Biophys Res Commun 307(3): 584-588). The fact that a different shuttle vector was used from that of previous attempts (Burger S et al. 2003 Biochem Biophys Res Commun 307(3):584-588) might explain our higher yields of recombinant proteins. In addition, a twelve- to sixteen-hour period of induction with xylose yielded more recombinant proteins than five hours as suggested by the manufacturer. The other possible explanation was that the tcdA gene was fused into orfl of the vector in the construct previously reported (Burger S et al. 2003 Biochem Biophys Res Commun 307(3):584-588), resulting in a gene encoding modified N-terminus of recombinant TcdA. This modification might affect the efficiency of protein expression and/or its stability. The tcdA or tcdB gene was here inserted into the BsrGI site and the protein translation directly started from toxin gene, resulting in recombinant toxins without any N-terminal modification.

To facilitate purification, a $His_6$ tag was fused to the C-terminus of both toxins. One-step purification with a Ni-affinity chromatography resulted in approximately 70-80% purity of recombinant toxins as determined by Coomassie staining of SDS-PAGE (FIG. 1 and data not shown). To achieve a greater purity, an additional step was introduced after Ni-affinity chromatography. For rTcdA, thyroglobulin affinity purification was used. rTcdB was further purified by an anion-exchange fractionation (FIG. 11 panel B). These additional purification steps for rTcdA and rTcdB, respectively, led to highly pure recombinant toxins. No additional band was seen on a Coomassie-stained gel (FIG. 11 panel B for rTcdB, and FIG. 12 panel A for rTcdA). In addition, no detectable TLR2 or TLR4 stimulants were observed within the purified recombinant toxins as determined by sensitive bioassays. This is important because use of impure proteins to study host immune response or signaling transduction would possibly result in artificial results and unintended consequences.

A protein secretory pathway is present in *B. megaterium* (Malten M et al. 2006 Applied and environmental microbiology 72(2):1677-1679; Vary P S et al. 2007 Applied microbiology and biotechnology 76(5):957-967). A 28-amino-acid signal peptide of *B. megaterium* extracellular esterase LipA can direct the transport of expressed heterologous proteins into medium and the sequence is removed by a protease after secretion (Malten M et al. 2006 Applied and environmental microbiology 72(2):1677-1679). Because of the nature of exotoxins of native toxins and relatively easy purification from supernatant without the need for sonication or other means of cell disruptions, expression of rTcdB was sought extracellularly. After inserting the gene of the leader signaling peptide at the 5' of tcdB, we were able to generate active secretory rTcdB (FIG. 3D) and Coomassie staining of concentrated supernatant on a SDS-PAGE gel and western blot showed rTcdB band (FIG. 11 panel D). However, for some unknown reasons, the expression level of rTcdB was significantly decreased when the leader sequence was introduced to the construct. In addition, the secretion was observed to be inefficient as toxin molecules were observed trapped within the bacteria, and the bacterial lysate contained toxin activity. The partition of rTcdB in the medium and the cytoplasm might also be due to the inefficient refolding after their extracellular transport.

Examples herein demonstrate full-length recombinant *C. difficile* toxin A and B proteins successfully expressed in *B. megaterium* and great improvement in the yield of the recombinant toxins has. About 5 mg-10 mg of highly purified rTcdA or rTcdB was obtained from one liter of bacterial culture. These recombinant toxins had similar biological activities with their native counterparts. The recombinant toxin proteins provide an invaluable tool for studying the pathogenesis of *C. difficile* associated disease and host immune response to toxins, as well as tools for studying the signaling transduction involving Rho GTPase family proteins.

What is claimed is:

1. A method for detecting a presence of *Clostridium difficile* toxin and/or toxigenic *C. difficile* in a biological sample, the method comprising:

contacting a first set of test cells with an aliquot of the sample and an amount of a toxin-enhancing antibody, wherein the test cells express an IgG Fc gamma receptor (FcγR), wherein the toxin-enhancing antibody is a monoclonal IgG isotype selected from the group of A1H3 and PCG4.1 that complexes with the toxin to enhance binding of the toxin to a cell surface of the test cells expressing the FcγR and enhances cytotoxic activity and detection of effect of the *C. difficile* toxin by binding to and enhancing cell death of the test cells by the toxin; and measuring cell death in the first set of test cells in comparison with a second set of the test cells not so contacted and otherwise identical as a negative control, such that the extent of test cell death in the first set of test cells in comparison to the second set of test cells indicates the presence of *Clostridium difficile* toxin and/or toxigenic *C. difficile* in the sample, whereby the toxin-enhancing antibody enhances detection of the presence of the *C. difficile* toxin in the biological sample.

2. The method according to claim 1, further comprising contacting at least a third set of test cells with at least one known amount of *C. difficile* toxin as a positive control.

3. The method according to claim 2, further comprising contacting at least a fourth set of test cells with a different known amount of *C. difficile* toxin wherein a plurality of positive controls comprises a standard curve for toxin killing in the presence of the toxin-enhancing antibody.

4. The method according to claim 1, wherein measuring the cell death comprises measuring at least one selected from the group of: decrease in respiration by a tetrazolium dye, increase in cell rounding, increase in glucosylation of Rac1, increase in cytoskeleton disruption, increase in necrosis, increase in endocytosis of antibody-toxin, increase in apoptosis, and decrease in cell attachment to a surface by electronic sensing of resistance or impedance.

5. The method according to claim 1, wherein the test cells are white blood cells or colonic epithelial cells.

6. The method according to claim 1, wherein the white blood cells are macrophages or mouse RAW264.7 cells.

7. The method according to claim 1, wherein the toxin-enhancing antibody is specific for an epitope of *C. difficile* toxin protein selected from the group of TcdA and TcdB.

8. The method according to claim 7, wherein the toxin-enhancing antibody has an IgG2a isotype.

9. The method according to claim 1, wherein the method further comprises detecting in a milliliter of the sample the presence of toxin that is less than about fifty picograms, less than about 10 picograms, less than about 5 picograms, or less than about one picogram.

10. The method according to claim 1, wherein measuring cell attachment by resistance or impedance comprises measuring real-time cell electronic sensing (RT-CES) in a multi-cell culture dish or E-plate.

11. The method according to claim 1, wherein the test cells are at least one selected from the group consisting of: defrosted frozen cells contacted absent culturing; defrosted frozen cells cultured prior to use; primary cells; and cultured cells.

12. The method according to claim 1, further comprising analyzing cell death data from the first and second sets of cells and optionally from the standard curve, wherein the steps of contacting, measuring, and analyzing are accomplished in less than about 24 hours, less than about eight hours, less than about six hours, or less than about three hours.

13. The method according claim 1, further comprising identifying the presence of the toxin with a neutralizing antibody or an anti-toxin that binds at least one *C. difficile* toxin, the method further comprising prior to contacting, pre-mixing the sample and neutralizing antibody, wherein observing that neutralizing antibody or anti-toxin reduces extent of cell death of test cells further indicates a presence of a *C. difficile* toxin infection.

* * * * *

UNITED STATES PATENT AND TRADEMARK OFFICE
CERTIFICATE OF CORRECTION

| | | |
|---|---|---|
| PATENT NO. | : 8,206,940 B2 | Page 1 of 1 |
| APPLICATION NO. | : 12/992330 | |
| DATED | : June 26, 2012 | |
| INVENTOR(S) | : Feng et al. | |

It is certified that error appears in the above-identified patent and that said Letters Patent is hereby corrected as shown below:

On column 1, lines 18-21, delete "The present invention was supported in part by grants NIH N01 AI030050 and NIH K01 DK076549 from the National Institutes of Health. The government has certain rights in the invention."

and insert --This invention was supported by AI030050 awarded by the National Institutes of Health. The government has certain rights in the invention.--

Signed and Sealed this
Thirtieth Day of October, 2012

David J. Kappos
*Director of the United States Patent and Trademark Office*

SEQUENCE LISTING

```
<160> NUMBER OF SEQ ID NOS: 31

<210> SEQ ID NO 1
<211> LENGTH: 57
<212> TYPE: DNA
<213> ORGANISM: Clostridium difficile

<400> SEQUENCE: 1
ggttgctgga tccataagag atttataccc aggtaaattt tactggagat tctatgc        57

<210> SEQ ID NO 2
<211> LENGTH: 64
<212> TYPE: DNA
```

<213> ORGANISM: Clostridium difficile

<400> SEQUENCE: 2
ccatgctgag ctcgcattat ttatattgat aatcctttta actaatttac tatcttcatc    60
atag                                                                  64

<210> SEQ ID NO 3
<211> LENGTH: 61
<212> TYPE: DNA
<213> ORGANISM: Clostridium difficile

<400> SEQUENCE: 3
ggttgctgga tcctcattat tctattttga tcctatagaa tttaacttag taactggatg    60
g                                                                     61

<210> SEQ ID NO 4
<211> LENGTH: 48
<212> TYPE: DNA
<213> ORGANISM: Clostridium difficile

<400> SEQUENCE: 4
ccatgctgag ctcgcgccat atatcccagg ggcttttact ccatcaac                  48

<210> SEQ ID NO 5
<211> LENGTH: 32
<212> TYPE: DNA
<213> ORGANISM: Clostridium difficile

<400> SEQUENCE: 5
gcgctgtaca atgagtttag ttaatagaaa ac                                   32

<210> SEQ ID NO 6
<211> LENGTH: 34
<212> TYPE: DNA
<213> ORGANISM: Clostridium difficile

<400> SEQUENCE: 6
atatatggta cccttcacta atcactaatt gagc                                 34

<210> SEQ ID NO 7
<211> LENGTH: 38
<212> TYPE: DNA
<213> ORGANISM: Clostridium difficile

<400> SEQUENCE: 7
gcgctgtaca atgtctttaa tatctaaaga agagttaa                             38

<210> SEQ ID NO 8
<211> LENGTH: 32
<212> TYPE: DNA
<213> ORGANISM: Clostridium difficile

<400> SEQUENCE: 8
atatgcatgc ccatatatcc caggggcttt ta                                   32

<210> SEQ ID NO 9
<211> LENGTH: 18
<212> TYPE: DNA
<213> ORGANISM: Clostridium difficile

<400> SEQUENCE: 9
ctgcagcatc tgacatag                                                   18

```
<210> SEQ ID NO 10
<211> LENGTH: 19
<212> TYPE: DNA
<213> ORGANISM: Clostridium difficile

<400> SEQUENCE: 10
aagttatgaa gcaacatgc                                                    19

<210> SEQ ID NO 11
<211> LENGTH: 22
<212> TYPE: DNA
<213> ORGANISM: Clostridium difficile

<400> SEQUENCE: 11
tcatctccat ctataagttc tc                                                22

<210> SEQ ID NO 12
<211> LENGTH: 19
<212> TYPE: DNA
<213> ORGANISM: Clostridium difficile

<400> SEQUENCE: 12
gtttctggaa attgtttgg                                                    19

<210> SEQ ID NO 13
<211> LENGTH: 18
<212> TYPE: DNA
<213> ORGANISM: Clostridium difficile

<400> SEQUENCE: 13
gttactggat ggcaaacc                                                     18

<210> SEQ ID NO 14
<211> LENGTH: 20
<212> TYPE: DNA
<213> ORGANISM: Clostridium difficile

<400> SEQUENCE: 14
tagtccaata gagctaggtc                                                   20

<210> SEQ ID NO 15
<211> LENGTH: 20
<212> TYPE: DNA
<213> ORGANISM: Clostridium difficile

<400> SEQUENCE: 15
ccatgtccaa taaaggttac                                                   20

<210> SEQ ID NO 16
<211> LENGTH: 18
<212> TYPE: DNA
<213> ORGANISM: Clostridium difficile

<400> SEQUENCE: 16
actgctccag tttcccac                                                     18

<210> SEQ ID NO 17
<211> LENGTH: 18
<212> TYPE: DNA
<213> ORGANISM: Clostridium difficile

<400> SEQUENCE: 17
acatttctac catttccg                                                     18
```

```
<210> SEQ ID NO 18
<211> LENGTH: 19
<212> TYPE: DNA
<213> ORGANISM: Clostridium difficile

<400> SEQUENCE: 18
ataaccagtt gaggctatg                                                19

<210> SEQ ID NO 19
<211> LENGTH: 20
<212> TYPE: DNA
<213> ORGANISM: Clostridium difficile

<400> SEQUENCE: 19
gaacaagagt tggtagaaag                                               20

<210> SEQ ID NO 20
<211> LENGTH: 20
<212> TYPE: DNA
<213> ORGANISM: Clostridium difficile

<400> SEQUENCE: 20
tcttggtgaa gatgataatc                                               20

<210> SEQ ID NO 21
<211> LENGTH: 20
<212> TYPE: DNA
<213> ORGANISM: Clostridium difficile

<400> SEQUENCE: 21
cctggtaaca tatcaacatc                                               20

<210> SEQ ID NO 22
<211> LENGTH: 19
<212> TYPE: DNA
<213> ORGANISM: Clostridium difficile

<400> SEQUENCE: 22
ctctctctga acttcttgc                                                19

<210> SEQ ID NO 23
<211> LENGTH: 22
<212> TYPE: DNA
<213> ORGANISM: Clostridium difficile

<400> SEQUENCE: 23
cctacattat ctgaaggatt ac                                            22

<210> SEQ ID NO 24
<211> LENGTH: 22
<212> TYPE: DNA
<213> ORGANISM: Clostridium difficile

<400> SEQUENCE: 24
gatgttgata atgttgtgag ag                                            22

<210> SEQ ID NO 25
<211> LENGTH: 19
<212> TYPE: DNA
<213> ORGANISM: Clostridium difficile

<400> SEQUENCE: 25
atagtaagcc ttcatttgg                                                19
```

```
<210> SEQ ID NO 26
<211> LENGTH: 19
<212> TYPE: DNA
<213> ORGANISM: Clostridium difficile

<400> SEQUENCE: 26
gctgcaccta aacttacac                                                  19

<210> SEQ ID NO 27
<211> LENGTH: 20
<212> TYPE: DNA
<213> ORGANISM: Clostridium difficile

<400> SEQUENCE: 27
attacttcca tttacctcac                                                 20

<210> SEQ ID NO 28
<211> LENGTH: 21
<212> TYPE: DNA
<213> ORGANISM: Clostridium difficile

<400> SEQUENCE: 28
ttatagagga gctgtagaat g                                               21

<210> SEQ ID NO 29
<211> LENGTH: 18
<212> TYPE: DNA
<213> ORGANISM: Clostridium difficile

<400> SEQUENCE: 29
gctttacctg tttctggg                                                   18

<210> SEQ ID NO 30
<211> LENGTH: 22
<212> TYPE: DNA
<213> ORGANISM: Clostridium difficile

<400> SEQUENCE: 30
tttgtttatc caccgaacta ag                                              22

<210> SEQ ID NO 31
<211> LENGTH: 21
<212> TYPE: DNA
<213> ORGANISM: Clostridium difficile
<220> FEATURE:
<221> NAME/KEY: misc_feature
<222> LOCATION: (1)..(1)
<223> OTHER INFORMATION: n is a, c, g, or t

<400> SEQUENCE: 31
ngtgattggc tccaattctt g                                               21
```